US006057130A

United States Patent [19]
Grinnell

[11] Patent Number: 6,057,130
[45] Date of Patent: May 2, 2000

[54] METHOD OF USING EUKARYOTIC EXPRESSION VECTORS COMPRISING THE BK VIRUS ENHANCER

[75] Inventor: Brian W. Grinnell, Indianapolis, Ind.

[73] Assignee: Eli Lilly and Company, Indianapolis, Ind.

[21] Appl. No.: 09/174,231

[22] Filed: Oct. 16, 1998

Related U.S. Application Data

[62] Division of application No. 09/056,966, Apr. 8, 1998, Pat. No. 5,879,919, which is a division of application No. 08/459,916, Jun. 2, 1995, Pat. No. 5,770,397, which is a division of application No. 08/208,930, Mar. 9, 1994, Pat. No. 5,550,036, which is a continuation of application No. 07/368,700, Jun. 20, 1989, abandoned, which is a continuation-in-part of application No. 07/250,001, Sep. 27, 1988, abandoned, which is a continuation-in-part of application No. 07/129,028, Dec. 4, 1987, abandoned, which is a continuation-in-part of application No. 06/849,999, Apr. 9, 1986, abandoned.

[51] Int. Cl.[7] .................................................. C12P 21/02
[52] U.S. Cl. ................... 435/69.1; 435/235.1; 435/320.1
[58] Field of Search ............................... 435/69.1, 235.1, 435/320.1

[56] References Cited

U.S. PATENT DOCUMENTS

| 4,562,155 | 12/1985 | Ricciardi et al. | 435/172.3 |
|---|---|---|---|
| 4,775,624 | 10/1988 | Bang et al. | 435/226 |
| 4,959,318 | 9/1990 | Foster et al. | 435/69.1 |
| 4,965,199 | 10/1990 | Capon et al. | 435/69.6 |
| 5,506,118 | 4/1996 | Berg et al. | 435/691 |
| 5,550,036 | 8/1996 | Grinnell | 435/69.1 |

FOREIGN PATENT DOCUMENTS

| 85301617 | 9/1985 | European Pat. Off. . |
|---|---|---|
| 0191606 | 8/1986 | European Pat. Off. . |
| 0215548 | 3/1987 | European Pat. Off. . |
| 0245949 | 11/1987 | European Pat. Off. . |
| 0246049 | 11/1987 | European Pat. Off. . |
| WO87/04722 | 8/1987 | WIPO . |

OTHER PUBLICATIONS

Yang and Wu, 1979, *Science* 206: 456–462.
Seif, et al., 1979, *Cell* 18: 963–977.
Rosenthal, et al., 1983, *Science* 222: 749–755.
Milanesi, et al., 1984, *Molecular and Cellular Biology* 4: 8, 1551–1560.
Khoury and Gruss, 1983, *Cell* 33: 313–314.
Borrelli, et al., 1984, *Nature* 312: 608–612.
Velcich and Ziff, 1985, *Cell* 40: 705–716.
Hen, et al., 1985, *Science* 230: 1391–1394.
Wood, et al., 1984, *Nature* 112: 330–337.
Zain, et al., 1979, *Cell* 16: 851–861.
Solnick, 1981, *Cell* 24: 135–143.
Berkner and Sharp, 1985, *Nuc. Acids Res.* 13(3): 841–857.
Kaufman, 1984, *Proc. Natl. Acad. Sci. USA* 82: 689–693.
Mansour, et al., 1985, *Proc. Natl. Acad. Sci. USA* 82: 1359–1363.
Davis, et al., 1985, *Proc. Natl. Acad. Sci. USA* 82: 7560–7564.
Wasylyk, et al., 1983, *Cell* 32: 503–514.
Imperiale, et al., 1983, *Cell* 35: 127–136.
Green, et al., 1983, *Cell* 35: 137–148.
Gaynor, et al., 1984, *Proc. Natl. Acad. Sci. USA* 81: 1193–1197.
Alwine, 1985, *Mol. and Cell. Biol.* 5(5): 1034–1042.
Lewis and Manley, 1985, *Nature* 317: 169–171.
Lebkowski, et al., 1985, *Nature* 317: 169–171.
Weeks and Jones, 1985, *Nuc. Acids Res.* 13(14) 5389–5402.
Leff and Chambon, 1986, *Mol. and Cell. Biol.* 6(1): 201–208.
Yan, et al., 1987, *Fed. Proc.* 46 2243.
Grinnell, et al., 1986, abstract from Tumor Virus Meeting, Cold Spring, Harbor.
Grinnell, et al., 1986, *Mol. Cell. Biol.* 6(11):3596–3605.
Grinnell, et al., 1987, abstract from 17th Steenbock Symposium.
Foster, et al., 1987, *Biochemistry* 26: 7003–7011.
Kumar, et al., 1986, *Proc. Nat. Acad. Sci.* 83: 3199–3203.
Spangler, et al., 1987, *Science* 237: 1044–1046.
Alonso–Caplen, et al., 1987, abstract from Translational Control Meeting.
Hauschka, et al., 1986, *Haemostasis* 16: 273–287.
Choo, et al., 1986, *Gene* 46: 277–286.
Sastry, et al., 1985, *Biochem Biophys. Res. Comm.* 132: 795–803.
Christman, et al., 1982, *Proc. Natl. Acad. Sci. USA* 79: 1815–1819.
Deschatnette, et al., 1985, *Proc. Natl. Acad. Sci. USA* 82: 765–769.
Hau, L. and Salem, H., 1988, *Thrombosis and Haemostasis* 60: 267–270.

(List continued on next page.)

*Primary Examiner*—James Ketter
*Attorney, Agent, or Firm*—Brian P. Barrett; Steven P. Caltrider; Lynn D. Apelgren

[57] ABSTRACT

The present invention is a method of using the BK enhancer in tandem with a eukaryotic promoter to promote transcription of DNA that encodes a useful substance. The method of the present invention requires the presence of the E1A gene product for maximum expression of the useful substance. The present invention also comprises a number of useful expression vectors that comprise the BK enhancer in tandem with the adenovirus 2 late promoter positioned to drive expression of a variety of proteins, such as protein C, chloramphenicol acetyltransferase, and tissue plasminogen activator. The present invention further comprises a method for increasing the activity of the BK enhancer involving placement of the BK enhancer immediately upstream of the eukaryotic promoter used in tandem with the BK enhancer to drive expression of a useful substance. Furthermore, the present invention also comprises a method for coamplification of genes in primate cells. Additionally, the invention further comprises the recombinant human protein C molecule produced in 293 cells which comprises novel glycosylation patterns.

26 Claims, 42 Drawing Sheets

OTHER PUBLICATIONS

Grinnell, et al., 1987, *BioTechnology* 5: 1189–1192.
Kawasaki, et al., 1976, *J. Biol. Chem.* 251: 1296–1302.
Goto, et al., 1988, *BioTechnology* 6: 67–71.
Foster, et al., 1984, *Proc. Natl. Acad. Sci. USA* 81: 4766–4770.
Keller, et al., 1985, *Mol. Cell. Biol.* 5(8): 1859–1869.
Pohjanpelto, et al., 1985, *Mol. Cell. Biol.* 5(6): 1385–1390.
Brady, et al., *Proc. Natl. Acad. Sci. USA* 82: 7299–7303.

XhoI → Treat with Kenow enzyme → Ligate to BamHI linkers → BamHI → Circularize by ligation PstI

METHOD OF USING EUKARYOTIC EXPRESSION VECTORS COMPRISING THE BK VIRUS ENHANCER

CROSS-REFERENCE TO RELATED APPLICATIONS

This application is a divisional application of U.S. patent application Ser. No. 09/056,966, filed Apr. 8, 1998, now U.S. Pat. No. 5,879,919, which is a divisional application of U.S. patent application Ser. No. 08/459,916, filed Jun. 2, 1995, now U.S. Pat. No. 5,770,397, which is a divisional application of U.S. application Ser. No. 08/208,930, filed Mar. 9, 1994, now U.S. Pat. No. 5,550,036, which is a continuation application of U.S. application Ser. No. 07/368,700, filed Jun. 20, 1989, now abandoned, which is a continuation-in-part application of U.S. patent application Ser. No. 07/250,001, filed Sep. 27, 1988, now abandoned, which is a continuation-in-part application of U.S. patent application Ser. No. 07/129,028, filed Dec. 4, 1987, now abandoned which is a continuation-in-part application of U.S. patent application Ser. No. 06/849,999, filed Apr. 9, 1986, abandoned.

BACKGROUND OF THE INVENTION

The present invention concerns a method of using the BK enhancer in the presence of an immediate-early gene product of a large DNA virus to increase transcription of a recombinant gene in eukaryotic host cells. The BK enhancer is a defined segment of DNA that consists of three repeated sequences (the prototype BK enhancer is depicted in Example 17, below). However, a wide variety of BK enhancer variants, not all consisting of three repeated sequences, are known in the art and suitable for use in the invention.

The BK enhancer sequence exemplified herein is obtained from BK virus, a human papovavirus that was first isolated from the urine of an immunosuppressed patient. BK virus is suspected of causing an unapparent childhood infection and is ubiquitous in the human population. Although BK virus grows optimally in human cells, the virus undergoes an abortive cycle in non-primate cells, transforms rodent cells in vitro, and induces tumors in hamsters. BK virus is very similar to SV40, but the enhancer sequences of the two papovaviruses, SV40 and BK, differ substantially in nucleotide sequence. The complete nucleotide sequence of BK virus (~5.2 kb) has been disclosed by Seif et al., 1979, Cell 18:963, and Yang and Wu, 1979, Science 206:456. Prototype BK virus is available from the American Type Culture Collection (ATCC), 12301 Parklawn Dr., Rockville, Md. 20852-1776, under the accession number ATCC VR-837. A restriction site and function map of prototype BK virus is presented in FIG. 1 of the accompanying drawings.

Enhancer elements are cis-acting and increase the level of transcription of an adjacent gene from its promoter in a fashion that is relatively independent of the position and orientation of the enhancer element. In fact, Khoury and Gruss, 1983, Cell 33:313, state that "the remarkable ability of enhancer sequences to function upstream from, within, or downstream from eukaryotic genes distinguishes them from classical promoter elements . . ." and suggest that certain experimental results indicate that "enhancers can act over considerable distances (perhaps >10 kb)."

The present invention teaches that unexpected increases in transcription result upon positioning the BK enhancer immediately upstream of (on the 5' side of) the "CAAT" region of a eukaryotic promoter that is used in tandem with the BK enhancer to transcribe a DNA sequence encoding a useful substance. The CAAT region or "immediate upstream region" or "−80 homology sequence" is a cis-acting upstream element that is a conserved region of nucleotides observed in promoters whose sequences for transcriptional activity have been dissected. The CAAT region is found in many, but not all, promoters. In other promoters, equivalent cis-acting upstream elements are found, including SP1 binding sites, the octa sequence, nuclear factor 1 binding sites, the AP1 and AP2 homologies, glucocorticoid response elements, and heat-shock response elements. The CAAT region equivalent in the adenovirus major late promoter is the upstream transcription factor (UTF) binding site (approximate nucleotides −50 to −65 upstream of the CAP site). The CAAT sequence mediates the efficiency of transcription and, with few exceptions, cannot be deleted without decreasing promoter strength.

Enhancer elements have been identified in a number of viruses, including polyoma virus, papilloma virus, adenovirus, retrovirus, hepatitis virus, cytomegalovirus, herpes virus, papovaviruses, such as simian virus 40 (SV40) and BK, and in many non-viral genes, such as within mouse immunoglobulin gene introns. Enhancer elements may also be present in a wide variety of other organisms. Host cells often react differently to different enhancer elements. This cellular specificity indicates that host gene products interact with the enhancer element during gene expression.

Enhancer elements can also interact with viral gene products present in the host cell. Velcich and Ziff, 1983, Cell 40:705; Borrelli et al., 1984, Nature 312:608; and Hen et al., 1985, Science 230:1391, disclose that the adenovirus-2 early region 1A (E1A) gene products repress activation of transcription induced by the SV40, polyoma virus, mouse immunoglobulin gene and adenovirus-2 E1A enhancers. Eukaryotic expression vectors that utilized enhancers to increase transcription of recombinant genes consequently were not expected to work better than vectors without enhancers in E1A-containing host cells. In striking contrast to the prior art methods of using enhancers, the present method for using the BK virus enhancer element involves using the E1A gene product or a similar immediate-early gene product of a large DNA virus to maximize gene expression. Thus, the present invention teaches that the ability of the BK enhancer to promote transcription of DNA is increased in the presence of the E1A gene product of any adenovirus.

The E1A gene product (actually, the E1A gene produces two products, which are collectively referred to herein as "the E1A gene product") is an immediate-early gene product of adenovirus, a large DNA virus. The present invention encompasses the use of any immediate-early gene product of a large DNA virus that functions similarly to the E1A gene product to increase the activity of the BK enhancer. The herpes simplex virus ICP4 protein, described by DeLuca et al., 1985, Mol. Cell. Biol. 5: 1997–2008, the pseudorabies virus IE protein, described by Feldman et al., 1982 P.N.A.S. 79:4952–4956, and the E1B protein of adenovirus are all immediate-early gene products of large DNA viruses that have functions similar to the E1A protein. Therefore, the method of the present invention includes the use of the ICP4, IE, or E1B proteins, either in the presence or absence of E1A protein, to increase the activity of the BK enhancer.

SUMMARY OF THE INVENTION

The present invention concerns a method of using the BK virus enhancer in the presence of an immediate-early gene product of a large DNA virus, such as the EIA gene product of adenovirus, for purposes of increasing transcription and expression of recombinant genes in eukaryotic host cells. Another significant aspect of the present invention relates to a variety of expression vectors that utilize the BK enhancer sequence in tandem with a eukaryotic promoter, such as the adenovirus late promoter (MLP), to drive expression of useful products in eukaryotic host cells. Many of these expression vectors comprise a BK enhancer-adenovirus late promoter cassette, which can be readily transferred to other vectors for use in the present method. The versatility of the present expression vectors is demonstrated by the high-level expression driven by these vectors of such diverse proteins as chloramphenicol acetyltransferase, protein C, tissue plasminogen activator, and modified tissue plasminogen activator.

In the construction of certain vectors of the invention, the BK enhancer and SV40 enhancer were placed in tandem at the front (5') end of the MLP, itself positioned to drive expression of a recombinant gene on a recombinant DNA expression vector. This tandem placement yielded unexpectedly higher levels of expression in cells that did not express the immediate-early gene product of a large DNA virus. Consequently, a further aspect of the invention is a method of producing a gene product in a recombinant host cell that comprises transforming the host cell with a recombinant DNA vector that comprises two different enhancers placed at the 5' end of the coding sequence for the gene product and culturing the transformed cell under conditions that allow for gene expression.

The practice of the invention to express human protein C in adenovirus-transformed cells led to the discovery that such cells are especially preferred hosts for the production of γ-carboxylated proteins. Consequently, a further aspect of the invention comprises a method for making γ-carboxylated proteins.

Yet another important aspect of the present invention concerns a method of increasing the activity of the BK enhancer relative to an adjacent eukaryotic promoter and is illustrated using the BK enhancer-adenovirus-2 late promoter cassette. These derivatives were constructed by enzymatic treatment that positioned the BK enhancer very close to the CAAT region of the adenovirus-2 late promoter. Dramatic increases in expression levels, as compared with constructions that lack this positioning, were observed when these modified BK enhancer-adenovirus late promoter sequences were incorporated into expression vectors and then used to drive expression of useful gene products in eukaryotic host cells. Thus, the present invention provides a method for increasing the activity of the BK enhancer relative to an adjacent eukaryotic promoter that comprises positioning the enhancer immediately upstream, within 0 to about 300 nucleotides, of the 5' end of the CAAT region or CAAT region equivalent of the eukaryotic promoter.

Yet another aspect of the invention results from attempts to increase expression of recombinant products encoded on the vectors described herein by incorporation of portions of the tripartite leader sequence of adenovirus into those expression vectors. Significant increases in expression result when the first part of the tripartite leader of adenovirus is encoded into a recombinant DNA expression vector, and such expression can be further increased in some situations by action of the VA gene product of adenovirus.

An additional aspect of the present invention concerns a method of amplification of genes in primate cells. The most widely used method for gene amplification employs the murine dihydrofolate reductase gene for selection and amplification in a dhfr deficient cell line. Human polypeptides often require post-translational modifications which occur most efficiently in primate cells, yet most primate cells cannot be directly selected or amplified using only the dhfr system. The present invention provides a method wherein the primate cells are first isolated using a directly selectable marker, then amplified using the dhfr system, thereby significantly increasing the expression levels from primate cells.

Another aspect of the present invention concerns novel recombinantly produced human protein C molecules which contain glycosylation patterns totally unlike the human protein C molecules derived from plasma. The novel recombinantly produced protein C molecules display functional activities which are quite different than plasma-derived human protein C. Furthermore, the recombinant human protein C molecules derived from 293 cells contain fewer sialic acid residues than the plasma-derived human protein C.

For purposes of the present invention, the following terms are as defined below.

Antibiotic—a substance produced by a microorganism that, either naturally or with limited chemical modification, will inhibit the growth of or kill another microorganism or eukaryotic cell.

Antibiotic Resistance-Conferring Gene—a DNA segment that encodes an activity that confers resistance to an antibiotic.

ApR—the ampicillin-resistant phenotype or gene conferring same.

Cloning—the process of incorporating a segment of DNA into a recombinant DNA cloning vector.

CmR—the chloramphenicol-resistant phenotype or gene conferring same.

dhfr—dihydrofolate reductase.

ep—a DNA segment comprising the SV40 early promoter of the T-antigen gene, the T-antigen binding sites, and the SV40 origin of replication.

Eukaryotic promoter—any DNA sequence that functions as a promoter in eukaryotic cells.

HmR—the hygromycin-resistant phenotype or gene conferring same.

IVS—DNA encoding an intron, also called an intervening sequence.

Large DNA virus—a virus that infects eukaryotic cells and has a genome greater than ~10 kb in size, i.e., any of the pox viruses, adenoviruses, and herpes viruses.

MLP—the major late promoter of adenovirus, which is also referred to herein as the late promoter of adenovirus.

NeoR—the neomycin resistance-conferring gene, which can also be used to confer G418 resistance in eukaryotic host cells.

ori—a plasmid origin of replication.

pA—a DNA sequence encoding a polyadenylation signal.

Promoter—a DNA sequence that directs transcription of DNA into RNA.

Recombinant DNA Cloning Vector—any autonomously replicating or integrating agent that comprises a DNA molecule to which one or more additional DNA segments can be or have been added.

Recombinant DNA Expression Vector—any recombinant DNA cloning vector comprising a promoter and associated insertion site, into which a DNA molecule that encodes a useful product can be inserted and expressed.

Recombinant DNA Vector—any recombinant DNA cloning or expression vector.

Replicon—any DNA sequence that controls the replication of a recombinant DNA vector.

Restriction Fragment—any linear DNA generated by the action of one or more restriction enzymes.

rRNA—ribosomal ribonucleic acid.

Sensitive Host Cell—a host cell that cannot grow in the presence of a given antibiotic or other toxic compound without a DNA segment that confers resistance thereto.

Structural Gene—any DNA sequence that encodes a polypeptide, inclusive of that DNA encoding the start and stop codons.

Structural Polypeptide—any useful polypeptide, including, but not limited to, human protein C, tissue plasminogen activator, insulin, thrombomodulin, factor Va or factor VIIIa.

TcR—the tetracycline-resistant phenotype or gene conferring same.

Transformant—a recipient host cell that has undergone transformation.

Transformation—the introduction of DNA into a recipient host cell.

tRNA—transfer ribonucleic acid.

DETAILED DESCRIPTION OF THE INVENTION

The present invention concerns an improved method for producing a useful substance in a eukaryotic host cell wherein said cell is transformed with a recombinant DNA vector that comprises a eukaryotic promoter, a BK enhancer positioned to stimulate said promoter, and a DNA sequence that encodes said useful substance, said sequence being positioned for expression from said promoter, and wherein said cell containing said vector is cultured under conditions suitable for expression of said useful substance, wherein the improvement comprises: (a) providing said cell with a DNA sequence that codes for the expression of an immediate-early gene product of a large DNA virus; and (b) culturing said cell of step a) under conditions suitable for expressing said gene product and stimulating the activity of said enhancer. Those skilled in the art recognize that many established cell lines express an immediate-early gene product of a large DNA virus and that such cell lines are especially useful in the present method. Thus, the present invention also comprises an improved method for producing a useful substance in a eukaryotic host cell wherein said cell is transformed with a recombinant DNA vector that comprises a eukaryotic promoter, a BK enhancer positioned to stimulate said promoter, and a DNA sequence that encodes said useful substance, said sequence being positioned for expression from said promoter, and wherein said cell containing said vector is cultured under conditions suitable for expression of said useful substance, wherein the improvement comprises: (a) inserting said vector into a eukaryotic host cell that expresses an immediate-early gene product of a large DNA virus, and (b) culturing said cell of step a) under conditions suitable for expressing said gene product and stimulating the activity of said enhancer.

An important aspect of the present invention is the novel group of expression vectors that comprise the BK enhancer sequence in tandem with the adenovirus-2 late promoter. The expression vectors of the present invention were constructed so that DNA molecules encoding useful products can be or have been readily inserted into the vectors in the correct position for expression. Furthermore, the BK enhancer sequence and eukaryotic promoter have been constructed to form a "cassette," which can be isolated from the expression vectors on a relatively small restriction fragment. The cassette can be readily shuttled between a variety of expression vectors. The expression vectors specifically exemplified herein utilize the adenovirus-2 or BK late promoter in the BK enhancer-eukaryotic promoter cassette that drives transcription in the method of the present invention.

Figure 2:
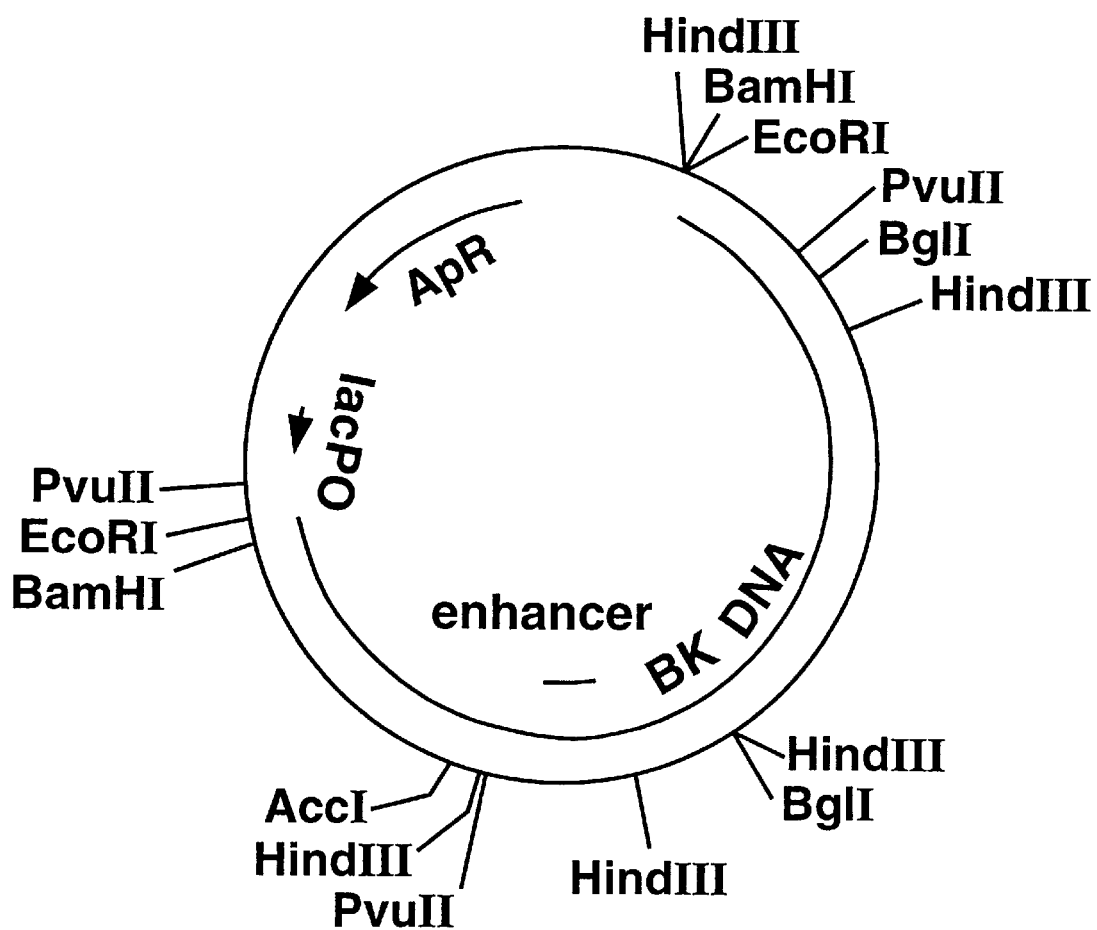
FIG. 2 is a restriction site and function map of plasmid pBKE1.

Although BK virus (ATCC VR-837) can be purchased or readily isolated in large quantities as described in Example 1, it is also convenient to clone the BK viral DNA onto a plasmid cloning vector and use the recombinant vector as a source of BK viral DNA sequences. Consequently, BK viral DNA was digested with restriction enzyme EcoRI, which, due to the presence of only one EcoRI site on the BK genome, produced linear BK DNA. Plasmid pUC8 (available from Bethesda Research Laboratories (BRL), P.O. Box 6009, Gaithersburg, Md. 20877) was likewise digested and linearized with restriction enzyme EcoRI, and the EcoRI-cut plasmid pUC8 DNA was ligated to the EcoRI-cut BK viral DNA to form plasmids pBKE1 and pBKE2, which differ only with respect to the orientation of the BK viral DNA. A restriction site and function map of plasmid pBKE1 is presented in FIG. 2 of the accompanying drawings. The construction of plasmids pBKE1 and pBKE2 is described in Example 2.

Figure 3:
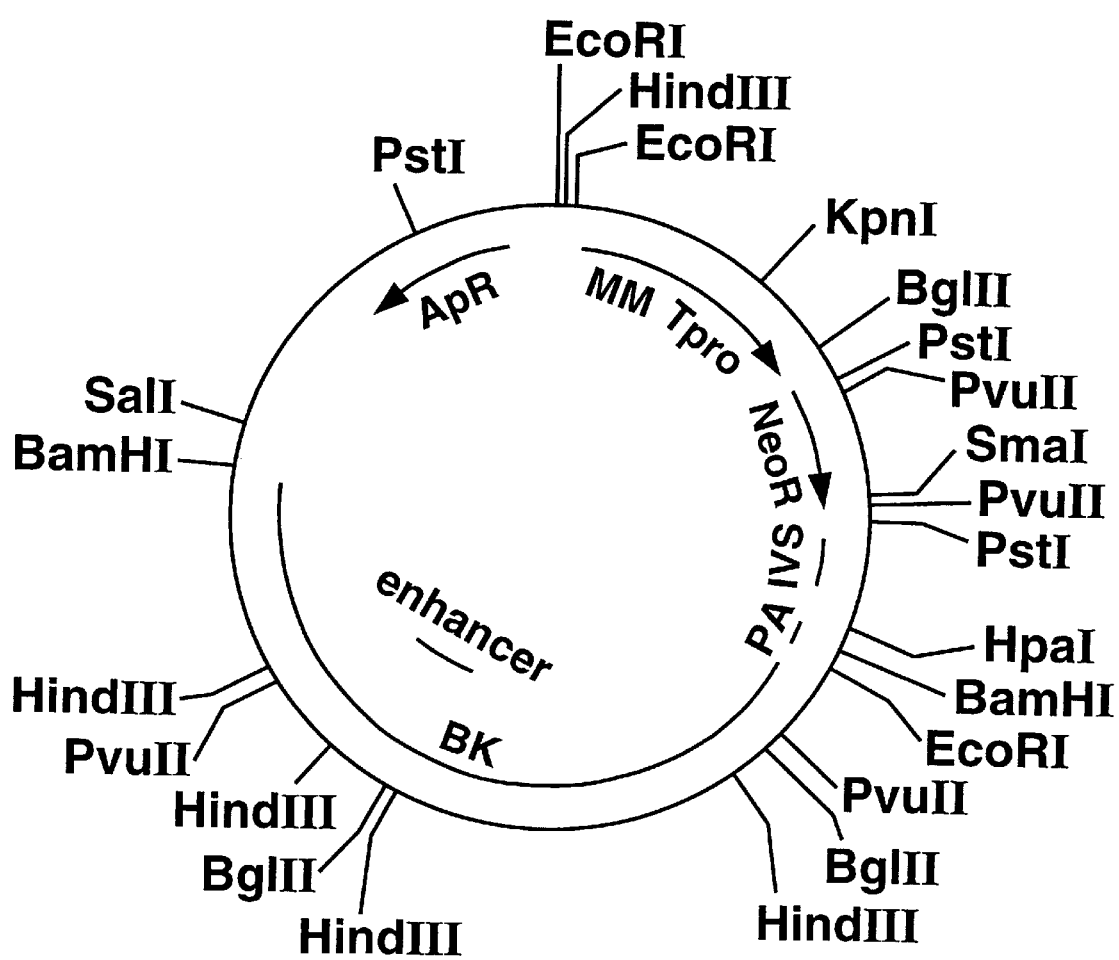
FIG. 3 is a restriction site and function map of plasmid pBKneo1.

The BK viral genome has also been combined with a portion of plasmid pdBPV-MMTneo to construct plasmids pBKneo1 and pBKneo2. Plasmid pdBPV-MMTneo, about 15 kb in size and available from the ATCC under the accession number ATCC 37224, comprises the replicon and β-lactamase gene from plasmid pBR322, the mouse metallothionein promoter positioned to drive expression of a structural gene that encodes a neomycin resistance-conferring enzyme, and about 8 kb of bovine papilloma virus (BPV) DNA. Plasmid pdBPV-MMTneo can be digested with restriction enzyme BamHI to generate two fragments: the ~8 kb fragment that comprises the BPV DNA and an ~7 kb fragment that comprises the other sequences described above. BK virus has only one BamHI restriction site, and plasmids pBKneo1 and pBKneo2 were constructed by ligating the ~7 kb BamHI restriction fragment of plasmid pdBPV-MMTneo to BamHI-linearized BK virus DNA. The construction of plasmids pBKneo1 and pBKneo2, which differ only with respect to the orientation of the BK virus DNA, is described in Example 3, and a restriction site and function map of plasmid pBKneo1 is presented in FIG. 3 of the accompanying drawings.

Figure 4:
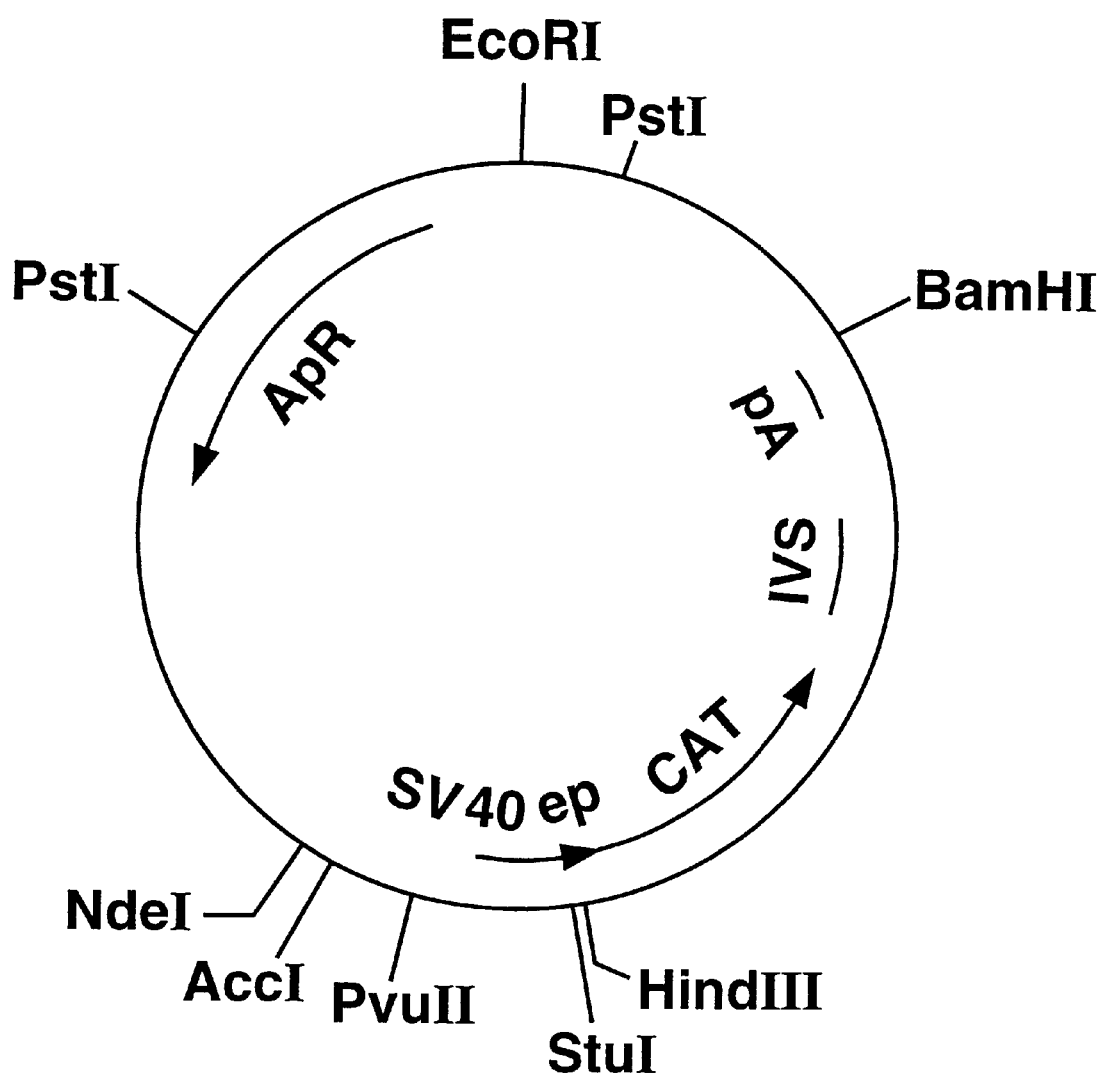
FIG. 4 is a restriction site and function map of plasmid pSV2cat.

Plasmids pBKE1, pBKE2, pBKneo1, and pBKneo2 each comprise the entire genome of the BK virus, including the enhancer sequence, and thus serve as useful starting materials for the expression vectors of the present invention. One such illustrative expression vector, plasmid pBLcat, comprises the BK enhancer sequence in tandem with the human adenovirus-type-2 late promoter positioned to drive expression of the chloramphenicol acetyltransferase enzyme (CAT). Plasmid pSV2cat serves as a convenient source of the CAT gene and can be obtained from the ATCC under the accession number ATCC 37155. A restriction site and function map of plasmid psv2cat is presented in FIG. 4 of the accompanying drawings. Human adenovirus-type-2 DNA is commercially available and can also be obtained from the ATCC under the accession number ATCC VR-2.

Figure 5:
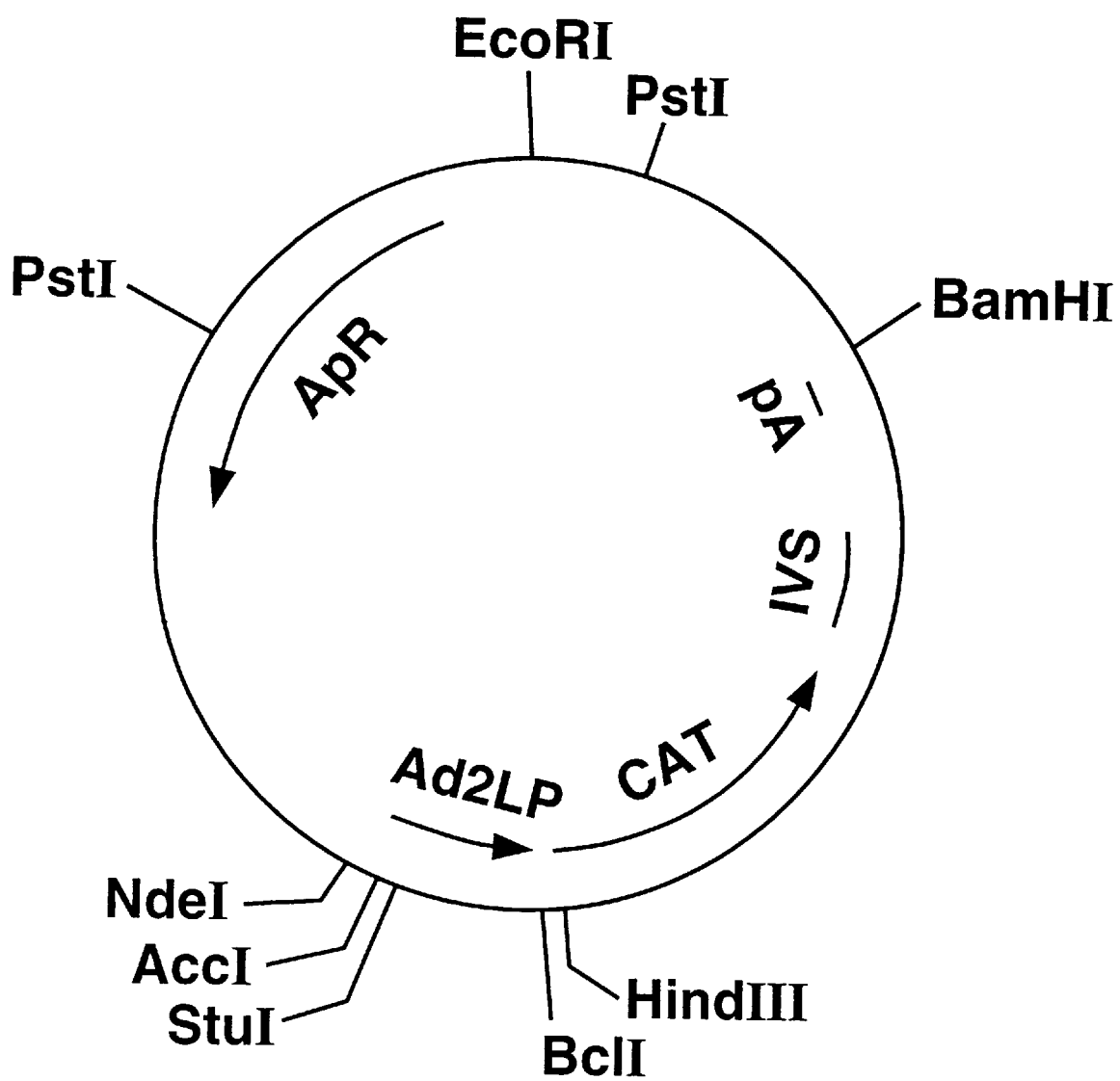
FIG. 5 is a restriction site and function map of plasmid pLPcat.
Figure 6:
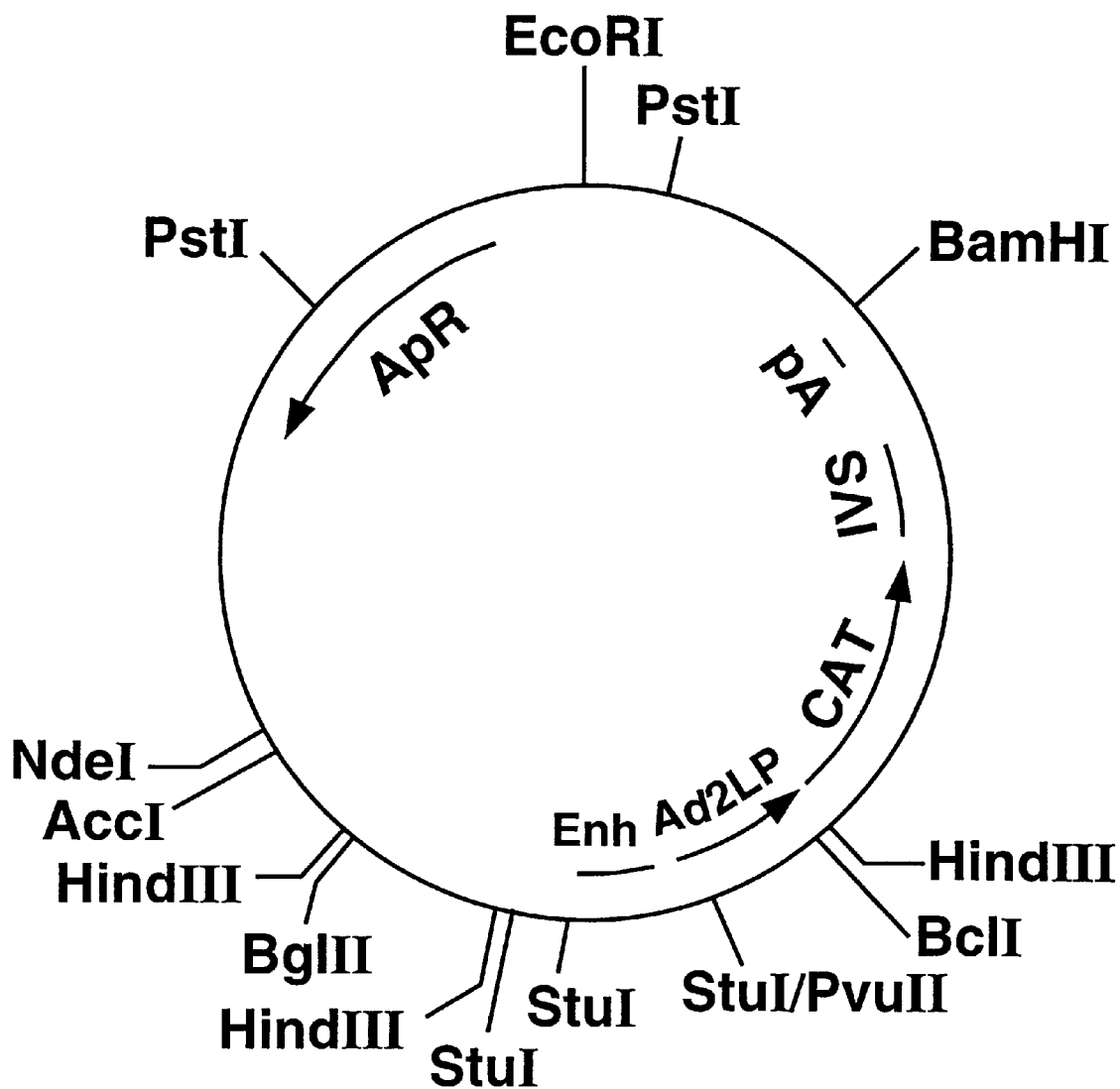
FIG. 6 is a restriction site and function map of plasmid pBLcat.

Illustrative plasmid pBLcat was constructed by ligating the ~0.32 kb late-promoter-containing AccI-PvuII restriction fragment of human adenovirus-type-2 DNA to blunt-ended BclI linkers that attached only to the PvuII end of the AccI-PvuII restriction fragment. The resulting fragment was then ligated to the ~4.51 kb AccI-StuI restriction fragment of plasmid pSV2cat to yield intermediate plasmid pLPcat, for which a restriction site and function map is presented in FIG. 5 of the accompanying drawings. The desired plasmid pBLcat was constructed from plasmid pLPcat by ligating the origin of replication and enhancer-containing, ~1.28 kb AccI-PvuII restriction fragment of BK virus DNA to the ~4.81 kb AccI-StuI restriction fragment of plasmid pLPcat. A restriction site and function map of the resultant plasmid pBLcat is presented in FIG. 6 of the accompanying drawings. The construction of plasmid pBLcat is further described in Example 4.

Figure 7:
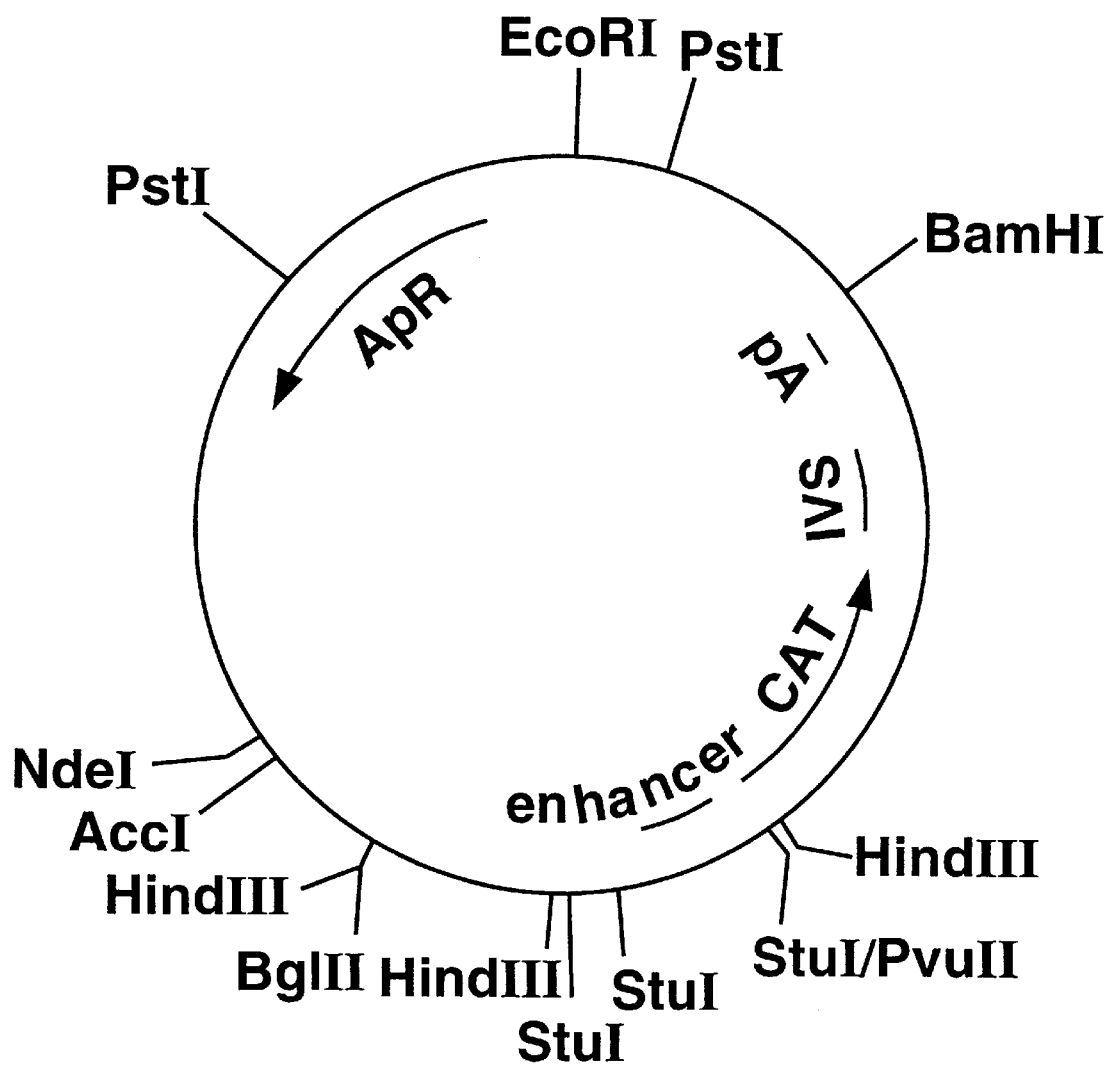
FIG. 7 is a restriction site and function map of plasmid pBKcat.

Plasmid pBKcat is an expression vector that further exemplifies the present invention and utilizes the BK enhancer and BK late promoter to drive expression of chloramphenicol acetyltransferase. Plasmid pBKcat was constructed in a manner analogous to that described for plasmid pLPcat. Thus, the ~4.51 kb AccI-StuI restriction fragment of plasmid pSV2cat was ligated to the ~1.28 kb AccI-PvuII restriction fragment of BK virus such that the BK late promoter is in the correct orientation to drive expression of the CAT gene. A restriction site and function map of plasmid pBKcat is presented in FIG. 7 of the accompanying drawings.

Plasmid pBLcat is a convenient source of the BK enhancer-adenovirus late promoter "cassette" of the present invention. This cassette is an ~870 bp HindIII restriction fragment that can be conveniently inserted into a eukaryotic expression vector to increase expression of a product encoded by that vector. This was done by digesting plasmid pSV2cat with restriction enzyme HindIII and inserting the BK enhancer-adenovirus late promoter cassette. The resultant plasmid, designated as plasmid pSBLcat, contains the SV40 origin of replication, SV40 early promoter, and SV40 enhancer and therefore differs from plasmid pBLcat in which those sequences have been deleted. The tandem SV40 enhancer-BK enhancer-adenovirus major late promoter (SBL promoter) cassette can be excised from plasmid pSBLcat on a PvuII restriction enzyme fragment, which can be conveniently inserted into any recombinant DNA expression vector.

Plasmid pSBLcat drives expression of CAT to higher levels than does plasmid pBLcat, so long as no E1A gene product is present. This increased expression in the absence of EIA gene product indicates that the two enhancers, one from SV40 and the other from BK, have an additive, enhancing effect on transcription from nearby promoters. To assess the strength and utility of the SBL promoter, the chloramphenicol acetyltransferase (CAT) expression vector, pSBL-CAT, was transfected vector into a variety of mammalian host cells, and the level of CAT activity was measured 48 to 72 hours later as described by Gorman, et al., 1982, Mol. Cell. Biol. 2:1044–1051. The level of CAT activity obtained from pSV2-CAT, in which the CAT gene is driven by the strong SV40 early promoter, was used for comparative purposes. The SBL promoter was 3 to 6 fold stronger than the SV40 early promoter in the following cell lines: BHK-21, HeLa; MK2, COS-1, 293, CHO (all available from the American Type Culture collection), P3UCLA (Varki et al., 1984, Cancer Res. 44:681–687), K816 (Grinnell et al., 1986, Mol. Cell. Biol. 6:3596–3605), and an adenovirus-transformed Syrian hamster tumor line, AV12, described below. In primary human embryonic kidney cells and liver cells, CAT activity was detected after transfection with PSBL-CAT, but not with pSV2-CAT. Although efficient expression from the MLP could be obtained with either the BK (pBL-CAT) or SV40 enhancer (pSL-CAT, a plasmid that is analogous to plasmid pSV2-CAT, except that the SV40 early promoter is replaced with the adenovirus 2 major late promoter, described by Grinnell et al., 1986, Mol. Cell. Biol. 6:3596–3605), these single enhancer constructions did not function efficiently in all cells. For example, pSV2-CAT was 3 fold stronger than PSL-CAT in 293 cells and 10 fold stronger than pBL-CAT in HeLa cells. Thus, the use of tandem enhancer sequences upstream of a eukaryotic promoter results in a strong and versatile promoter that displays little host cell dependence, and therefore can be used for the efficient expression of genes in a wide variety of mammalian cells.

Figure 8:
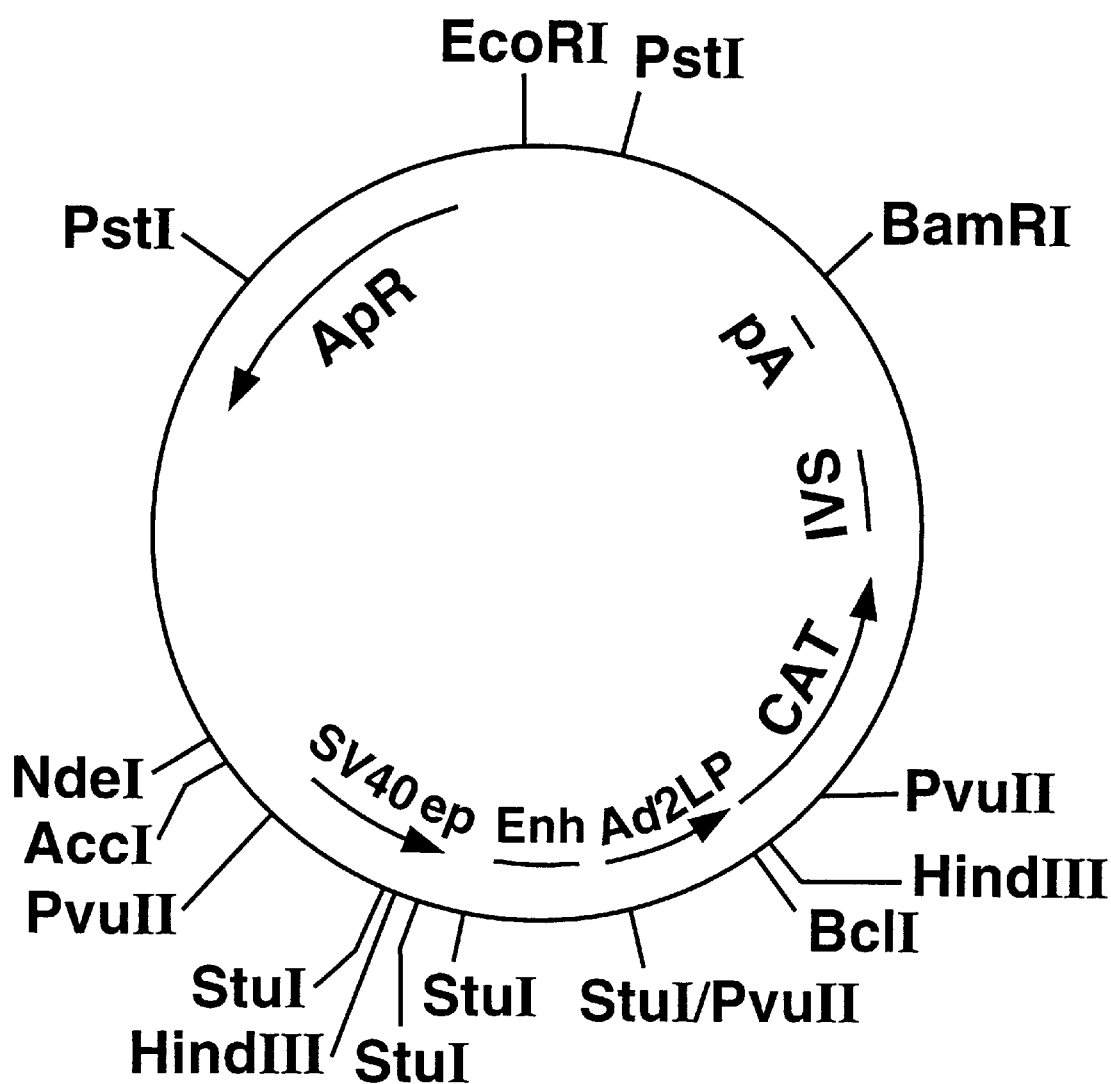
FIG. 8 is a restriction site and function map of plasmid pSBLcat.

However, in the presence of E1A gene product, plasmid pBLcat drives expression of CAT to higher levels than does plasmid pSBLcat, presumably because the SV40 enhancer is inhibited by the E1A gene product. Conversely, in HeLa cells, the SV40 enhancer stimulated transcription from the adenovirus 2 major late promoter (Ad2MLP) 26 fold, but the BK enhancer only stimulated transcription from Ad2MLP 1.5 fold in HeLa cells. Because the basal level of BK activity in HeLa cells is so low, stimulation of that activity with the immediate-early gene product of a large DNA virus, such as E1A protein, still does not result in optimal expression levels. This low level activity of the BK enhancer in HeLa cells is thought to be due to a repressor activity present in HeLa cells that interacts with the BK enhancer. This repressor activity in HeLa cells can be titrated out by introducing more copies of the BK enhancer into the HeLa cell. In fact, in the HeLa cell line, E1A may increase the level of the repressor. However, optimal expression levels can be obtained in HeLa cells using the tandem SV40 enhancer BK enhancer of the invention. This tandem enhancer thus has the advantage of avoiding cell-specific negative interactions that may be encountered, as in HeLa cells, in some host cells. A restriction site and function map of plasmid pSBLcat is presented in FIG. 8 of the accompanying drawings, and the construction of plasmid pSBLcat is described in Example 5.

Figure 9:
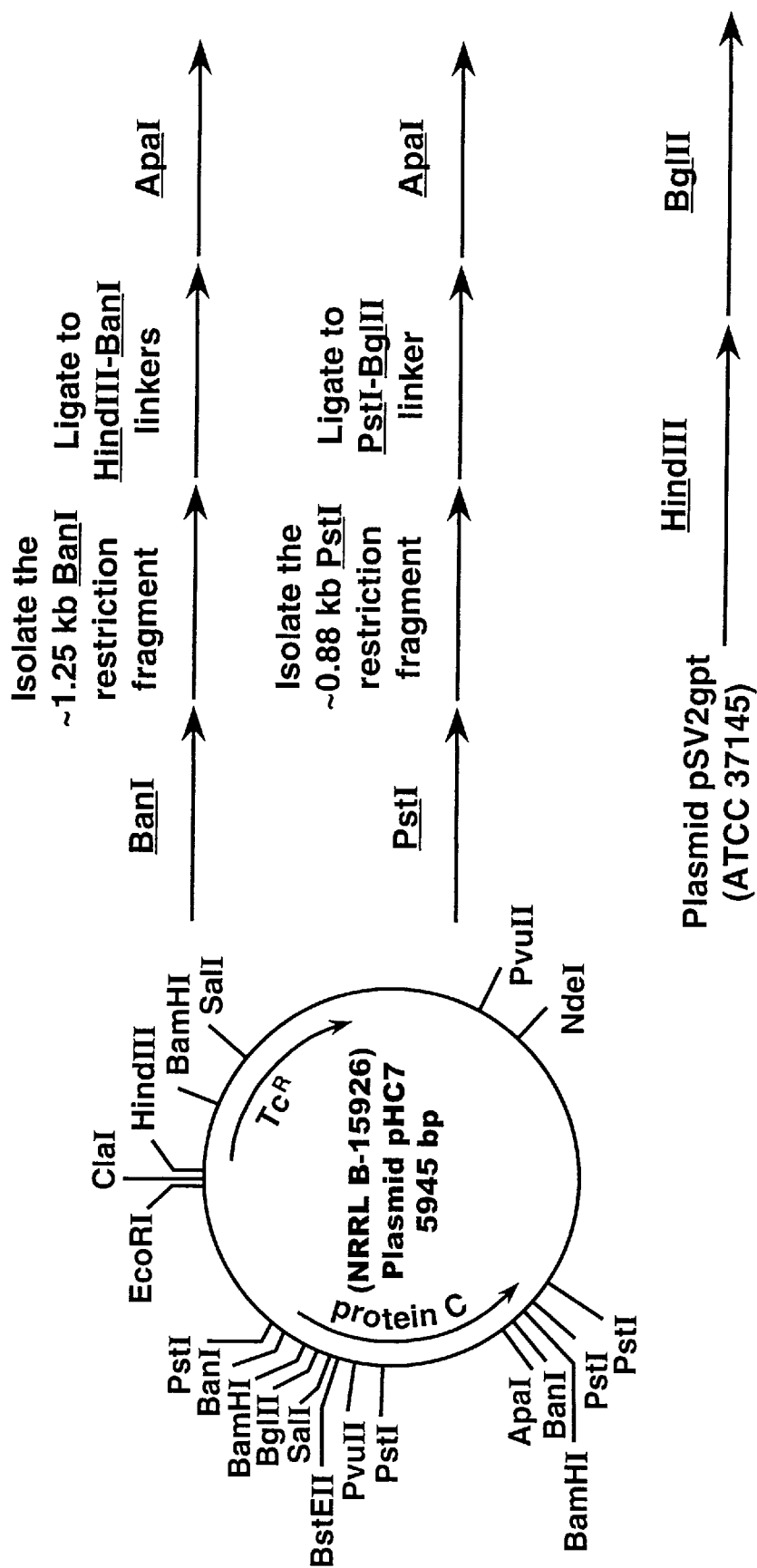
FIGS. 9A–9D depict the construction and presents a restriction site and function map of plasmid pL133.
Figure 9:
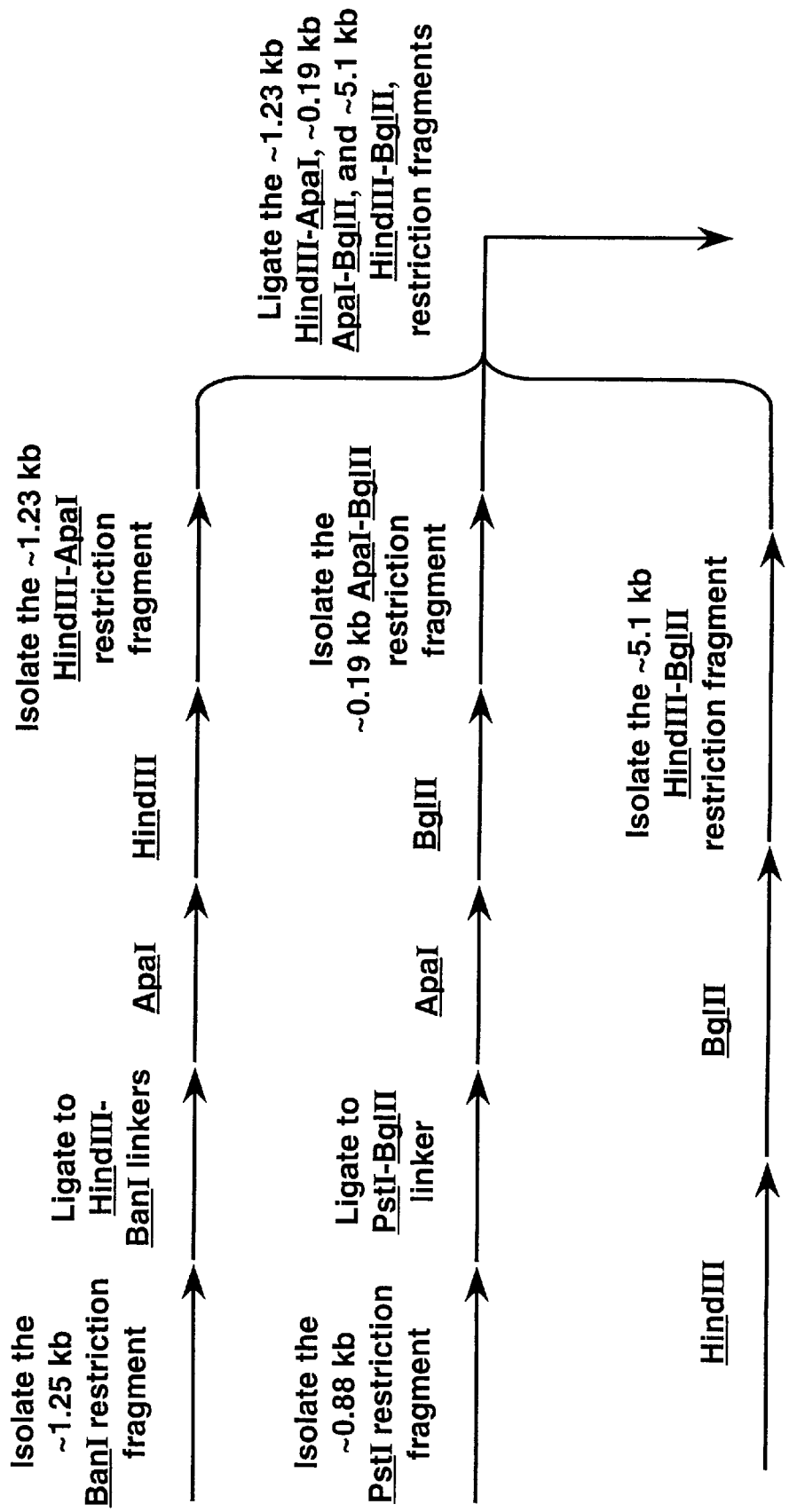
Figure 9:
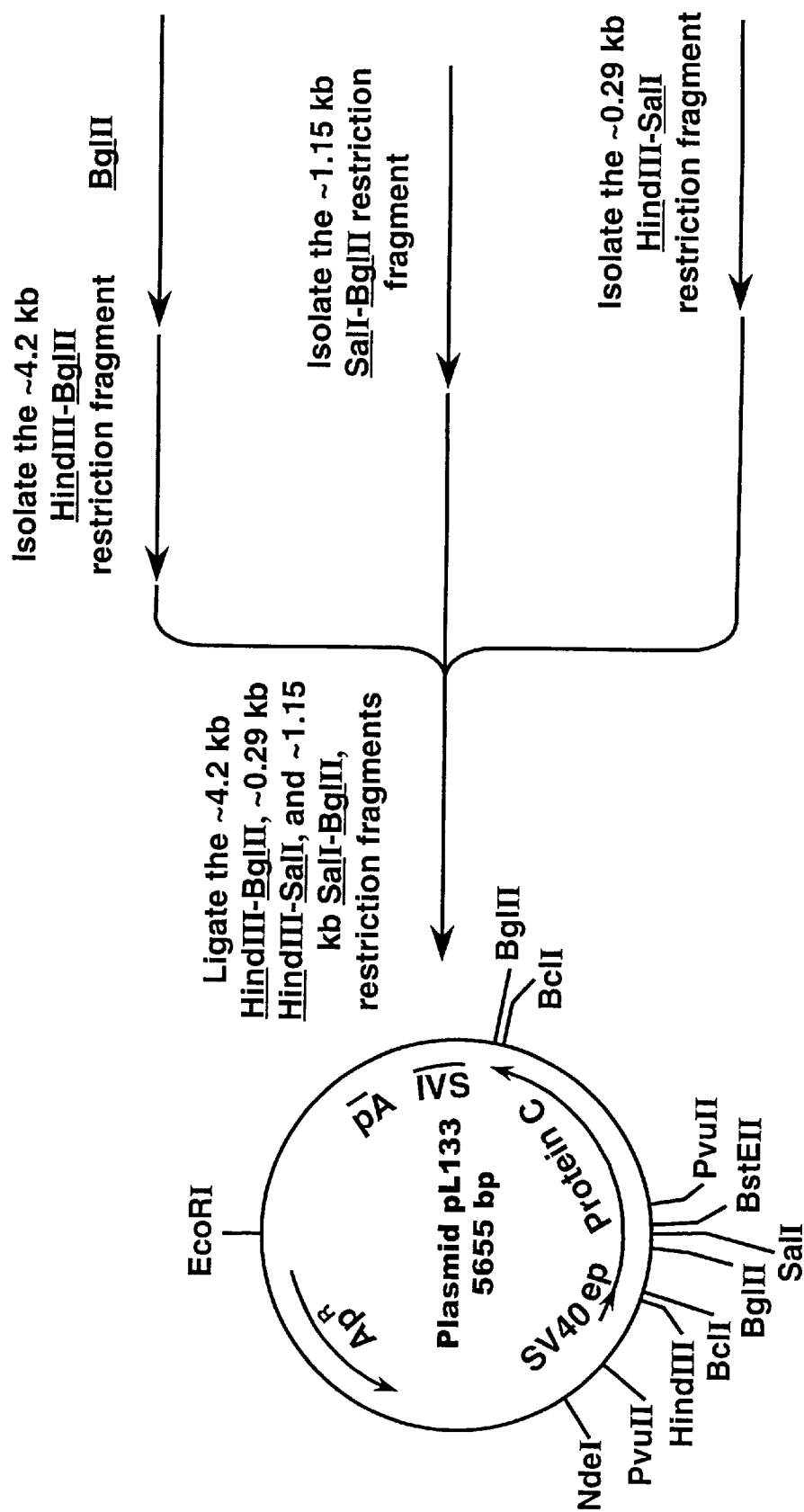
Figure 9:
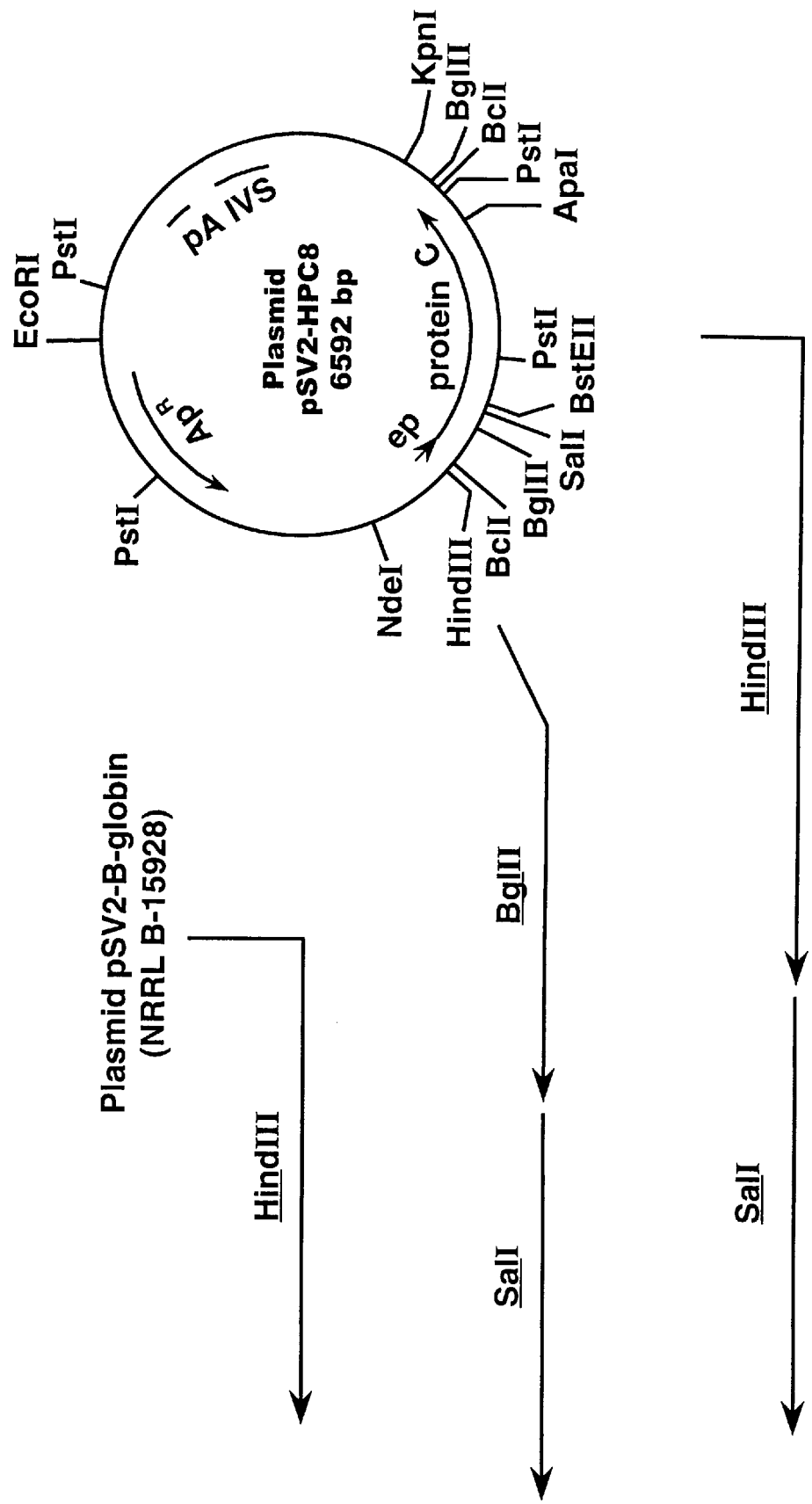
Figure 10:
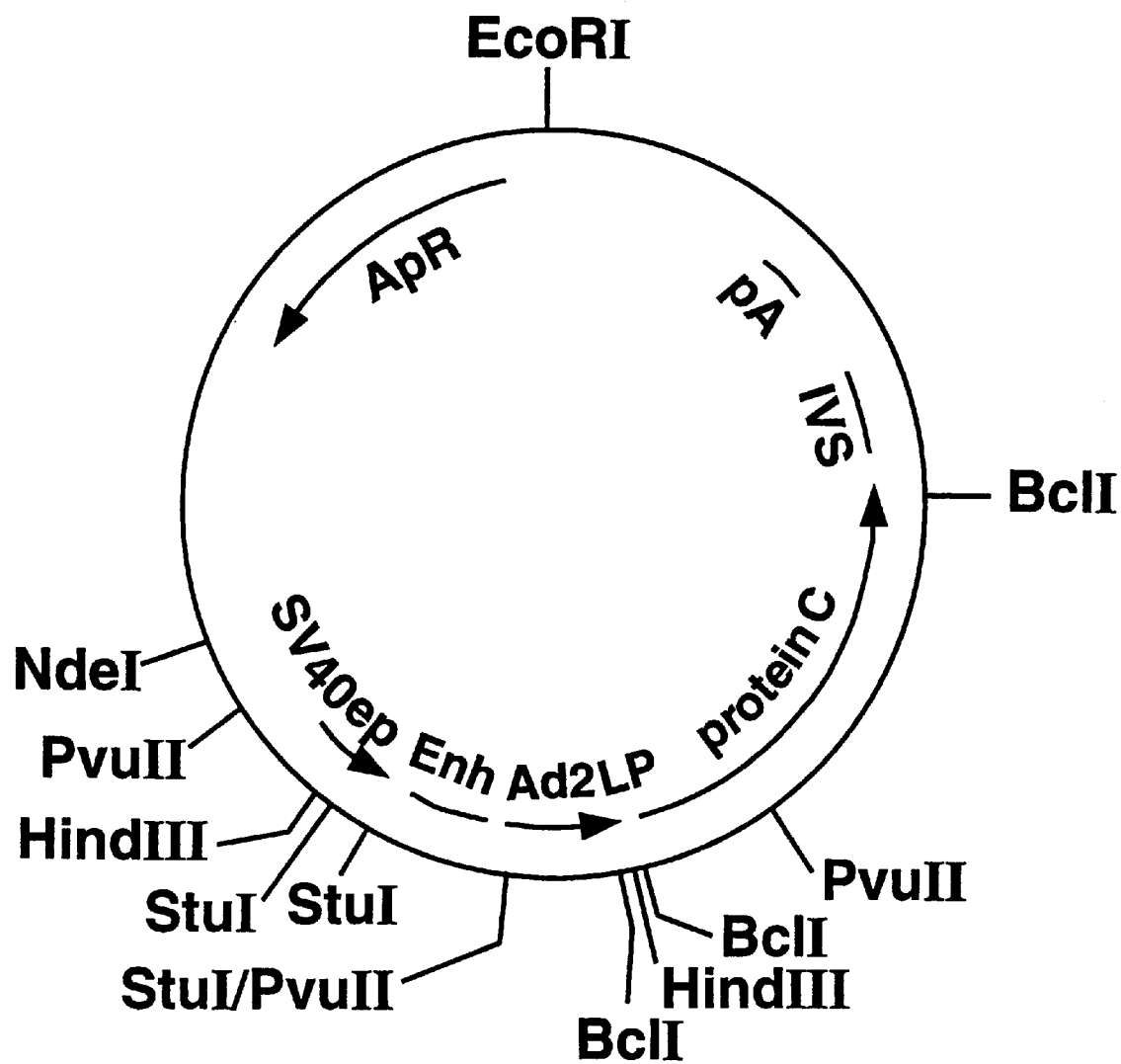
FIG. 10 is a restriction site and function map of plasmid pLPC.

The BK enhancer-adenovirus late promoter cassette has also been used to improve expression of human protein C. This was done by ligating the cassette into plasmid pL133, a plasmid disclosed and claimed in U.S. patent application Ser. No. 699,967, filed Feb. 8, 1985, incorporated herein by reference. A restriction site and function map of plasmid pL133 is presented in FIG. 9 of the accompanying drawings. Plasmid pL133, the construction of which is given in Example 6, was digested with restriction enzyme HindIII and then ligated to the ~0.87 kb HindIII restriction fragment of plasmid pBLcat to yield plasmid pLPC. A restriction site and function map of plasmid pLPC is presented in FIG. 10 of the accompanying drawings, and the construction of plasmid pLPC is further described in Example 7.

Plasmid pLPC, like plasmid pL133, comprises the enhancer, early and late promoters, T-antigen-binding sites, and origin of replication of SV40. Thus, use of plasmid pLPC and derivatives thereof in any recombinant host cells is illustrative of the tandem enhancer expression method of the invention. Plasmid pLPC served as a useful starting material for many vectors of the invention, including plasmid PSBL. Plasmid pSBL was constructed by deleting the protein C-encoding DNA on plasmid pLPC. This deletion merely requires excision of plasmid pLPC's single BclI restriction fragment by digestion with BclI and self-ligation. The resulting plasmid pSBL serves as a convenient expression vector for use in the tandem enhancer method of the invention, for coding sequences of interest can be readily inserted at the sole remaining BclI site.

The SV40 elements present on plasmid PLPC are situated closely together and difficult to delineate. The binding of T antigen to the T-antigen-binding sites, which is necessary for SV40 replication, is known to enhance transcription from the SV40 late promoter and surprisingly has a similar effect on the BK late promoter. Because the high level of T-antigen-driven replication of a plasmid that comprises the SV40 origin of replication is generally lethal to the host cell, neither plasmid pLPC nor plasmid pL133 are stably maintained as episomal (extrachromosomal) elements in the presence of SV40 T antigen, but rather, the two plasmids must integrate into the chromosomal DNA of the host cell to be stably maintained.

Figure 11:
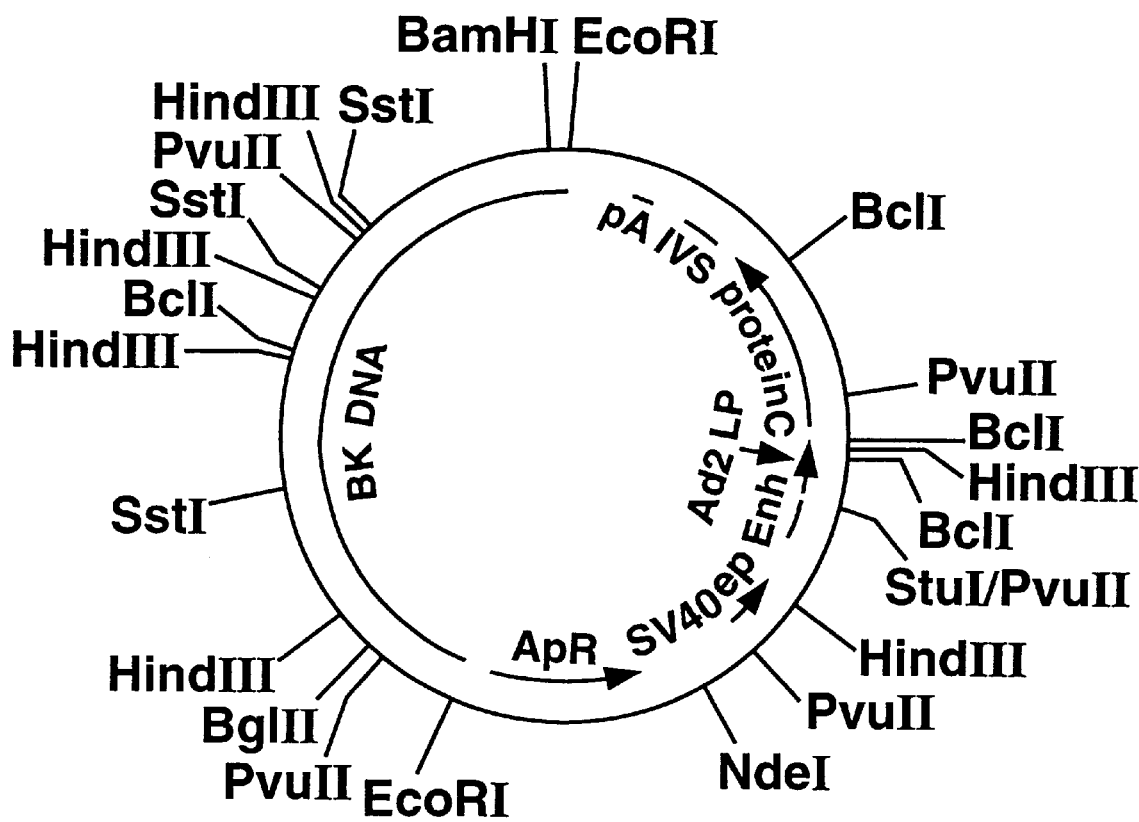
FIG. 11 is a restriction site and function map of plasmid pLPC4.

The overall structure of the BK enhancer region is quite similar to that of SV40, for the BK enhancer, origin of replication, early and late promoters, and the BK analogue of the T-antigen-binding sites are all closely situated and difficult to delineate on the BK viral DNA. However, when grown in the presence of BK T antigen, a plasmid that comprises the BK origin of replication and T-antigen-binding sites does not replicate to an extent that proves lethal and is stably maintained as an episomal element in the host cell. In addition, the T-antigen-driven replication can be used to increase the copy number of a vector comprising the BK origin of replication so that when selective pressure is applied more copies of the plasmid integrate into the host cell's chromosomal DNA. Apparently due to the similar structure-function relationships between the BK and SV40 T antigens and their respective binding sites, BK replication is also stimulated by SV40 T antigen. To construct a derivative of plasmid PLPC that can exist as a stably-maintained element in a transformed eukaryotic cell, the entire BK genome, as an EcoRI-linearized restriction fragment, was inserted into the single EcoRI restriction site of plasmid pLPC. This insertion produced two plasmids, designated pLPC4 and pLPC5, which differ only with respect to the orientation of the BK EcoRI fragment. A restriction site and function map of plasmid pLPC4 is presented in FIG. 11 of the accompanying drawings, and the construction of plasmids pLPC4 and pLPC5 is further described in Example 8.

Episomal maintenance of a recombinant DNA expression vector is not always preferred over integration into the host cell chromosome. However, due to the absence of a selectable marker that functions in eukaryotic cells, the identification of stable, eukaryotic transformants of plasmid pLPC is difficult, unless plasmid pLPC is cotransformed with another plasmid that does comprise a selectable marker. Consequently, plasmid pLPC has been modified to produce derivative plasmids that are selectable in eukaryotic host cells.

Figure 12:
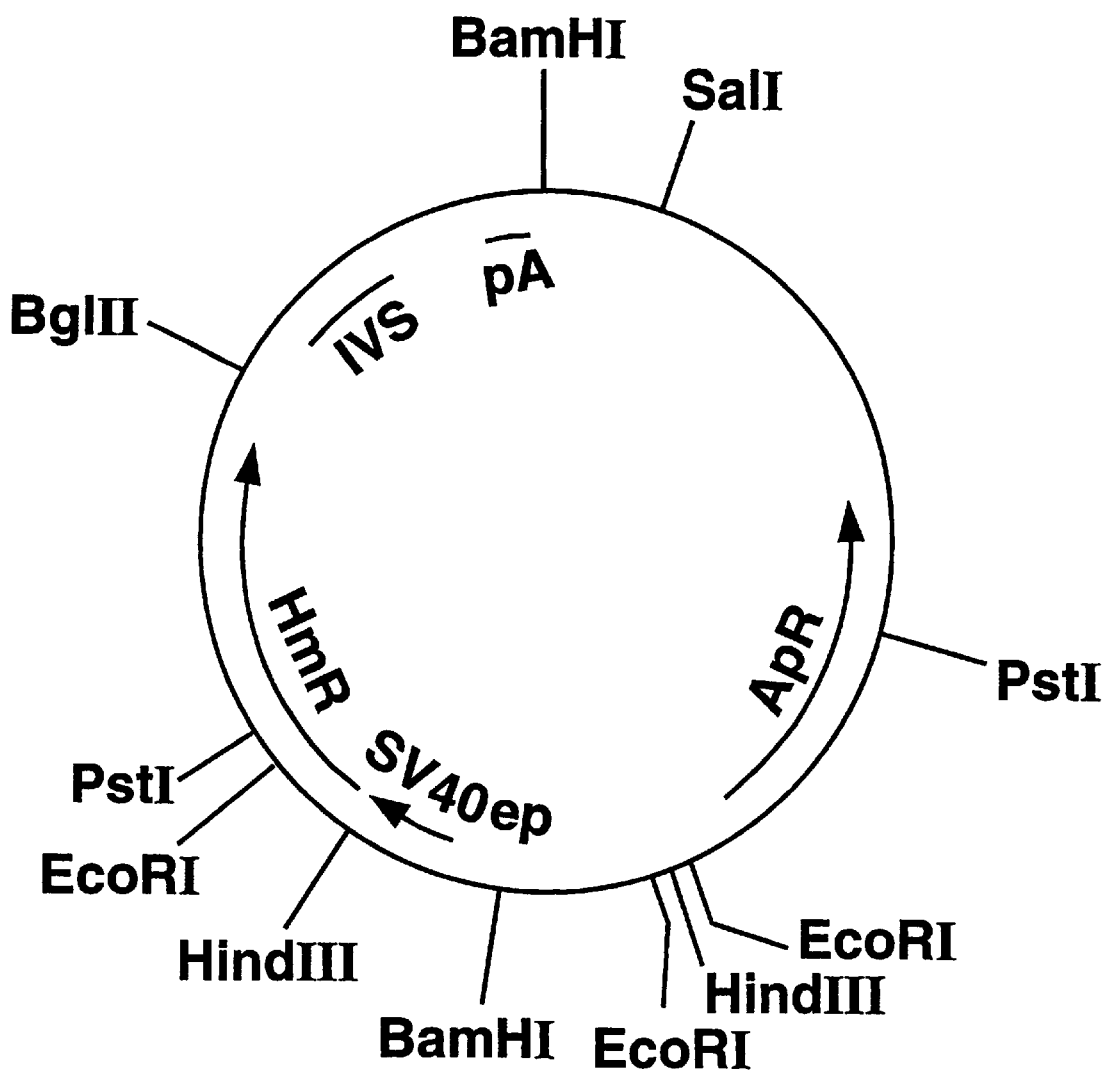
FIG. 12 is a restriction site and function map of plasmid pSV2hyg.
Figure 13:
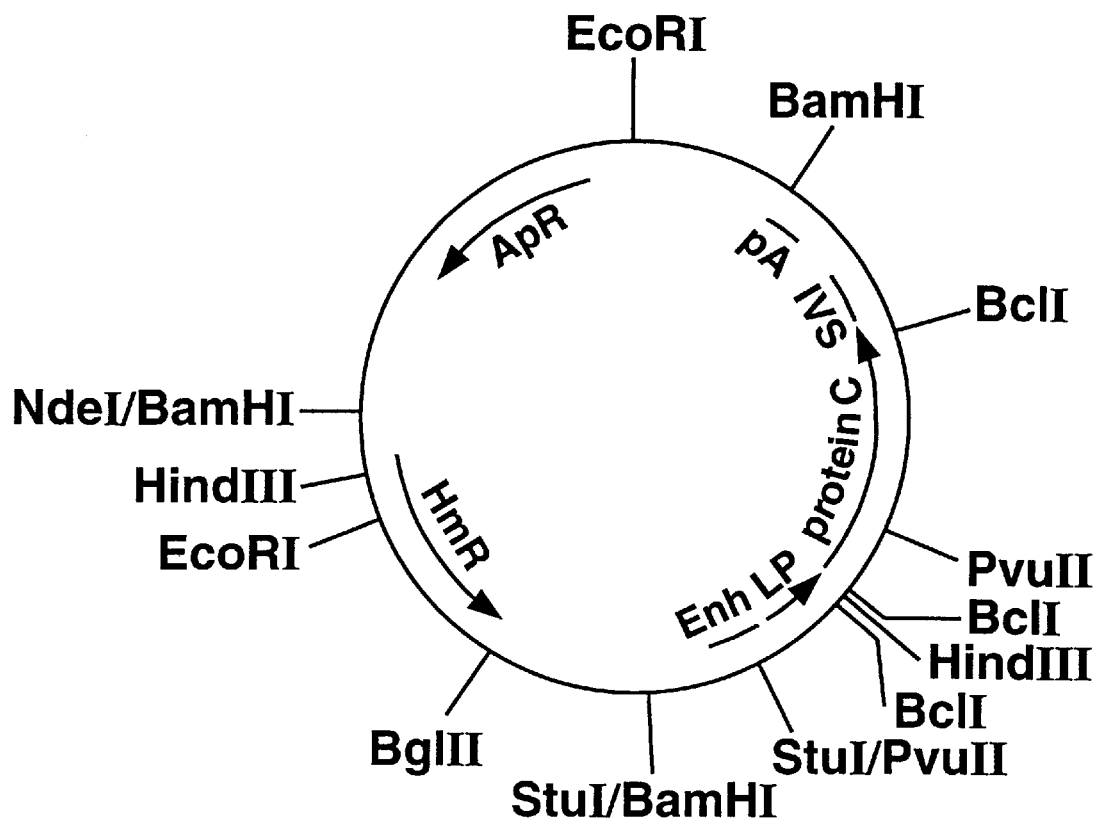
FIG. 13 is a restriction site and function map of plasmid pLPChyg1.

This was done by ligating plasmid pLPC to a portion of plasmid pSV2hyg, a plasmid that comprises a hygromycin resistance-conferring gene. A restriction site and function map of plasmid pSV2hyg, which can be obtained from the Northern Regional Research Laboratory (NRRL), Peoria, Ill. 61640, under the accession number NRRL B-18039, is presented in FIG. 12 of the accompanying drawings. Plasmid pSV2hyg was digested with restriction enzyme BamHI, and the ~2.5 kb BamHI restriction fragment, which comprises the entire hygromycin resistance-conferring gene, was isolated, treated with Klenow enzyme (the large fragment produced upon subtilisin cleavage of *E. coli* DNA polymerase I), and then ligated to the Klenow-treated, ~5.82 kb NdeI-StuI restriction fragment of plasmid pLPC to yield plasmids pLPChyg1 and pLPChyg2. Plasmids pLPChyg1 and pLPChyg2 differ only with respect to the orientation of the hygromycin resistance-conferring fragment. A restriction site and function map of plasmid pLPChyg1 is presented in FIG. 13 of the accompanying drawings, and the construction protocol for plasmids pLPChyg1 and pLPChyg2 is described in Example 9.

Plasmids pLPChyg1 and pLPChyg2 can be readily modified to contain the BK virus genome. As stated above, expression of BK T-antigen in a host cell containing a plasmid comprising the BK T-antigen binding sites increases the copy number of the plasmid. If the plasmid also comprises a selectable marker, selection after T-antigen stimulated replication will result in integration of more copies of the plasmid into the host's genomic DNA than would occur in the absence of T-antigen stimulated replication. Plasmids pLPChyg1 and pLPChyg2 each comprise two EcoRI sites, one in the HmR gene and the other in the pBR322-derived sequences of the plasmid. Plasmid pLPChyg1 was partially digested with EcoRI to obtain cleavage only at the pBR322-derived EcoRI site and then ligated with EcoRI-digested BK virus DNA to yield plasmids pLPChT1 and pLPChT2, which differ only with respect to the orientation of the BK virus DNA. Plasmids pLPChT1 and pLPChT2 are useful derivatives of plasmid pLPChyg1 (and analogous constructions can be made using plasmid pLPChyg2 as starting material instead of pLPChyg1) for purposes of integrating high numbers of copies of a protein C expression vector into the genome of a eukaryotic host cell.

Human protein C expression plasmids similar to plasmids pLPChyg1 and pLPChyg2 containing the dihydrofolate reductase (dhfr) gene were constructed by inserting the dhfr gene-containing, Klenow-treated ~1.9 kb BamHI restriction fragment of plasmid pBW32 into the ~5.82 kb NdeI-StuI restriction fragment of plasmid pLPC. The resulting plasmids, designated as pLPCdhfr1 and pLPCdhfr2, differ only with respect to the orientation of the dhfr gene. The construction of these plasmids is described in Example 11B.

Figure 14:
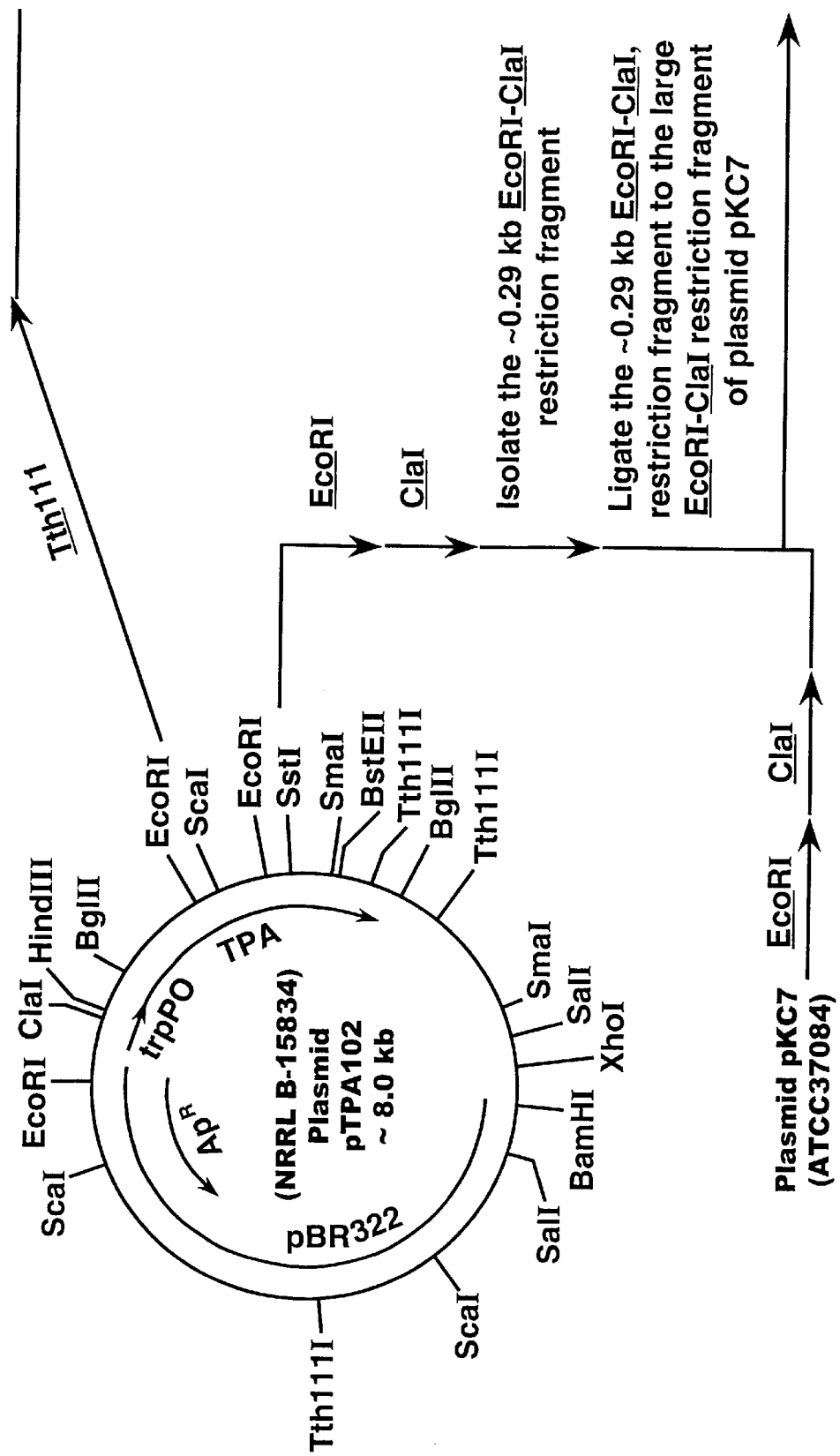
FIGS. 14A–14P depict the construction and presents a restriction site and function map of plasmid pBW32.
Figure 14:
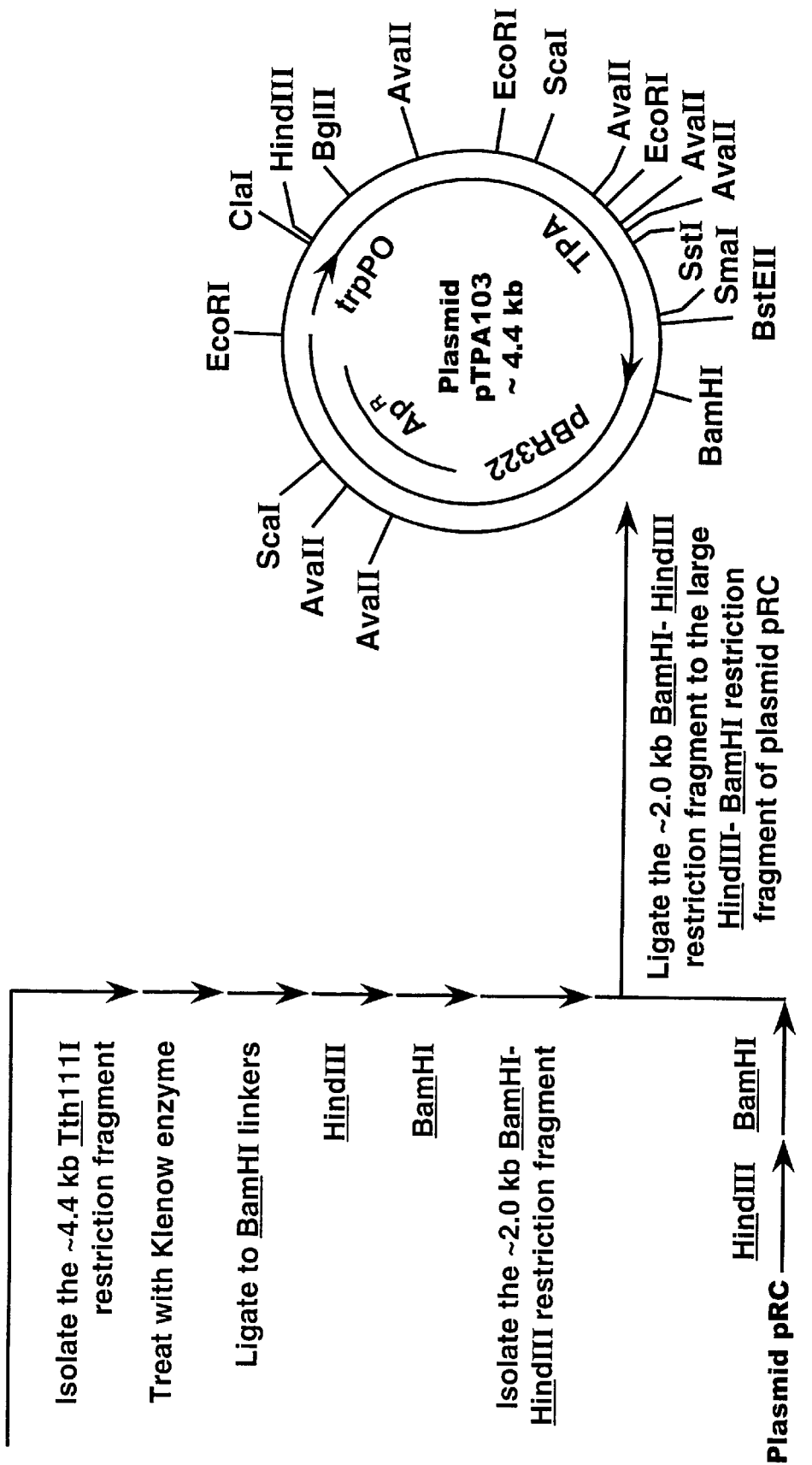
Figure 14:
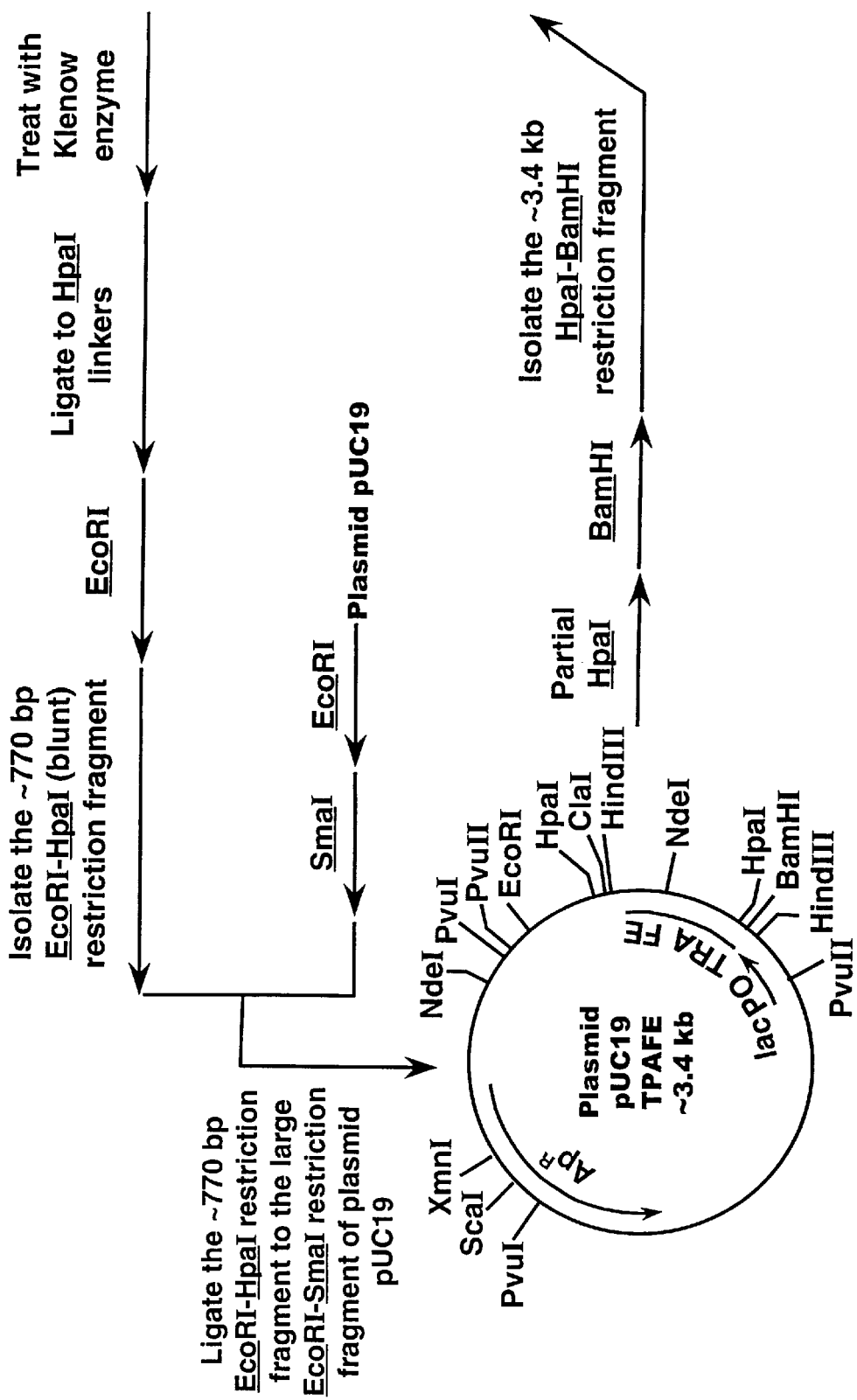
Figure 14:
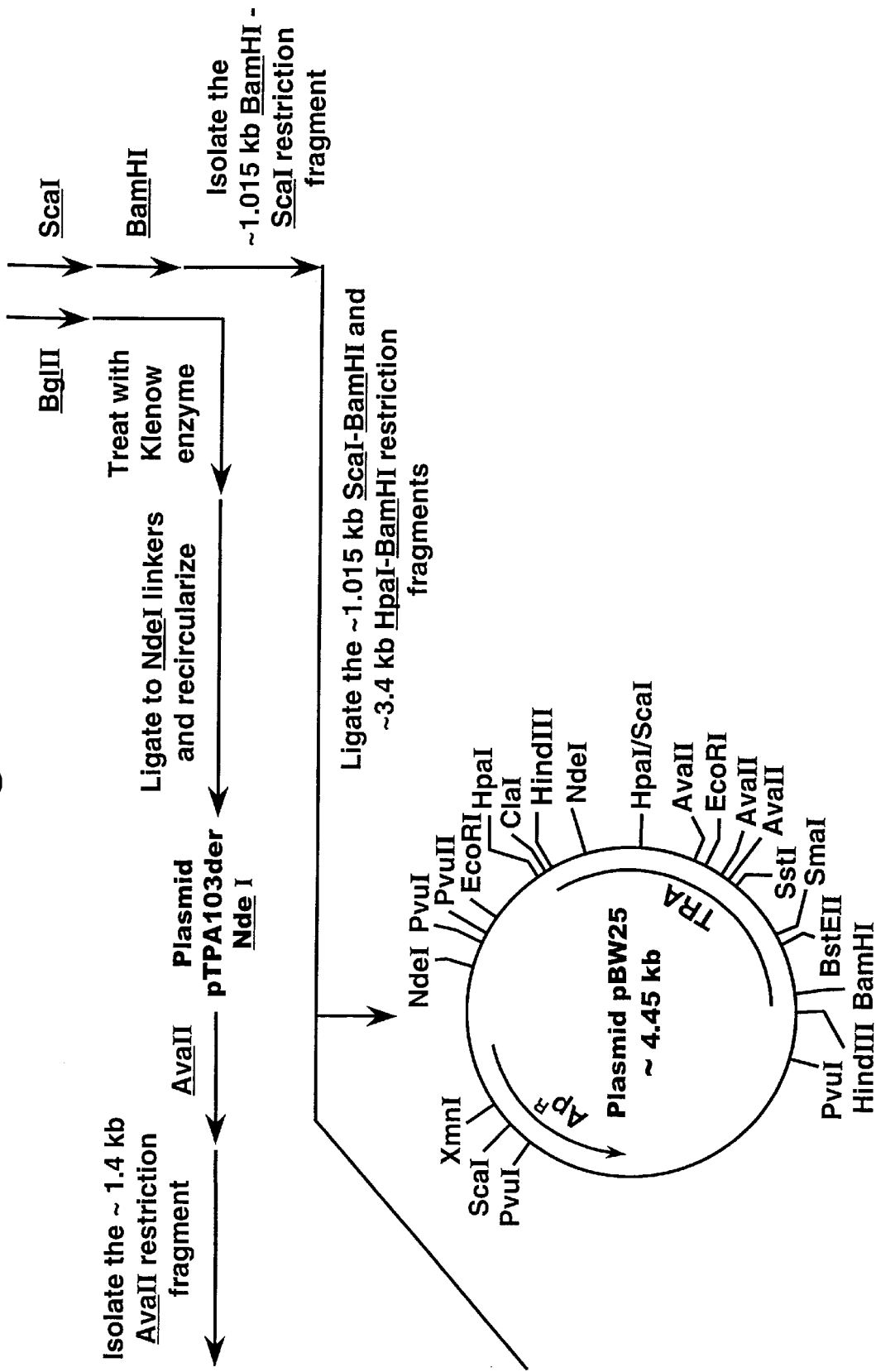
Figure 14:
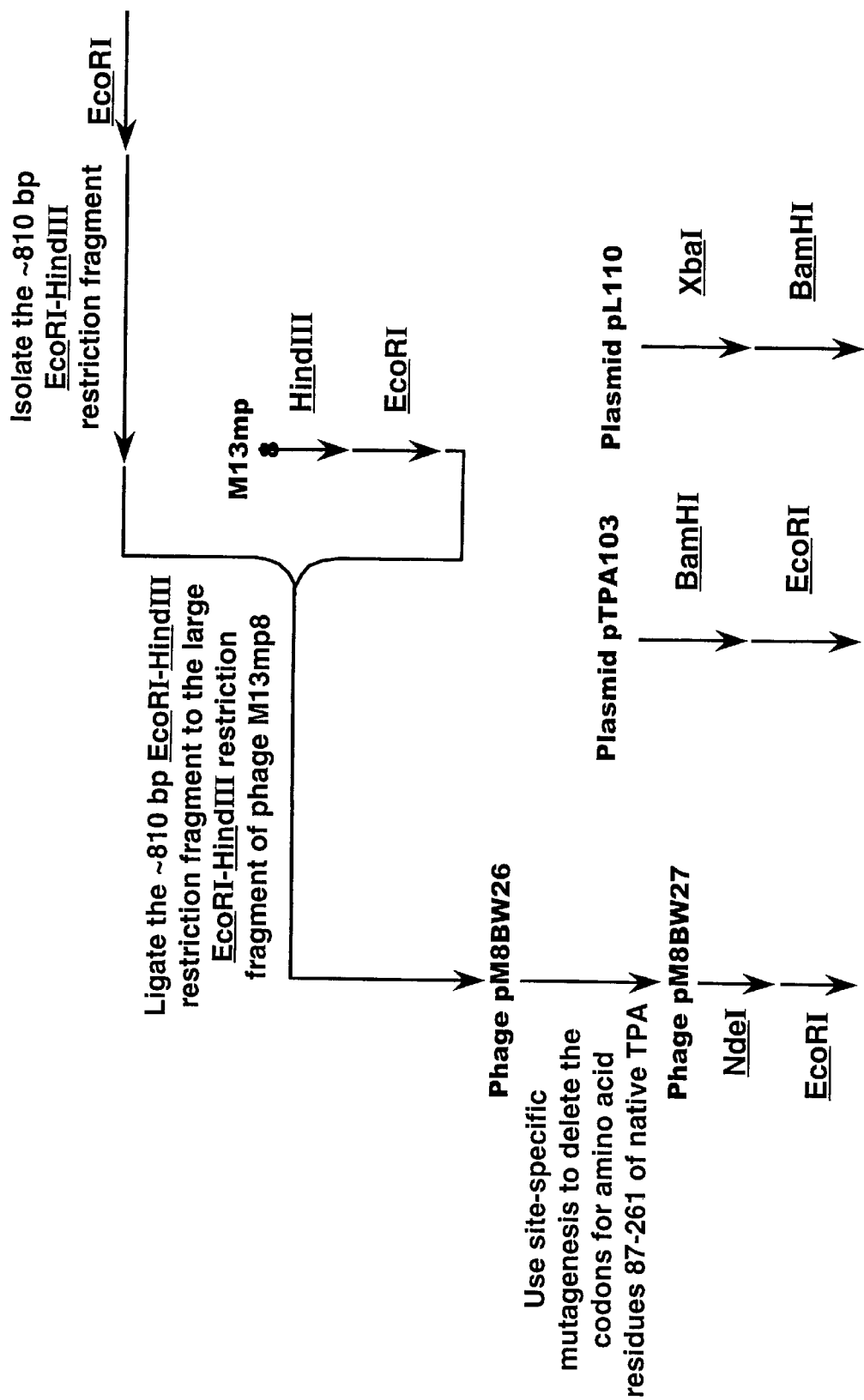
Figure 14:
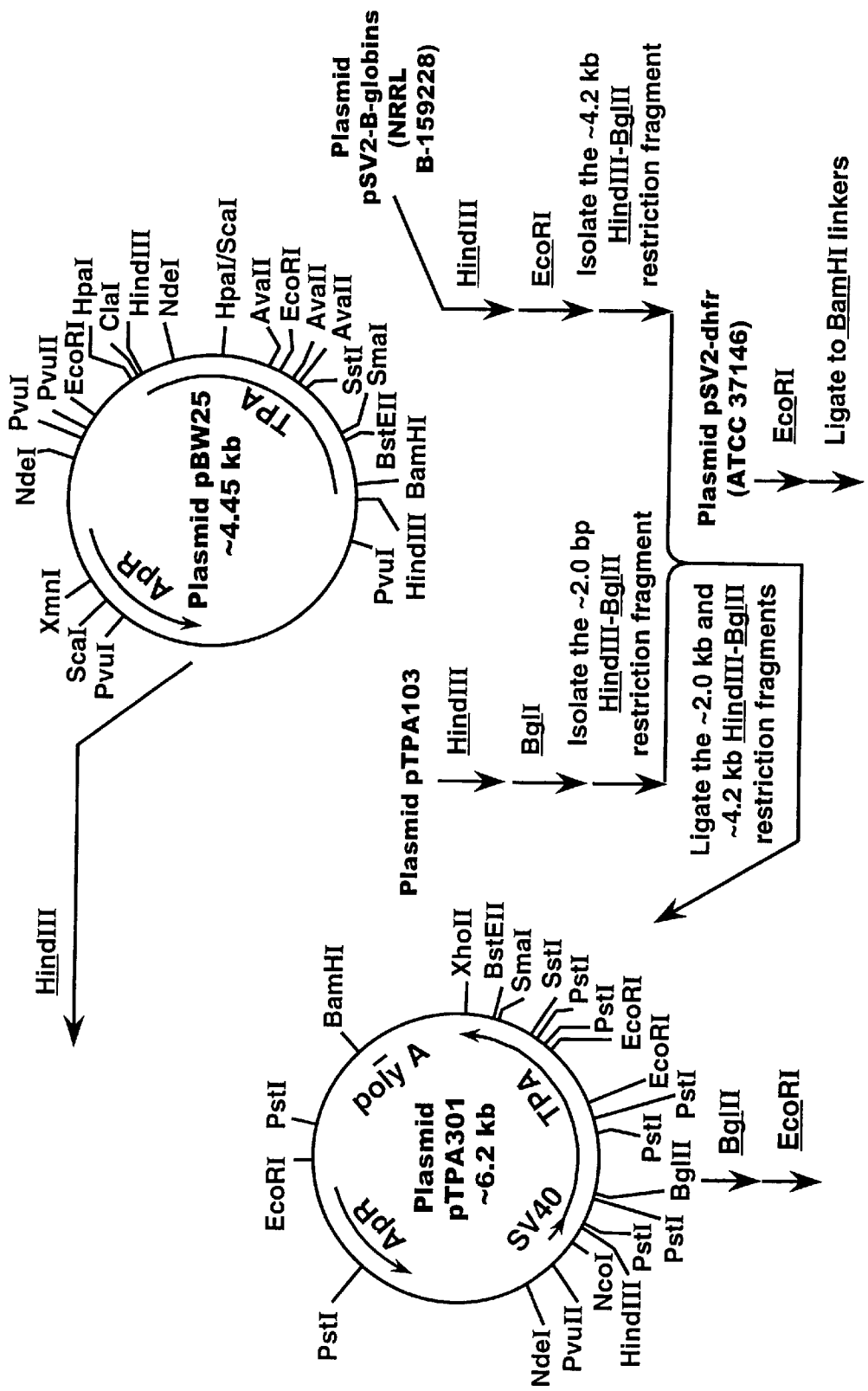
Figure 14:
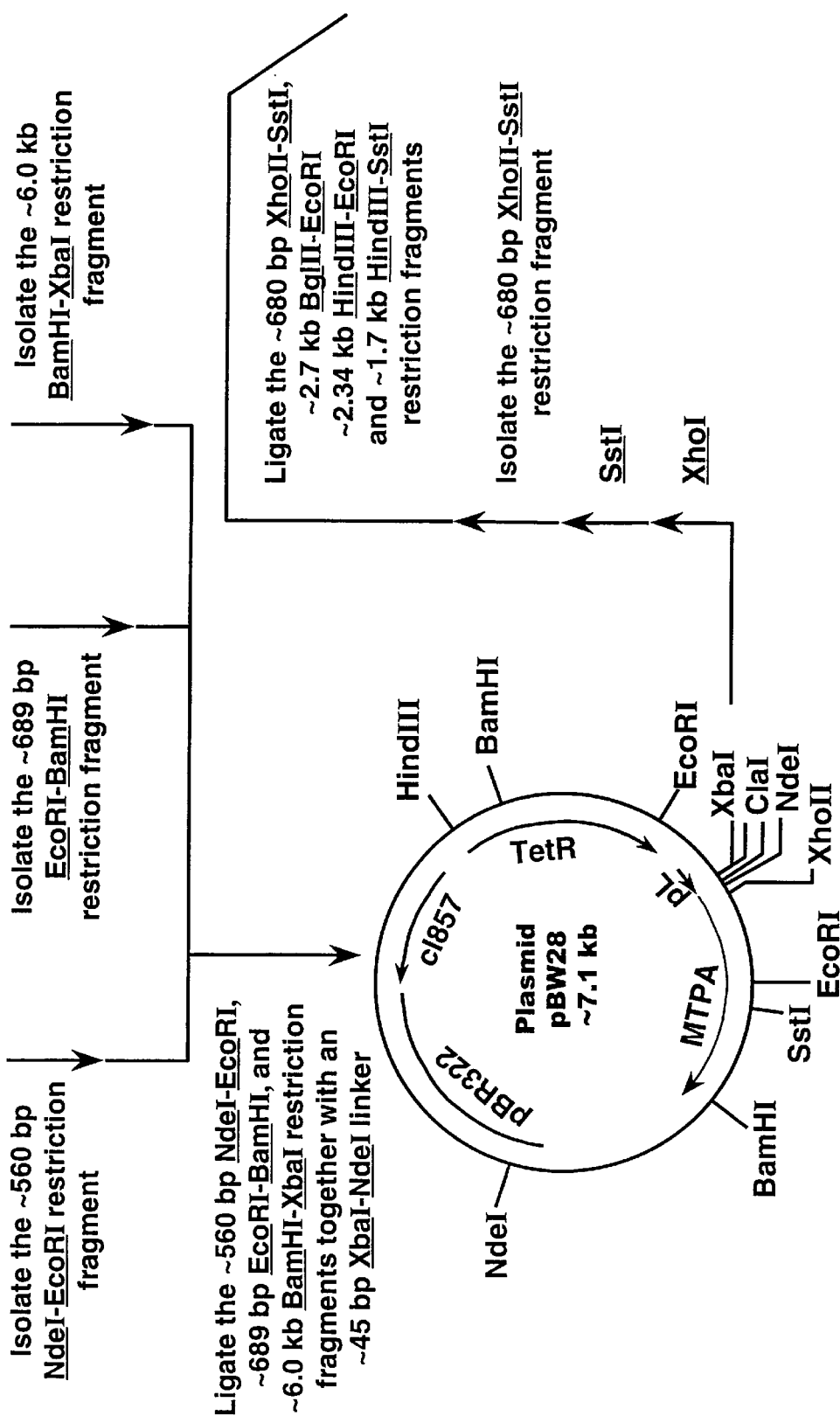
Figure 14:
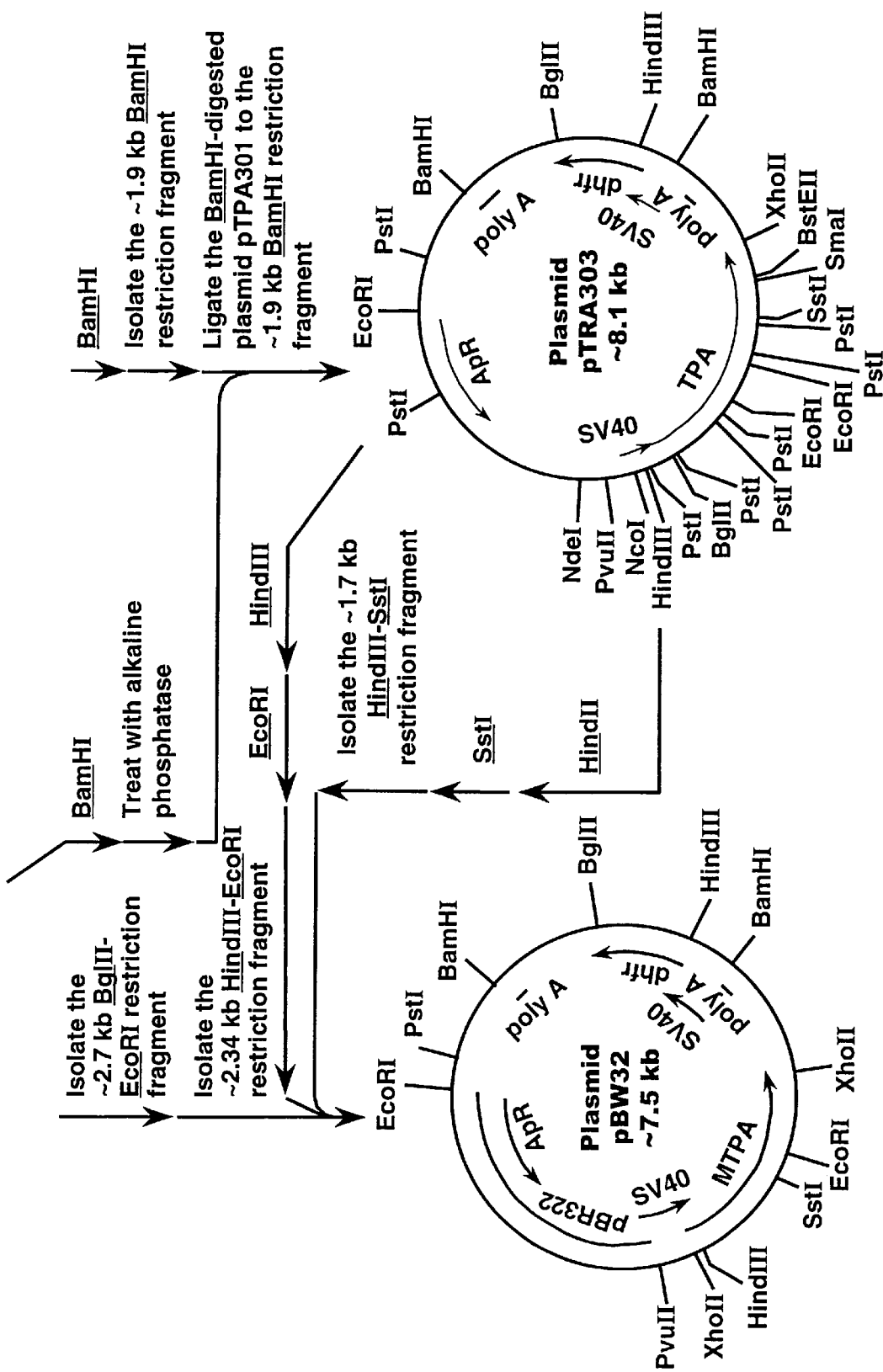
Figure 14:
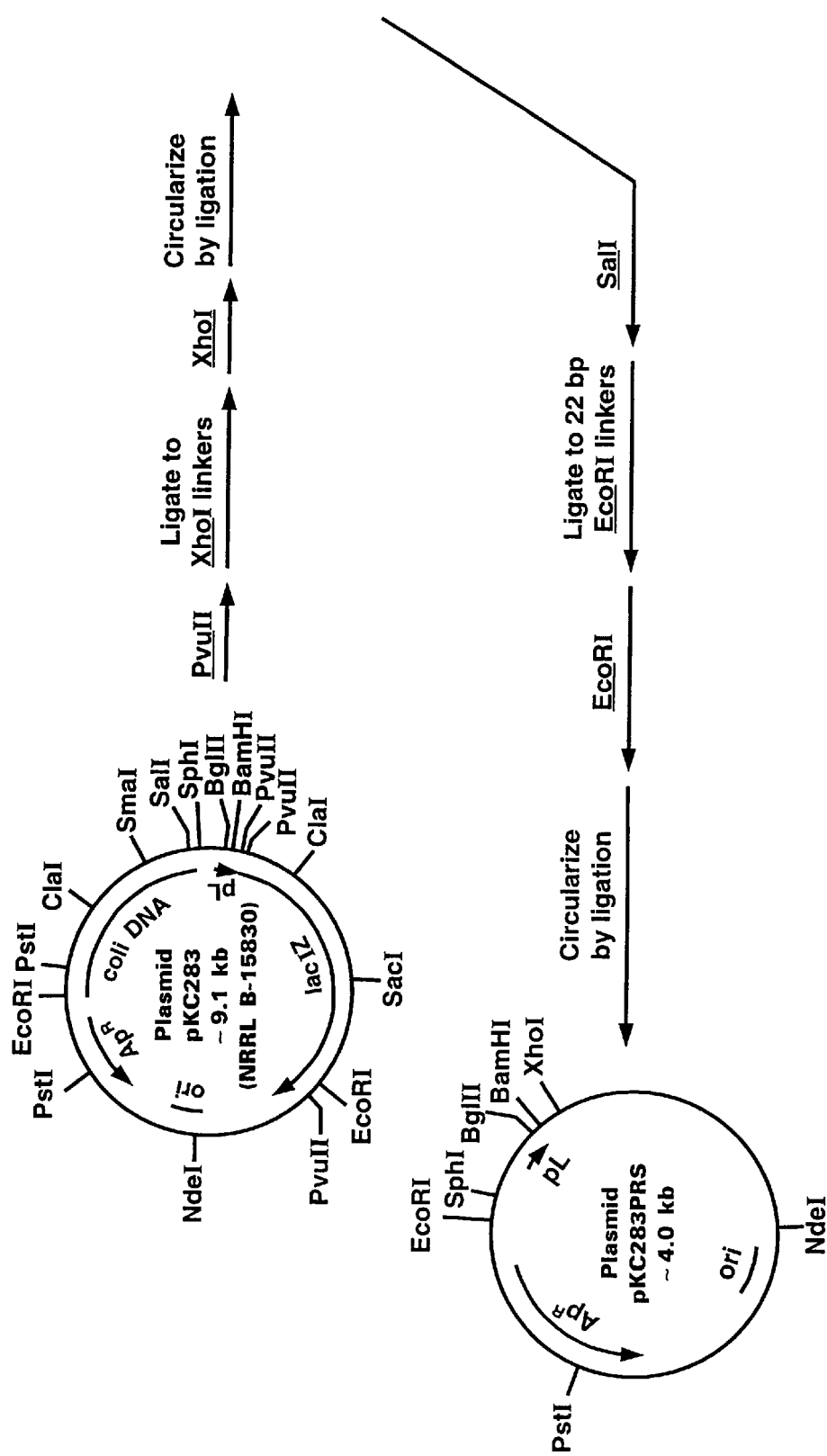
Figure 14:
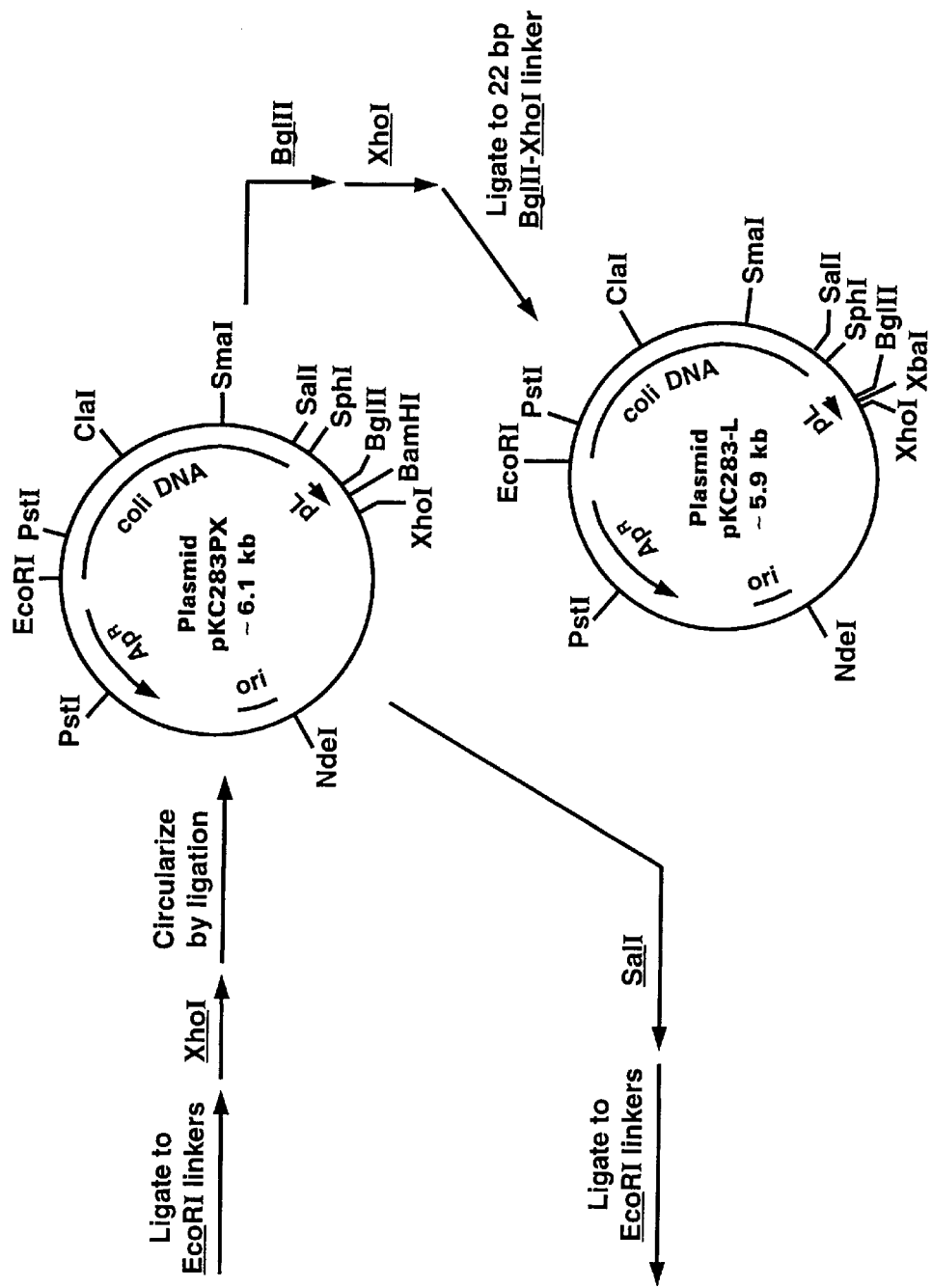
Figure 14:
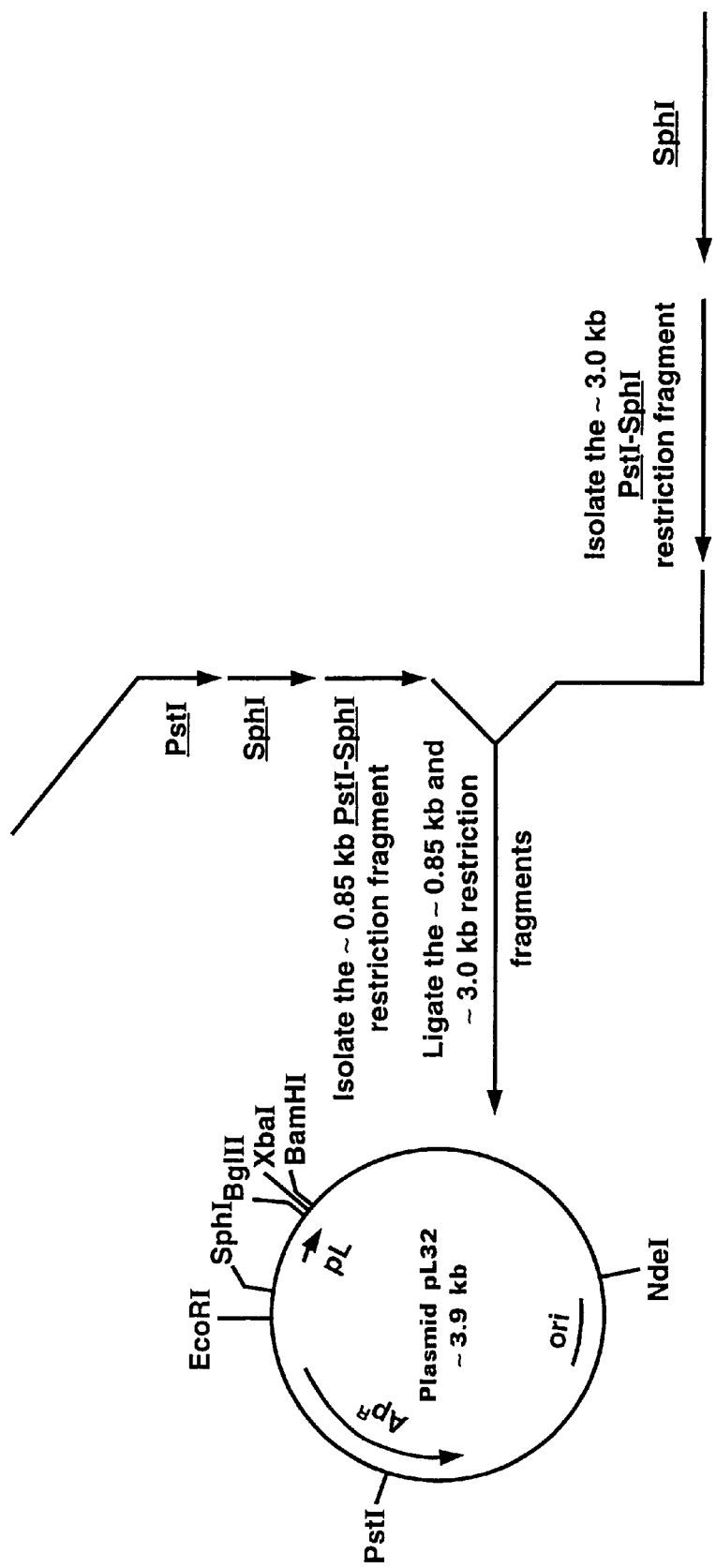
Figure 14:
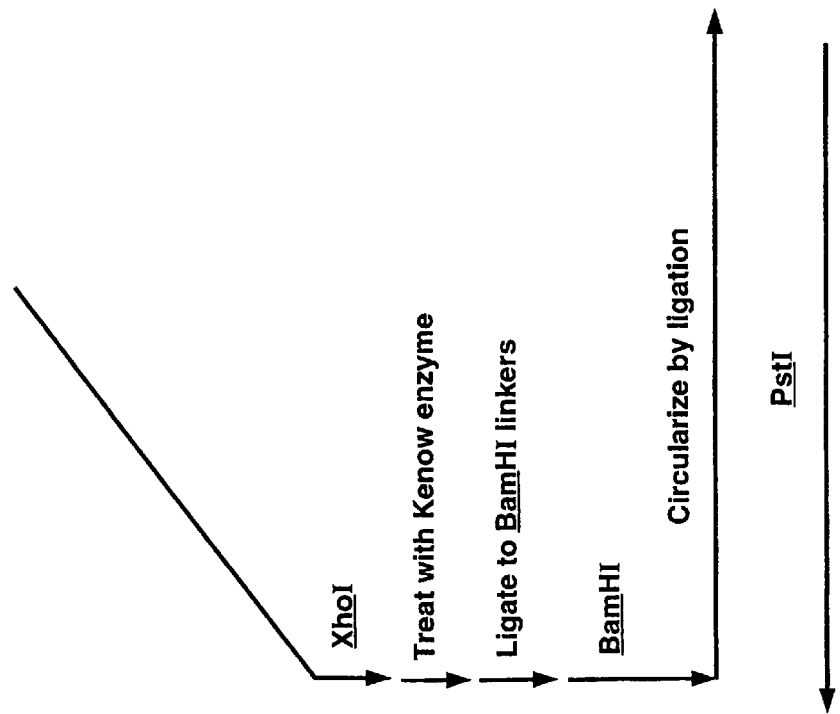
Figure 14:
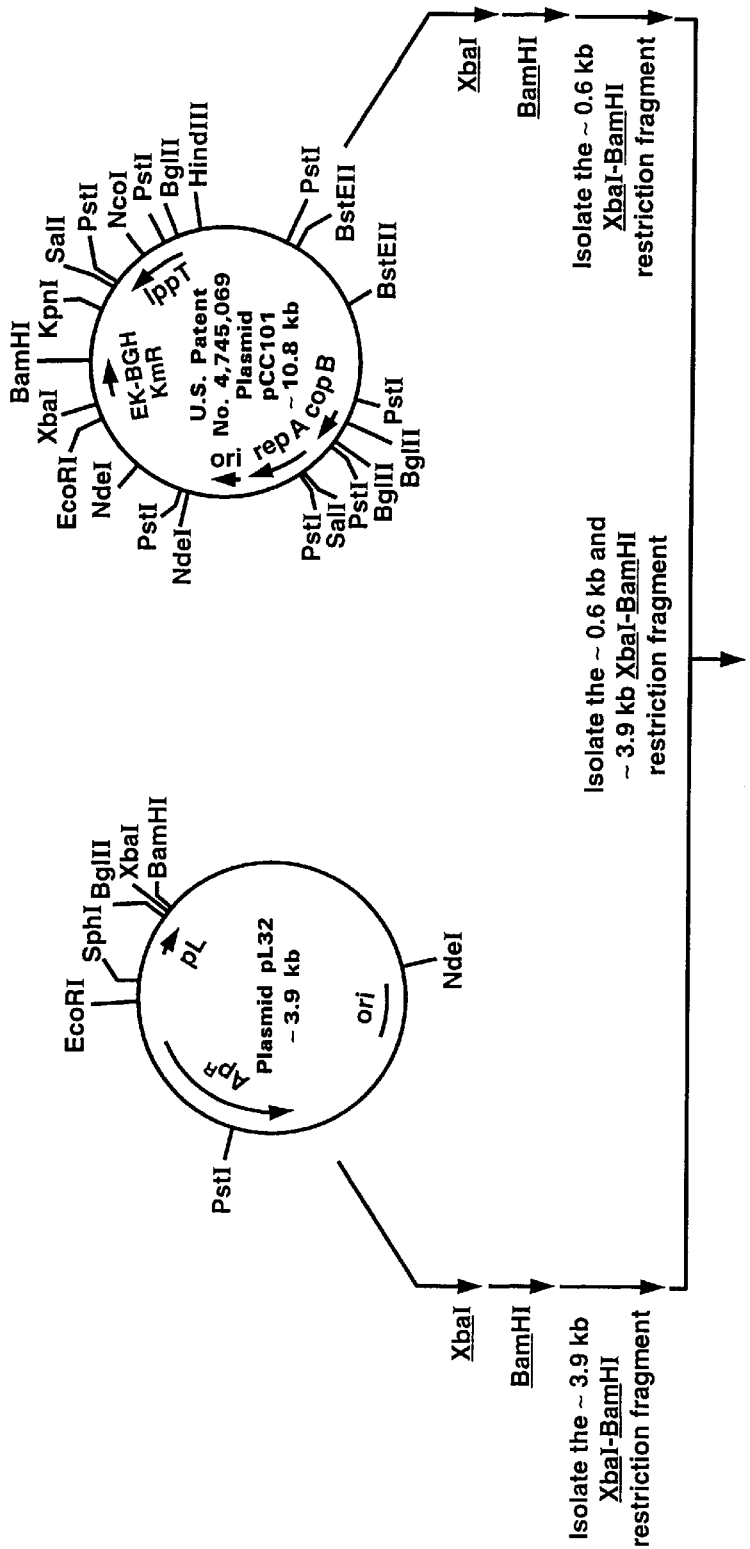
Figure 14:
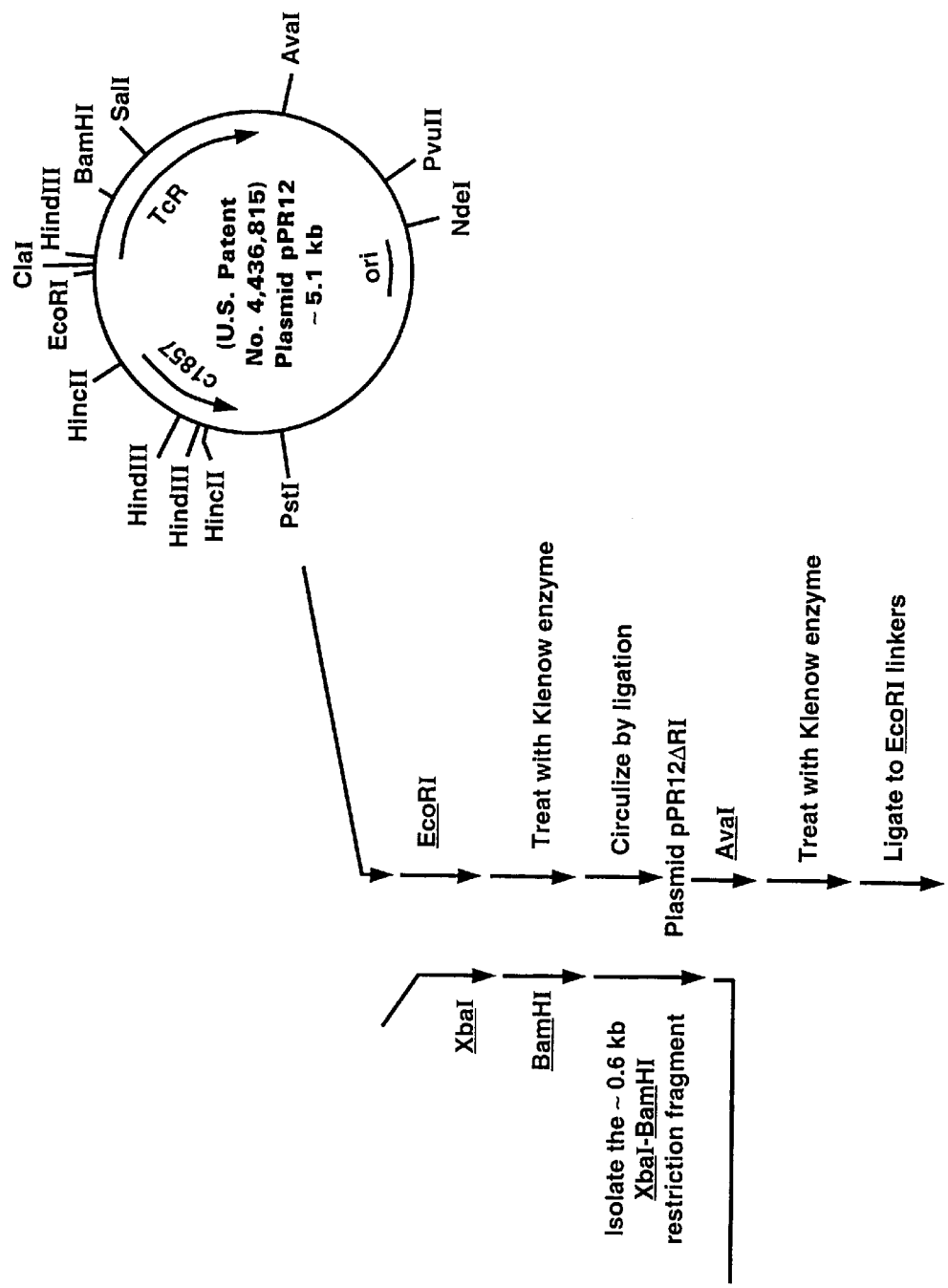
Figure 14:
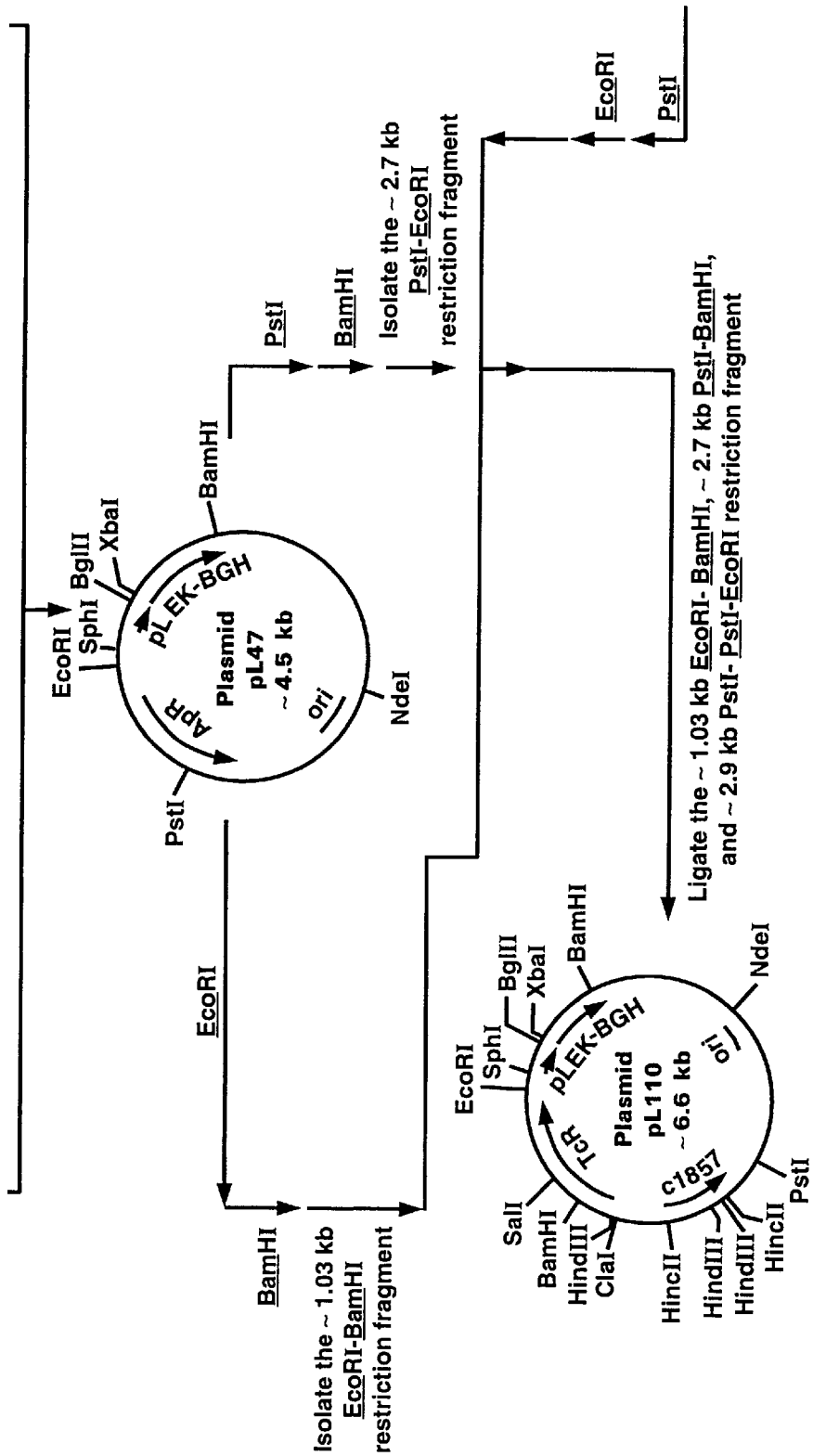
Figure 14:
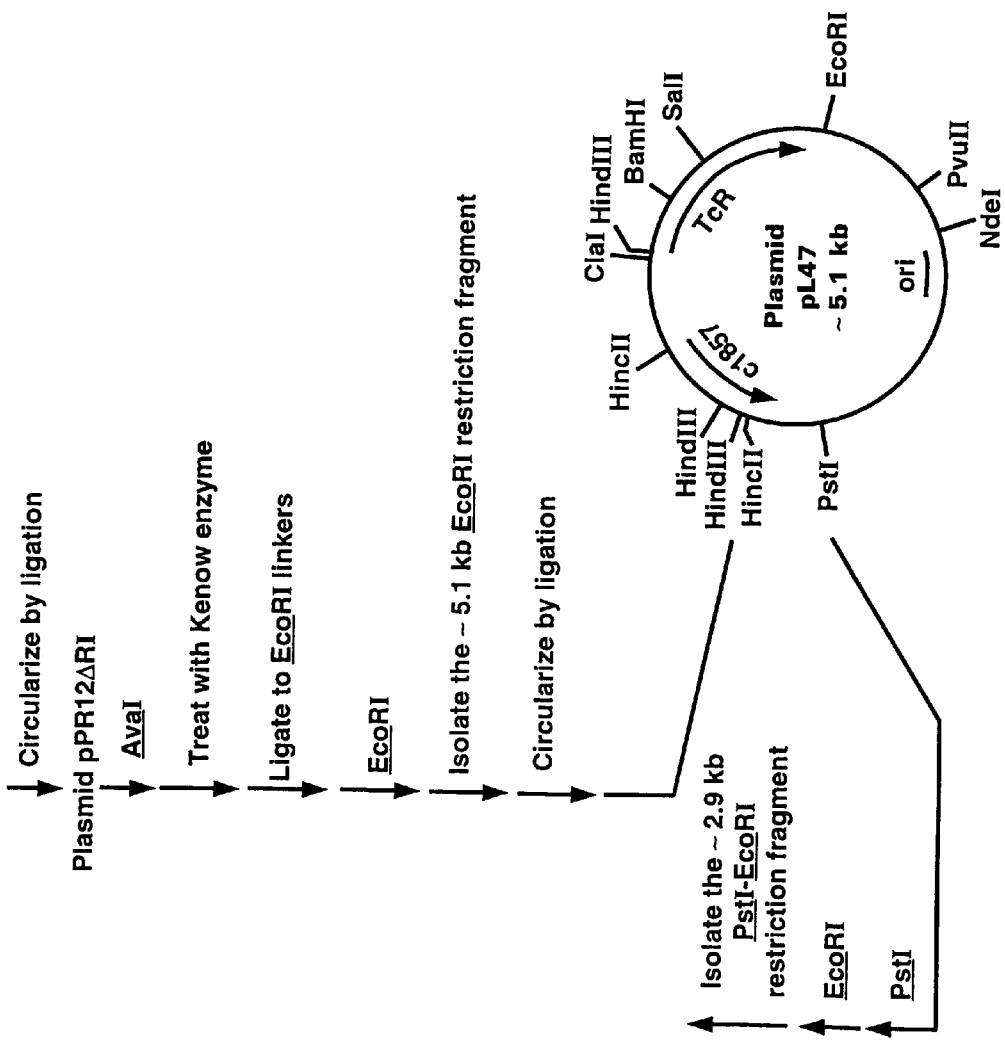

Plasmid pLPChyg1 was further modified to introduce a dihydrofolate reductase (dhfr) gene. The dhfr gene is a selectable marker in dhfr-negative cells and can be used to increase the copy number of a DNA segment by exposing the host cell to increasing levels of methotrexate. The dhfr gene can be obtained from plasmid pBW32, a plasmid disclosed and claimed in U.S. patent application Ser. No. 769,298, filed Aug. 26, 1985, and incorporated herein by reference. A restriction site and function map of plasmid pBW32 is presented in FIG. 14 of the accompanying drawings. The construction protocol for plasmid pBW32 is described in Example 10.

Figure 15:
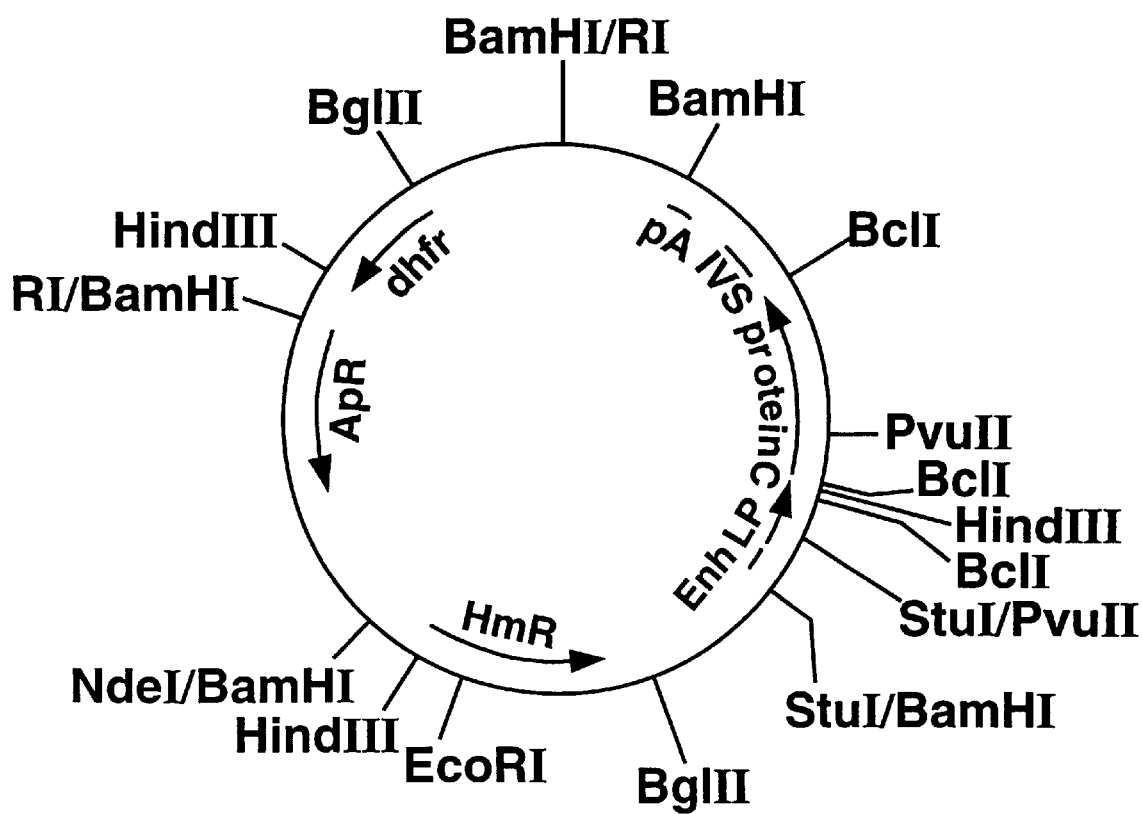
FIG. 15 is a restriction site and function map of plasmid pLPChd1.

The dhfr gene-containing, ~1.9 kb BamHI restriction fragment of plasmid pBW32 was isolated, treated with Klenow enzyme, and inserted into partially-EcoRI-digested plasmid pLPChyg1 to yield plasmids pLPChd1 and pLPChd2. Plasmid pLPChyg1 contains two EcoRI restriction enzyme recognition sites, one in the hygromycin resistance-conferring gene and one in the plasmid pBR322-derived sequences. The fragment comprising the dhfr gene was inserted into the EcoRI site located in the pBR322-derived sequences of plasmid pLPChyg1 to yield plasmids pLPChd1 and pLPChd2. A restriction site and function map of plasmid pLPChd1 is presented in FIG. 15 of the accompanying drawings. The construction of plasmids pLPChd1 and pLPChd2, which differ only with respect to the orientation of the dhfr gene-containing DNA segment, is described in Example 11.

Figure 16:
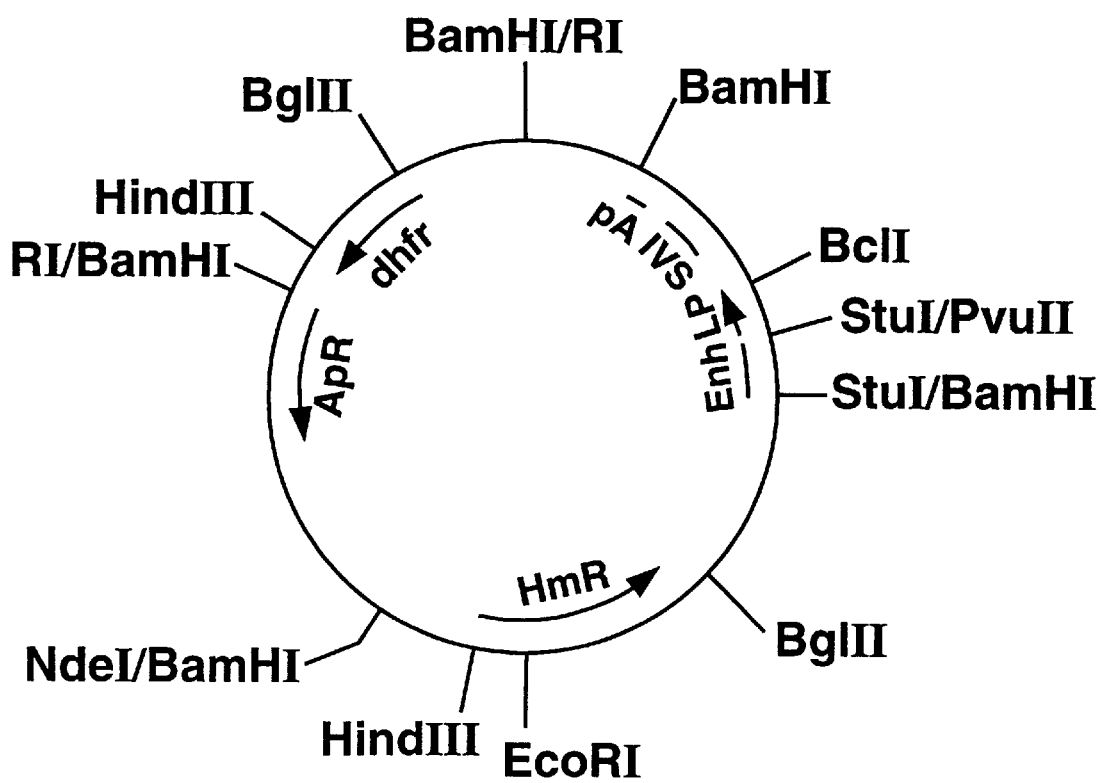
FIG. 16 is a restriction site and function map of plasmid phd.

Plasmid pLPChd1 was modified to form plasmid phd, a plasmid that contains both the present BK enhancer-adenovirus late promoter cassette and also the hygromycin resistance-conferring and dhfr genes. To construct plasmid phd, plasmid pLPChd1 was prepared from dam⁻ E. coli host cells, digested with restriction enzyme BclI, and recircularized, thus deleting the human protein C-encoding DNA. Plasmid phd contains a single BclI restriction enzyme recognition site, which is conveniently positioned for the insertion of any sequence desired to be expressed from the BK enhancer-adenovirus late promoter of the present invention. A restriction site and function map of plasmid phd is presented in FIG. 16 of the accompanying drawings, and the construction protocol for plasmid phd is described in Example 12.

Figure 17:
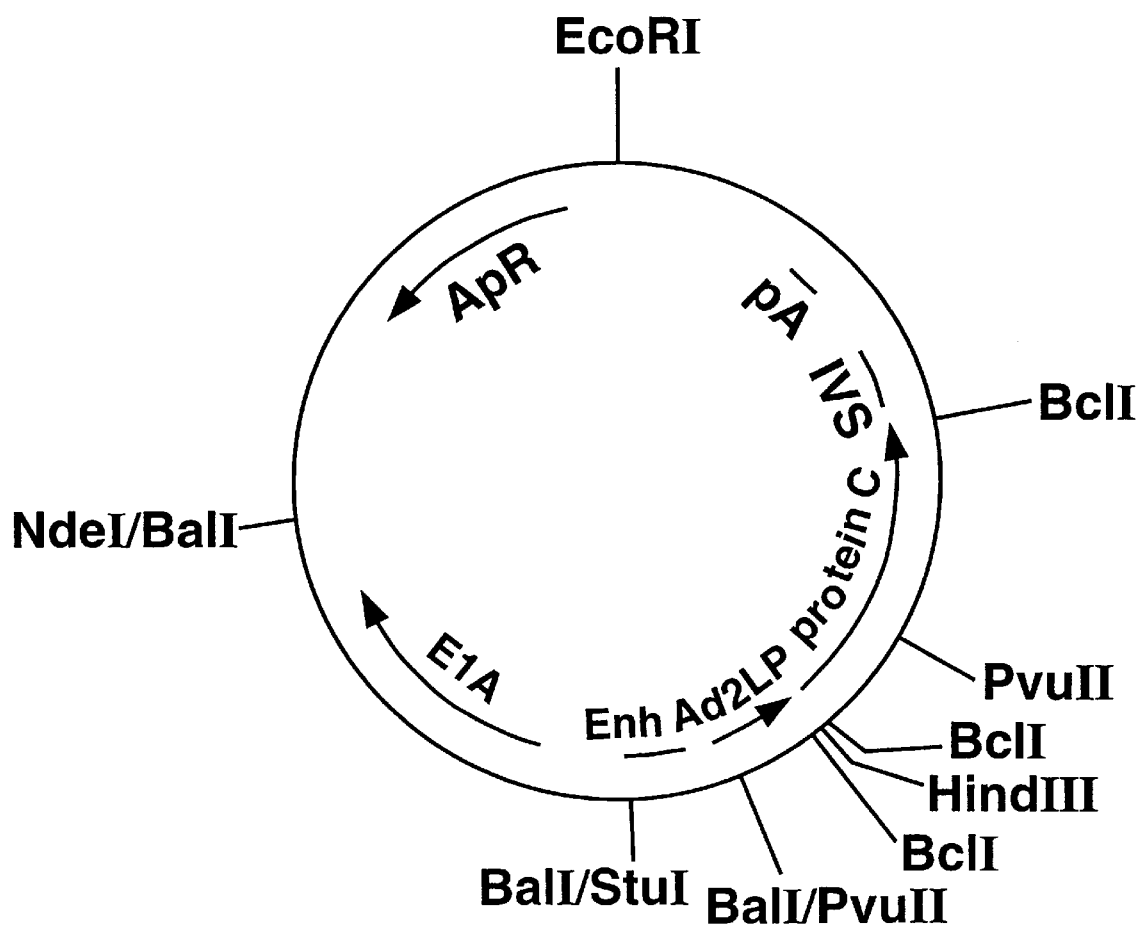
FIG. 17 is a restriction site and function map of plasmid pLPCE1A.

Another expression vector that further exemplifies the present invention and drives expression of human protein C is plasmid pLPCE1A. Plasmid pLPCE1A contains the E1A gene of human adenovirus type 2, the gene product of which, as described above, increases the activity of the BK enhancer. Thus, transcription from a promoter in tandem with the BK enhancer increases in the presence of the E1A gene product. Plasmid pLPCE1A was constructed by ligating the E1A gene-containing, ~1.8 kb BalI restriction fragment of human adenovirus-type-2 DNA with the ~5.82 kb NdeI-StuI restriction fragment of plasmid pLPC. A restriction site and function map of plasmid pLPCE1A is presented in FIG. 17 of the accompanying drawings, and the construction protocol for plasmid pLPCE1A is described in Example 13.

Figure 18:
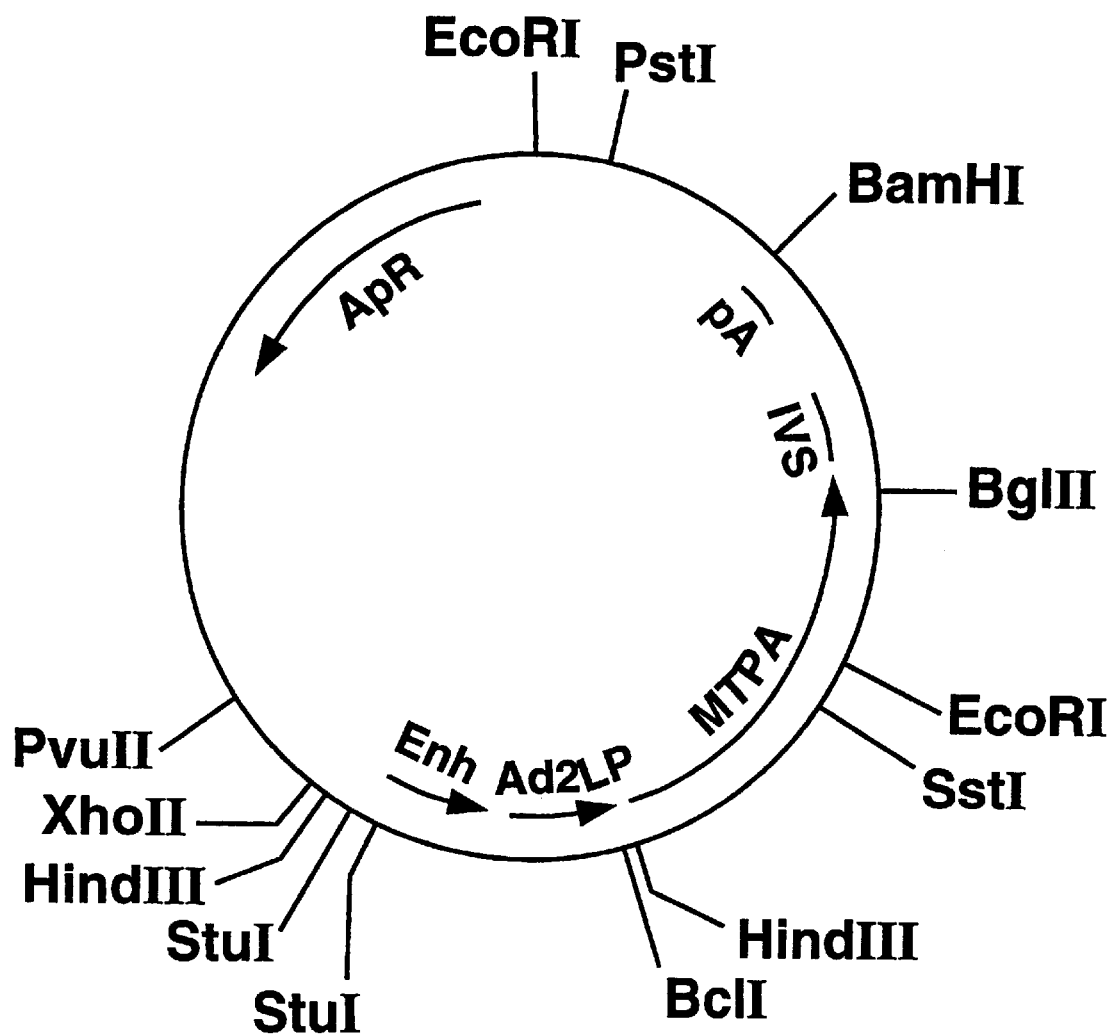
FIG. 18 is a restriction site and function map of plasmid pBLT.

A variety of expression vectors of the present invention utilize the BK enhancer-adenovirus late promoter cassette to drive expression of tissue plasminogen activator (TPA) or modified TPA (MTPA). To construct such vectors, plasmid pBW32 (FIG. 14) was digested with restriction enzyme BamHI, and the resultant ~5.6 kb fragment was recircularized to yield plasmid pBW32del. Plasmid pBW32del, which encodes modified TPA and contains only one HindIII restriction site, was digested with HindIII and then ligated with the ~0.65 kb HindIII restriction fragment of plasmid pBal8cat to yield plasmid pBLT. Plasmid pBal8cat comprises an improved BK enhancer-adenovirus late promoter cassette and is described in Example 17. A restriction site and function map of plasmid pBLT is presented in FIG. 18 of the accompanying drawings, and the construction protocol for plasmid pBLT is described in Example 14.

Figure 19:
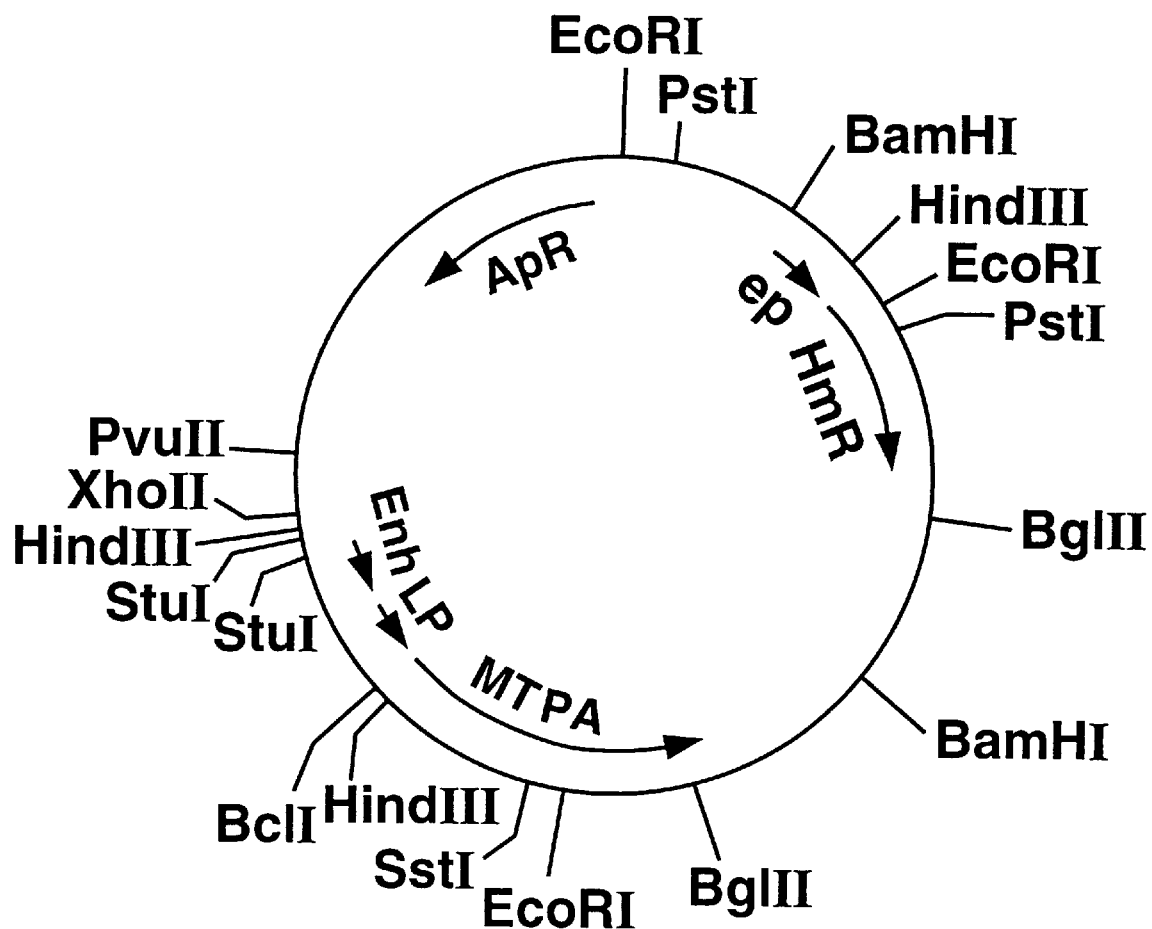
FIG. 19 is a restriction site and function map of plasmid pBLThyg1.
Figure 20:
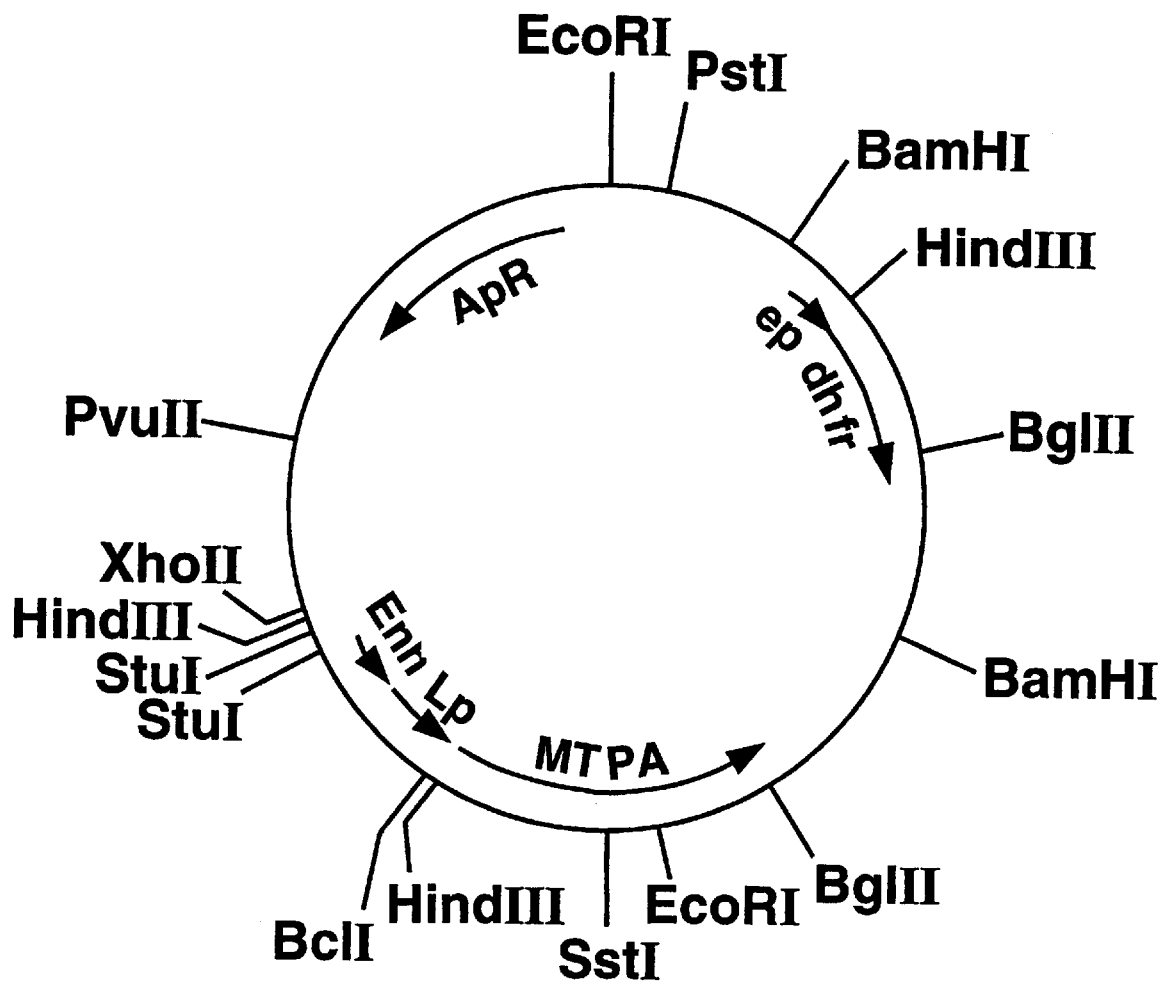
FIG. 20 is a restriction site and function map of plasmid pBLTdhfr1.

Selectable markers were introduced into BamHI-digested plasmid pBLT. In one construction, the hygromycin resistance gene-containing, ~2.5 kb BamHI restriction fragment of plasmid pSV2hyg was inserted to yield plasmids pBLThyg1 and pBLThyg2, and in another construction, the dhfr gene-containing ~1.9 kb BamHI restriction fragment of plasmid pBW32 was inserted to yield plasmids pBLTdhfr1 and pBLTdhfr2. The four plasmids, pBLThyg1, pBLThyg2, pBLTdhfr1, and pBLTdhfr2, differ only with respect to the type and/or orientation of the selectable marker. A restriction site and function map of each of plasmids pBLThyg1 and pBLTdhfr1 is respectively presented in FIGS. 19 and 20 of the accompanying drawings. The construction protocol for plasmids pBLThyg1, pBLThyg2, pBLTdhfr1, and pBLTdhfr2 is described in Example 15.

Figure 21:
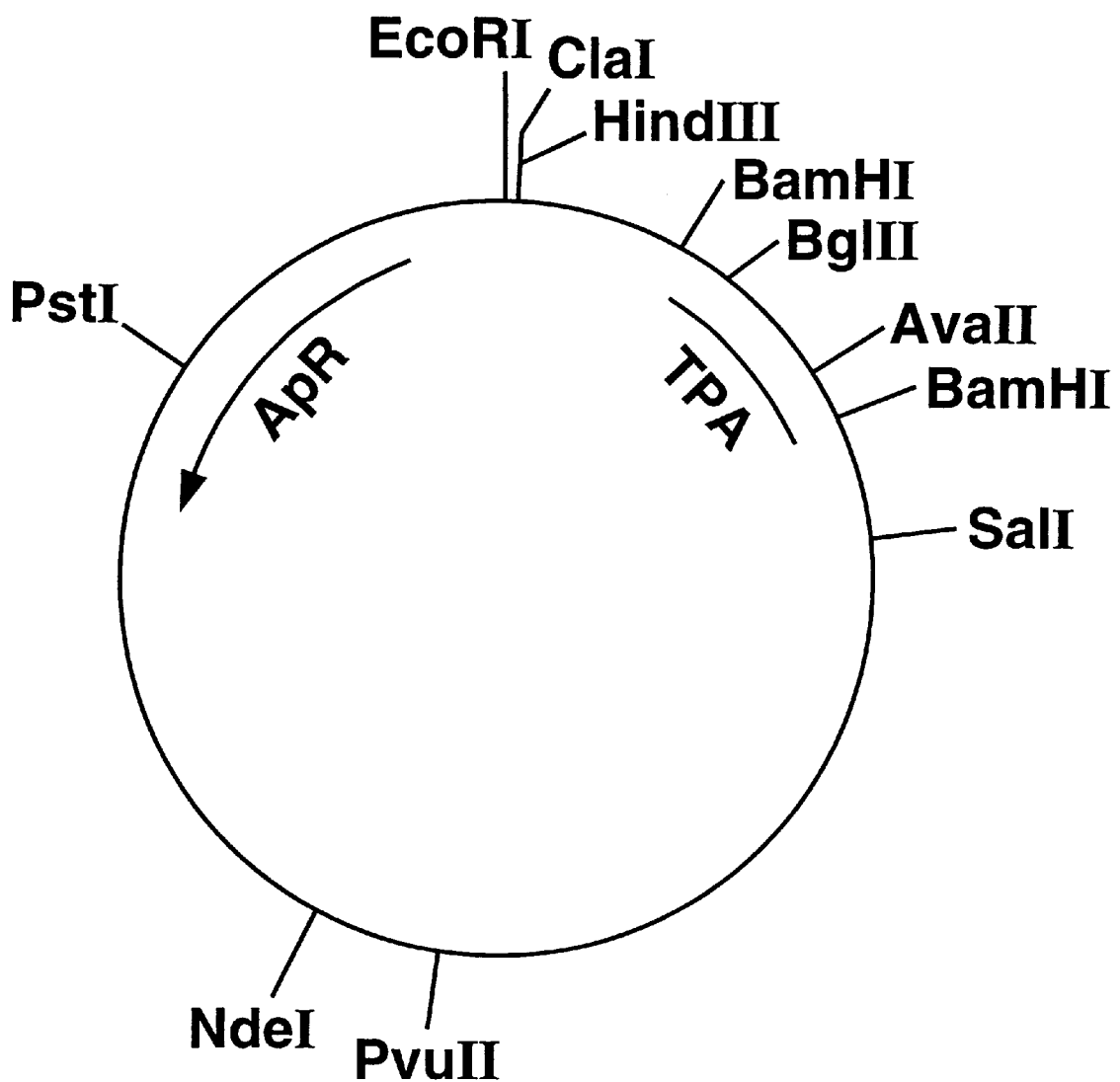
FIG. 21 is a restriction site and function map of plasmid pTPA602.

Other expression vectors of the present invention that drive expression of TPA or modified TPA were derived from plasmid pTPA103, an intermediate used in the construction of plasmid pBW32. The construction protocol for plasmid pTPA103 is described in Example 10, and a restriction site and function map of plasmid pTPA103 is presented in FIG. 14 of the accompanying drawings. To construct these derivatives, a BamHI restriction site was introduced immediately before the 5' end of the TPA coding region of plasmid pTPA103. Plasmid pTPA103 was digested with restriction enzyme HgaI to isolate the ~0.52 kb HgaI restriction fragment that comprises the 5' end of the TPA coding region. After Klenow treatment, the HgaI fragment was ligated to BamHI linkers, digested with restriction enzyme BamHI, and inserted into BamHI-digested plasmid pBR322 to form plasmids pTPA601 and pTPA602. A restriction site and function map of plasmid pTPA602, which differs from plasmid pTPA601 only with respect to the orientation of the inserted BamHI restriction fragment, is presented in FIG. 21 of the accompanying drawings.

Figure 22:
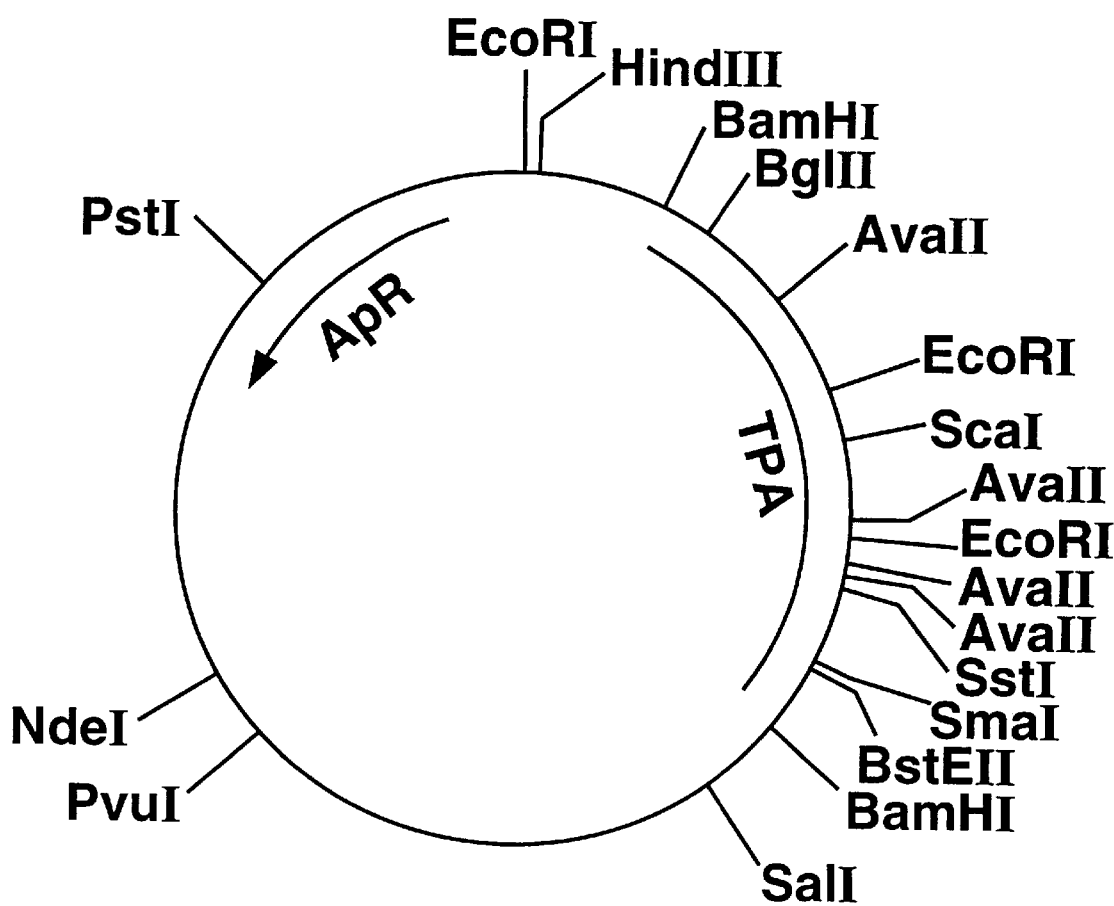
FIG. 22 is a restriction site and function map of plasmid pTPA603.
Figure 23:
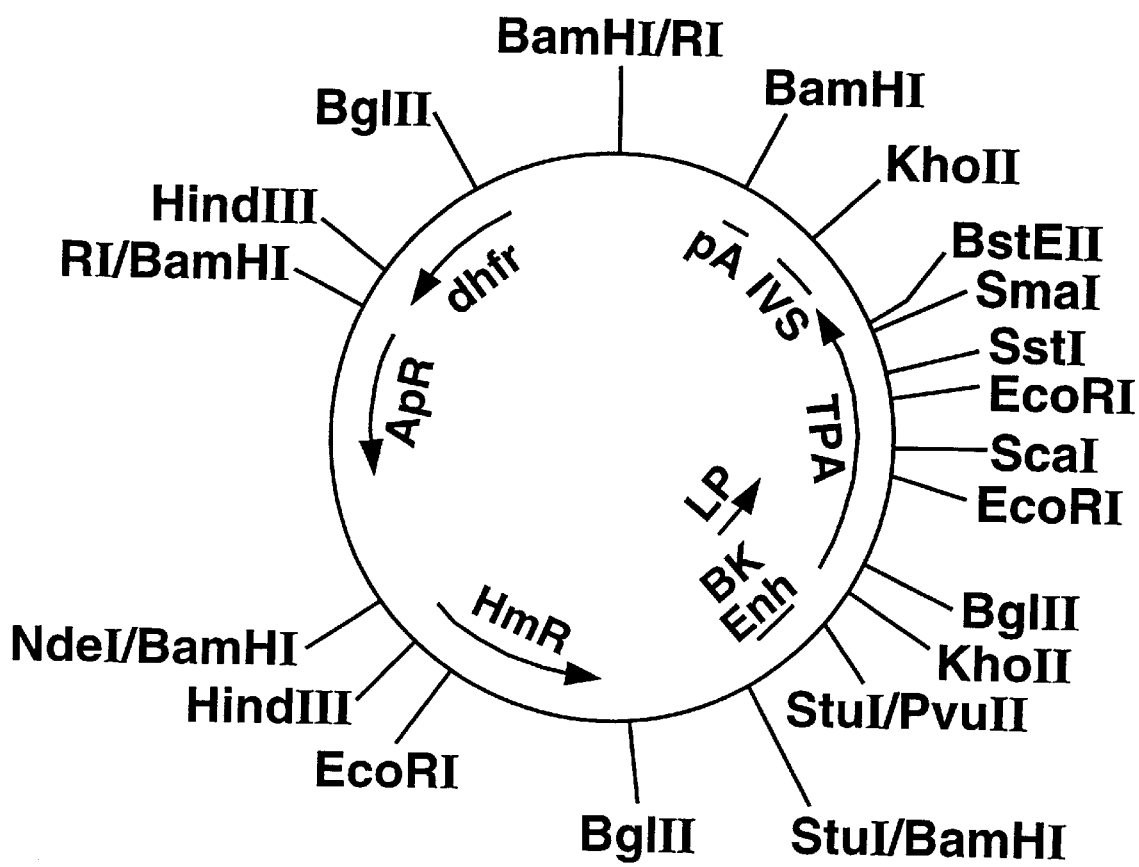
FIG. 23 is a restriction site and function map of plasmid phdTPA.
Figure 24:
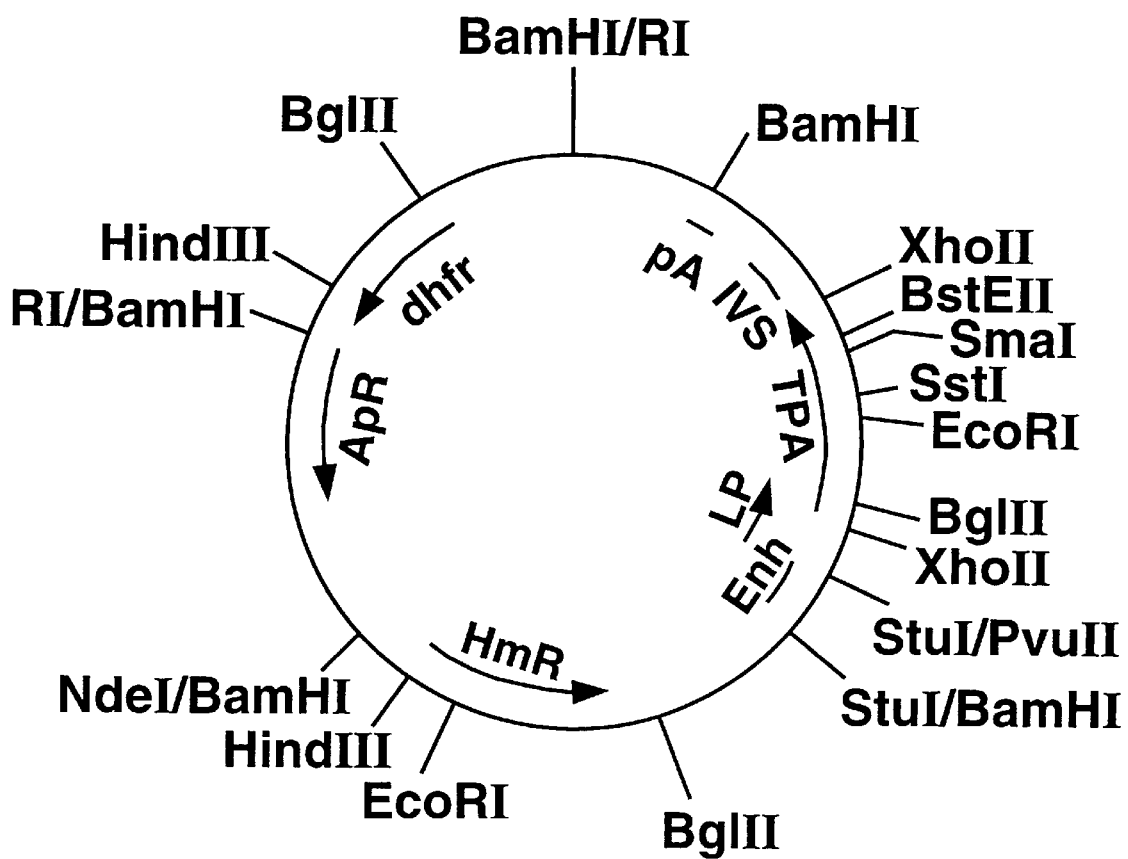
FIG. 24 is a restriction site and function map of plasmid phdMTPA.

Next, plasmid pTPA602 was digested with restriction enzymes BglII and SalI, and the resultant ~4.2 kb BglII-SalI restriction fragment was ligated to the ~2.05 kb SalI-BglII restriction fragment of plasmid pTPA103 to form plasmid pTPA603. Plasmid pTPA603 thus contains the complete coding sequence for TPA bounded by a BamHI restriction site on both ends. A restriction site and function map of plasmid pTPA603 is presented in FIG. 22 of the accompanying drawings. To construct a plasmid that is analogous to plasmid pTPA603 but that encodes a modified form of TPA, plasmid pTPA603 was digested with restriction enzymes BglII and SstI, and the resultant ~5.02 kb BglII-SstI fragment was ligated to the ~0.69 kb BqlII-SstI restriction fragment of plasmid pBLT. The resultant plasmid, designated as pMTPA603, was then digested with restriction enzyme BamHI, and the resultant ~1.35 kb fragment was isolated. This fragment and the ~1.90 kb BamHI restriction fragment of plasmid pTPA603 were individually ligated in separate ligations to BclI-digested plasmid phd (FIG. 16) to form the respective plasmids phdMTPA and phdTPA. Restriction site and function maps of plasmids phdTPA and phdMTPA are respectively presented in FIGS. 23 and 24 of the accompanying drawings. The construction of plasmids phdTPA and phdMTPA, beginning with the construction protocol for plasmid pTPA602, is described in Example 16.

The present invention comprises a method for using the BK enhancer in tandem with a eukaryotic promoter to drive transcription and expression of DNA sequences in eukaryotic host cells that express an immediate-early gene of a large DNA virus. Skilled artisans will recognize that virtually any eukaryotic promoter can be used in tandem with the BK enhancer in the present method. For example, the SV40 early and late promoters, BK early and late promoters, early and late promoters of any of the polyoma viruses or papovaviruses, herpes simplex virus thymidine kinase promoter, interferon α1 promoter, mouse metallothionein promoter, promoters of the retroviruses, β-globin promoter, promoters of the adenoviruses, sea urchin H2A promoter, conalbumin promoter, ovalbumin promoter, mouse β-globin promoter, human β globin promoter, and the Rous sarcoma virus long terminal repeat promoter, can all serve as the eukaryotic promoter in the method of the present invention. Moreover, any sequence containing a transcription start site, composed of a "TATA"-like sequence with or without an upstream "CAAT" sequence, can serve as the promoter in the present invention. Such promoters can be utilized in the present method by conventionally inserting the promoters into expression vectors comprising the BK enhancer as exemplified herein using the adenovirus-2 late promoter, which is the preferred eukaryotic promoter for use in the present method.

Figure 1:
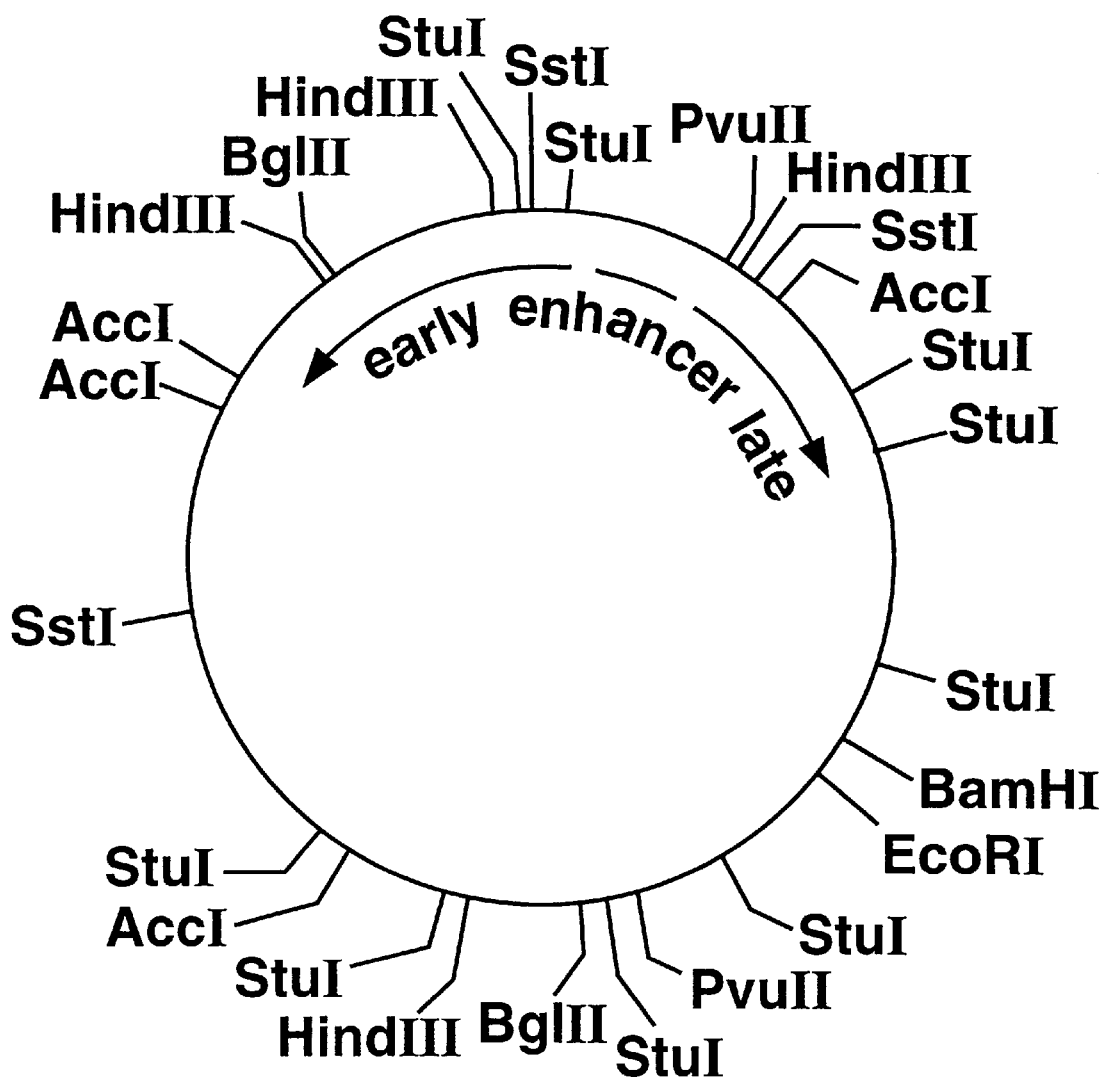
FIG. 1 is a restriction site and function map of BK virus.

The BK enhancer used in the vectors herein that exemplify the present invention was isolated from the prototype strain of BK virus (ATCC VR-837). However, a number of BK virus variants have been isolated and described. Gardner et al., 1971, The Lancet 1:1253, (see also Gardner, 1973, Brit. Med. J. 1:77–78) described the first isolation of a BK virus, and the Gardner strain is thus referred to as the prototype or wild-type BK virus. The Gardner strain of BK virus (FIG. 1) is available from the ATCC under the accession number ATCC VR-837. In fact, when ATCC VR-837 was obtained for use in constructing the vectors of the invention, it was observed that BK variants were present in the population of viruses. Others have observed this phenomenon, i.e., Chuke et al., 1986, J. Virology 60(3):960. Neither the method of using the BK enhancer in tandem with a eukaryotic promoter to drive expression of useful substances, such as nucleic acid and protein, in the presence of an immediate-early gene product of a large DNA virus nor any other method of the present invention is limited to the Gardner strain or a particular BK variant, although the enhancer of the prototype strain is preferred. The following Table lists a representative number of BK variants that can be used in the methods of the present invention. In addition, a BK-like virus (simian agent 12) contains enhancer elements homologous to the BK enhancer and can be used in the methods of the present invention. The enhancer elements of simian agent 12 are described in Cunningham et al., 1985, J. Virol. 54:483–492 and, for purposes of the present invention, are BK enhancer variants.

TABLE 1

BK Variants

| Strain designation | Description (relative to wild-type) | Reference |
| --- | --- | --- |
| BKV(DUN) | BKV(DUN) contains an ~40 bp deletion at 0.7 m.u., just to the late coding side of the viral enhancer core. | Viral Oncology, 1980 (Raven Press, N.Y., ed. G. Klein), pp. 489–540. |
| BK(GS) and BK(MM) | These variants have numerous base differences that include rearrangements and duplications in the control region; some differences occur in the enhancer. | Pater et al., 1979, J. Viral. 32:220–225; Seif et at., 1979, Cell 18:963–977; Yang et al., 1979, Nuc. Acids Res. 7:651–668; and Pater et al., 1979, Virology 131:426–436. |
| BK(JL) | Minor differences in restriction endonuclease patterns. | Pauw et al., 1978, Arch. Viral. 57:35–42. |
| BK(RF) and BK(MG) | These variants are composed of two complementary defective molecules, both of which are required for infectivity and differ extensively in nucleotide sequence from prototype BK virus. | Pater et al., 1980, J. Virol. 36:480–487; Pater et al., 1981, J. Virol. 39:968–972; Pater et al., 1983, Virol. 131:426–436. |
| pm522 | Spontaneous mutation during propagation led to differences in host range and transforming potential, perhaps due to a | Watanabe et al., 1982, J. Virol. 42:978–985; Watanabe et al., 1984, J. Virol. 51:1–6. |

TABLE 1-continued

BK Variants

| Strain designation | Description (relative to wild-type) | Reference |
|---|---|---|
| | deletion of two of the three enhancer repeats and the presence of two sets of shorter 37 bp repeats. | |
| tr530 | Spontaneous mutation during | Watanabe et al., 1984, |
| tr531 | propagation of recombinant | J. Virol. 51:1–6. |
| tr532 | BK virus containing the pm522 enhancer region and having further duplications of short segments originating from the pm522 sequence. | |
| BKV9 | Viable variant of BK virus isolated from a preparation of prototype (wt) BK virus contains an incomplete enhancer repeat and duplication of sequence to the late side of the enhancer. | Chuke et al., 1986, J. Virol. 60:960–971. |
| BK virus-IR | BK virus variant isolated from a human tumor containing insertions and rearrangements in the enhancer region. This virus has an altered transformation phenotype. | Pagnani et al., 1986, J. Virol. 59:500–505. |

Skilled artisans will understand that a variety of eukaryotic host cells can be used in the present method, so long as the host cell expresses an immediate-early gene product of a large DNA virus. Because the immediate-early gene product can be introduced into host cells by many means, such as transformation with a plasmid or other vector, virtually any eukaryotic cell can be used in the present method. Human cells are preferred host cells in the method of the present invention, because human cells are the natural host for BK virus and may contain cellular factors that serve to stimulate the BK enhancer. While human kidney cells are especially preferred as host cells, the adenovirus 5-transformed human embryonic kidney cell line 293, which expresses the E1A gene product, is most preferred and is available from the ATCC under the accession number ATCC CRL 15753.

The 293 cell line is preferred not only because 293 cells express the E1A gene product but also because of the ability of the 293 cells to γ-carboxylate and otherwise properly process complex gene products such as protein C. "γ-Carboxylation" refers to a reaction in which a carboxyl group is added to a glutamic acid residue at the γ-carbon, and a γ-carboxylated protein is a protein in which some amino acid residues have undergone γ-carboxylation. Kidney cells normally γ-carboxylate and otherwise process certain proteins, but 293 cells are transformed with adenovirus, which generally results in a loss of specialized functions. Consequently, the present invention also comprises an improvement in the method for producing a protein that is naturally gamma carboxylated, properly folded, and processed wherein said protein is encoded in a recombinant DNA vector such that said protein is expressed when a eukaryotic host cell containing said vector is cultured under suitable expression conditions, wherein the improvement comprises: (a) inserting said vector into an adenovirus-transformed, human embryonic kidney cell; and (b) culturing said host cell of step a) under growth conditions and in media containing sufficient vitamin K for carboxylation. The 293N3S derivative of the 293 cell line is also suitable for use in the present invention and is able to grow in suspension culture as described in Graham, 1987, J. Gen. Virol. 68:937.

This method of producing a γ-carboxylated protein is not limited to adenovirus-transformed human embryonic kidney cells. Instead, the method of producing a γ-carboxylated protein is broadly applicable to all adenovirus-transformed host cells. Those skilled in the art also recognize that the method can be practiced by first transforming a eukaryotic cell with an expression vector for a γ-carboxylated protein and then transforming the resulting transformant with adenovirus. Harold Ginsberg, in The Adenoviruses (1984, Plenum Press, New York), describes a number of adenoviruses and methods of obtaining adenovirus-transformed host cells. One especially preferred adenovirus-transformed host cell for purposes of expressing a γ-carboxylated protein encoded on a recombinant DNA expression vector is the Syrian hamster cell line AV12-664 (hereinafter AV12). The AV12 cell line was constructed by injecting adenovirus type 12 into the scruff of the neck of a Syrian hamster and isolating cells from the resulting tumor. The AV12 cell line is a preferred host for purposes of producing a γ-carboxylated protein. Examples of γ-carboxylated proteins include, but are not limited to, Factor VII, Factor IX, Factor V, protein C, protein S, protein Z, and prothrombin. Example 19, below, illustrates the advantages of using an adenovirus-transformed host cell for expression of recombinant γ-carboxylated proteins.

In addition to the increased efficiency of γ-carboxylation of proteins, the present invention further provides methods for the production of molecules never before encountered in nature. The gene encoding human protein C is disclosed and claimed in Bang et al., U.S. Pat. No. 4,775,624, issued Oct. 4, 1988, the entire teaching of which is herein incorporated by reference. Human protein C is a glycoprotein which contains four potential sites for the addition of N-linked oligosaccharides. These glycosylation sites occur at the asparagine residues found at positions 97, 248, 313 and 329 of the human protein C molecule. The carbohydrate residues attached to human protein C specifically affect the functional activities (both anticoagulent and amidolytic) of the molecule. Human protein C which is totally deglycosylated has no functional activity. The functional activity of recombinant human protein C from adeno-transformed Baby Hamster Kidney (BHK) cells is about 5–10% lower than fully glycosylated human protein C derived from plasma. However, recombinant human protein C from 293 cells has a functional activity which is 30–40% greater than plasma-derived human protein C.

The differences in functional activities between plasma HPC, rHPC from BHK cells and rHPC from 293 cells are not due to any significant differences in the γ-carboxyglutamate or β-hydroxyaspartate content of the molecules. While all three of the molecules appear to be fully γ-carboxylated, the rHPC from 293 cells demonstrates much higher functional activity. The reason for the different activities lies in the glycosyl content of the separate molecules as summarized in the following table.

TABLE 2

| Sugar | moles sugar/mole of HPC | | |
|---|---|---|---|
| | Plasma HPC | rHPC-293 cells | rHPC-BHK cells |
| Fucose (Fuc) | 0.9 | 4.8 | 4.0 |
| N-acetylgalactosamine (GalNAc) | 0 | 2.6 | 0.62 |
| N-acetylglucosamine (GlcNAc) | 13.8 | 12.4 | 16.8 |
| Galactose (Gal) | 9.3 | 6.0 | 10.6 |
| Mannose (Man) | 9.1 | 8.5 | 10.2 |
| N-acetylneuraminic acid (NeuAc) (Sialic acid) | 10.2 | 5.4 | 10.9 |

This glycosyl content data predicts that for plasma HPC and BHK-derived rHPC the oligosaccharides are predominantly of N-linked complex triantennary structure as shown below:

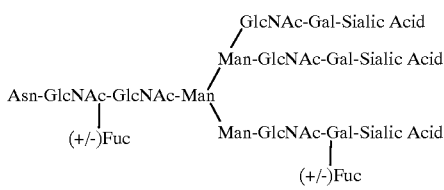

The glycosyl content for rHPC produced in 293 cells, however, predicts that most oligosaccharide chains are predominantly of the N-linked complex biantennary structure as shown below:

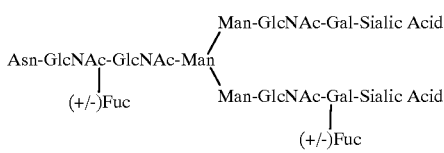

The N-acetylgalactose residues present in rHPC derived from 293 cells are totally in N-linked oligosaccharide structures and not o-linked because they can be totally released by N-glycanose digestion. The total removal of sialic acid from HPC with neuraminidase resulted in a 50% increase in amidolytic activity and a 250–300% increase in anticoagulent activity, therefore, as the sialic acid content of the molecule is lowered, the functional activity of the molecule is increased.

However, the removal of sialic acid and the concomitant exposure of the galactose residue on the non-reducing end of oligosaccharides of glycoproteins results in general, in a tremendous increase in the clearance rate of the glycoprotein by the liver, therefore asialylated glycoproteins are not pharmaceutically preferred. In rHPC derived from 293 cells, the lowering of the sialic acid content is matched with a proportional lowering of the galactosyl content. The ratio of galactose:sialic acid is the same in plasma HPC, rHPC-BHK and rHPC-293 and is close to 1:1 in all three molecules. The data demonstrates that there are few or no galactosyl residues at the non-reducing end of the oligosaccharides in the rHPC from 293 cells. This lower sialic acid content in rHPC from 293 cells is consistent with the interpretation of less branching in the N-linked oligosaccharides. This novel structure results in a molecule with increased activity which should not have an increased rate of clearance from the blood. As the biosynthesis of oligosaccharides on glycoproteins is in part regulated by the "machinary" of the cells from which the glycoproteins are secreted, the methods of the present invention allow for the production of novel glycoprotein molecules from a wide variety of host cells. In particular, recombinant human protein C produced in AV12 cells also displays novel glycosylation patterns.

The novel BK enhancer-eukaryotic promoter constructions described in Example 17 were constructed using a method for improving the activity of the BK enhancer with respect to a eukaryotic promoter. Such method comprises placing the BK enhancer within 0 to 300 nucleotides upstream of the 5' end of the CAAT region or CAAT region equivalent of the eukaryotic promoter used in tandem with the BK enhancer. The improved cassettes produced by this method comprise an important embodiment of the present invention. Use of the improved cassettes is not limited to host cells that express E1A or a similar gene product, although the preferred use does involve stimulation of the improved cassette by an immediate-early gene product of a large DNA virus.

Other viral gene products, such as the VA gene product of adenovirus, can be used to increase the overall efficiency of the present method for using the BK enhancer to promote transcription and expression of recombinant genes in eukaryotic host cells. The VA gene product increases the translation efficiency of mRNA molecules that contain the tripartite leader of adenovirus (Kaufman, 1985, PNAS, 82:689–693, and Svensson and Akusjarul, 1985, EMBO, 4:957–964). The vectors of the present invention can be readily modified to encode the entire tripartite leader of adenovirus; however, as demonstrated in Example 18, the present invention encompasses the use of the VA gene product to increase translation of a given mRNA that only contains the first part of the adenovirus tripartite leader.

The sequence of the tripartite leader of adenovirus is depicted below:

```
          *---------------First Part---------------**------------------Second
5'-ACUCUCUUCCGCAUCGCUGUCUGCGAGGGCCAGCUGUUGGGCUCGCGGUUGAGGACAAACUCUUC Part----------------------------------------------**----------------Third
      GCGGUCUUUCCAGUACUCUUGGAUCGGAAACCCGUCGGCCUCCGAACGUACUCCGCCACCGAGGGACC
```

-continued

```
Part------------------------------------------------------------------*
UGAGCGAGUCCGCAUCGACCGGAUCGGAAAACCUCUCGAGAAAGGCGUCUAACCAGUCACAGUCGCA-3',
``` wherein A is riboadenyl, G is riboguanyl, C is ribocytidyl, and U is uridyl. As encoded in adenovirus DNA, the tripartite leader is interrupted by large introns. The presence of these introns or portions of the introns does not adversely affect expression levels. Plasmids p4-14 and p2-5 of the present invention contain the tripartite leader of adenovirus and are described more fully in Example 20, below.

Many of the illustrative vectors of the invention, such as plasmids pBLcat and PLPC, contain only the first part of the tripartite leader of adenovirus. As used herein, the "first part" of the tripartite leader of adenovirus, when transcribed into mRNA, comprises at least the sequence:

5'-ACUCUCUUCCGCAUCGCUGUCUGCGAGGGCCAG-3'.

Thus, the present invention comprises an improvement in the method for producing a useful substance in a eukaryotic host cell that is transformed with a recombinant DNA vector that contains both a eukaryotic promoter and a DNA sequence that encodes said useful substance, said sequence being positioned for expression from said promoter, and wherein said cell containing said vector is cultured under conditions suitable for expression of said useful substance, wherein the improvement comprises:

(a) incorporating DNA that encodes the first part of the tripartite leader of an adenovirus into said vector such that, upon transcription, the mRNA produced encodes said useful product and, at the 5' end, contains said first part of the tripartite leader;

(b) providing said cell containing the vector of step a) with a DNA sequence that codes for the expression of a VA gene product of said adenovirus; and (c) culturing said cell of step b) under conditions suitable for expressing said VA gene product and for stimulating translation of said mRNA, subject to the limitation that said mRNA does not contain the entire tripartite leader of said adenovirus.

Plasmids coding for VA have been constructed from adenovirus DNA. A restriction fragment of ~1723 bp, defined by a SalI site (at nucleotide 9833) and a HindIII site (at nucleotide 11556), was isolated from adenovirus-2 DNA and cloned into HindIII-SalI-digested plasmid pBR322, thus replacing the ~622 bp SalI-HindIII fragment of pBR322, to construct plasmid pVA. A plasmid coding for neomycin resistance and VA has been constructed by isolating a ~1826 bp NruI fragment from plasmid pVA and inserting that fragment into Klenow-treated, BamHI-digested plasmid pSVNeo (available from BRL). The resultant plasmid, designated pVA-Neo, can be used to insert the VA gene into any cell line by selection of neomycin (G418) resistance after transformation.

The VA gene product of adenovirus, however, may exert its greatest positive effect on expression of recombinant genes containing either the first part of the tripartite leader of adenovirus, or the entire tripartite leader, in the first few days following transformation of the host cell with a VA-encoding vector. Subsequent expression of the VA gene product in the host cell after the first few days may not give optimal expression levels. However, presence of the first part of the tripartite leader on the expression vector and resulting message will lead to increased expression of the product encoded by the mRNA, even in the absence of the VA gene product, in comparison to expression vectors and mRNA molecules that lack the first part of the tripartite leader.

The T antigen of SV40, BK virus, or any other polyomavirus can also be used with the vectors of the present invention to increase promoter activity and/or increase copy number of the plasmid by stimulating replication. SV40 T antigen stimulates transcription from both the adenovirus and BK late promoters. By including T-antigen-coding sequences on the expression vectors of the present invention or by cotransfection of the vectors with a plasmid(s) carrying T-antigen-coding sequences, amplification of copy number can be obtained prior to the application of selective pressure as outlined in Example 18. This will allow for high copy number integration of the expression vector.

Thus, in the preferred embodiment of the present invention, the recombinant DNA expression vector comprises the BK enhancer of the prototype strain positioned less than 300 nucleotides upstream of the adenovirus late promoter, which itself is positioned to drive expression of a gene that encodes at least the first part of the tripartite leader and a useful substance. This preferred vector is used to transform human embryonic kidney 293 cells that have been modified, either before or after transformation with the expression vector, to express the VA gene product of an adenovirus. For stable transformants, however, presence of the VA gene product may not be desired.

The present invention also concerns a method of amplifying genes in primate cells. DNA encoding a directly selectable marker, the murine dihydrofolate reductase gene and a structural polypeptide is introduced into primate cells. Those cells which contain the directly selectable marker are then reisolated and treated with progressively increasing amounts of methotrexate to amplify the genes for dihydrofolate reductase and the structural polypeptide. This method allows for a significant increase in the amount of the structural polypeptide gene that can be in the cells.

Many gene products require extensive post-translated modification for functional activity. As some cell lines do not efficiently modify such gene products, it is advantageous to express these genes in those cell lines which can perform such modifications. Human protein C is one gene product which requires both gamma carboxylation and the removal of a propiece after the translation of the gene. These post-translational modifications occur most efficiently in primate cells, yet the genes encoding such gene products cannot be directly amplified in primate cells.

The most common system for gene amplification employs the murine dihydrofolate reductase (dhfr) gene in dhfr deficient cell lines. Dihydrofolate reductase reduces folic acid to tetrahydrofolic acid, which is involved in the synthesis of thymidylic acid. Methotrexate binds to dihydrofolate reductase, thereby preventing the biosynthesis of thymidylic acid. Dihydrofolate reductase deficient cells, therefore, cannot survive in an environment which does not contain thymidylic acid, while the presence of methotrexate in the culture media requires a concomitant increase in the amount of non-bound dihydrofolate reductase for cell survival.

Primate cells, on the other hand, which are most efficient in the post-translational modification of certain polypeptides, also contain a constitutive dhfr gene. The presence of the constitutive dhfr gene prevents the direct selection of transformants and amplifications of genes using methotrexate. The method of the present invention allows for the direct selection of transformants using a separate selectable marker, such as the hygromycin resistance-conferring gene or the neomycin resistance-conferring gene. Following this direct selection, the genes may then be amplified by progressively increasing the level of methotrexate in the culture media. Many cells which demonstrate an increased level of dhfr gene copy number as well as any increase in the copy number of the structural polypeptide gene.

The method of gene amplification in primate cells is in no way dependent upon any given means for the introduction of the DNA into the cells. Those skilled in the art recognize that DNA may be introduced into cells by electroporation, microinjection, transformation or transfection. Furthermore, the DNA can either be linear or circular. The gene encoding a selectable marker does not need to be an antibiotic resistance conferring gene. Skilled artisans understand that any means for direct selection may be utilized in the present invention. For example, a gene encoding an antigenic determinant could be introduced into a cell line, and cells containing this determinant could be easily selected using immunological methods which are well known in the art.

The directly selectable marker gene, the dhfr gene and the structural polypeptide gene do not need to be introduced into the cell on the same piece of DNA. For example, the directly selectable marker may be transfected into the cell on one plasmid, while the dhfr and structural polypeptide genes may be transfected into the cell on a separate plasmid. This occurs when the hygromycin resistance conferring gene is transfected into 293 cells via plasmid pLPGhyg, while the dhfr and human protein C genes are transfected into the same cells via plasmid pLPCdhfr. Alternatively, the dhfr and human protein C genes can be introduced into plasmid pLPChyg-transfected 293 cells via plasmid p4-14. The neomycin-resistance conferring gene can be used in place of the hygromycin resistance-conferring gene, in which case plasmid pSV2neo is introduced into the cell line rather than plasmid pLPChd. In addition to co-transfection with different plasmids, the directly selectable marker gene, the dhfr gene and the structural polypeptide gene can all be introduced into the host cell on one plasmid. This is exemplified by the transfection of cell line 293 with plasmid pLPChd. Furthermore, other types of primate cells, such as the monkey kidney MK2 cell line (ATCC CCL7), may be used in the method of the present invention.

The following Examples more fully describe the methods, compounds, and recombinant organisms of the present invention. Those skilled in the art will recognize that the particular reagents, equipment, and procedures described in the Examples are merely illustrative and do not limit the present invention.

EXAMPLE 1

Preparation of BK Virus DNA

BK virus is obtained from the American Type Culture Collection under the accession number ATCC VR-837. The virus is delivered in freeze-dried form and resuspended in Hank's balanced salts (Gibco, 3175 Staley Road, Grand Island, N.Y. 14072) to a titer of about $10^5$ plaque-forming units (pfu)/ml. The host of choice for the preparation of BK virus DNA is primary human embryonic kidney (PHEK) cells, which can be obtained from Flow Laboratories, Inc., 7655 Old Springhouse Road, McLean, Va. 22101, under catalogue number 0-100 or from M.A. Bioproducts under catalogue number 70-151.

About five 75 mm$^2$ polystyrene flasks comprising confluent monolayers of about $10^6$ PHEK cells are used to prepare the virus. About 1 ml of BK virus at a titer of $10^5$ pfu/ml is added to each flask, which is then incubated at 37° C. for one hour, and then, fresh culture medium (Dulbeccols Modified Eagle's Medium, Gibco, supplemented with 10% fetal bovine serum) is added, and the infected cells are incubated at 37° C. for 10–14 days or until the full cytopathogenic effect of the virus is noted. This cytopathogenic effect varies from cell line to cell line and from virus to virus but usually consists of cells rounding up, clumping, and sloughing off the culture disk.

The virus is released from the cells by three freeze-thaw cycles, and the cellular debris is removed by centrifugation at 5000×g. The virus in 1 liter of supernatant fluid is precipitated and collected by the addition of 100 g of PEG-6000, incubation of the solution for 24 hours at 4° C., and centrifugation at 5000×g for 20 minutes. The pellet is dissolved in 0.1×SSC buffer (1×SSC=0.15 M NaCl and 0.015 M NaCitrate, pH=7) at $\frac{1}{100}$th of the original volume. The virus suspension is layered onto a 15 ml solution of saturated KBr in a tube, which is centrifuged at 75,000×g for 3 hours. Two bands are evident in the KBr solution after centrifugation. The lower band, which contains the complete virion, is collected and desalted on a Sephadex® G-50 column (Sigma Chemical Co., P.O. Box 14508, St. Louis, Mo. 63178) using TE (10 mM Tris-HCl, pH=7.8, and 1 mM EDTA) as an elution buffer.

Sodium dodecyl sulfate (SDS) is added to the solution of purified virions obtained from the column to a concentration of 1%; pronase is added to a concentration of 100 µg/ml, and the solution is incubated at 37° C. for 2 hours. Cesium chloride is then added to the solution to a density of 1.56 g/ml, and ethidium bromide is added to the solution to a final concentration of 100 µg/ml. The solution is centrifuged in a Sorvall (DuPont Inst. Products, Biomedical Division, Newton, Conn. 06470) 865 rotor or similar vertical rotor at 260,000×g for 24 hours. After centrifugation, the band of virus DNA is isolated and extracted five times with isoamyl alcohol saturated with 100 mM Tris-HCl, pH=7.8. The solution of BK virus DNA is then dialyzed against TE buffer until the 260 nm/280 nm absorbance ratio of the DNA is between 1.75 and 1.90. The DNA is precipitated by adjusting the NaCl concentration to 0.15 M, adding two volumes of ethanol, incubating the solution at −70° C. for at least 2 hours, and centrifuging the solution at 12,000×g for 10 minutes. The resulting pellet of BK virus DNA is suspended in TE buffer at a concentration of 1 mg/ml.

EXAMPLE 2

Construction of Plasmids pBKE1 and pBKE2

About one µg of the BK virus DNA prepared in Example 1 in one µl of TE buffer was dissolved in 2 µl of 10333 EcoRI buffer (1.0 M Tris-HCl, pH=7.5; 0.5 M NaCl; 50 mM MgCl$_2$; and 1 mg/ml BSA) and 15 µl of H$_2$O. About 2 µl (~10 units; all enzyme units referred to herein, unless otherwise indicated, refer to the unit definitions of New England Biolabs, 32 Tozer Road, Beverly, Mass. 01915-9990, although the actual source of the enzymes may have been different) of restriction enzyme EcoRI were added to the solution of DNA, and the resulting reaction was incubated at 37° C. for two hours.

About 1 µg of plasmid pUC8 (available from Pharmacia P-L Biochemicals, 800 Centennial Ave., Piscataway, N.J. 08854) in 1 µl of TE buffer was digested with EcoRI in substantial accordance with the procedure used to prepare the EcoRI-digested BK virus DNA. The EcoRI-digested plasmid pUC8 DNA was diluted to 100 μl in TE buffer; ~0.06 units of calf-intestinal alkaline phosphatase were added to the solution, and the resulting reaction was incubated at 37° C. for 30 minutes. The solution was adjusted to contain 1×SET (5 mM Tris-HCl, pH=7.8; 5 mM EDTA; and 150 mM NaCl), 0.3M NaOAc, and 0.5% SDS and then incubated at 65° C. for 45 minutes. The phosphatase treatment prevents the pUC8 DNA from self ligating.

The EcoRI-digested BK virus and plasmid pUC8 DNA were extracted first with buffered phenol and then with chloroform. The DNA was collected by adjusting the NaCl concentration of each DNA solution to 0.25 M, adding two volumes of ethanol, incubating the resulting mixtures in a dry ice-ethanol bath for 5 minutes, and centrifuging to pellet the DNA. The supernatants were discarded, and the DNA pellets were rinsed with 70% ethanol, dried, and resuspended in 10 μl and 30 μl of TE buffer for the BK and plasmid pUC8 samples, respectively.

About 3 μl of H$_2$O and 1 μl of 10×ligase buffer (0.5 M Tris-HCl, pH=7.8; 100 mM MgCl$_2$; 200 mM DTT; 10 mM ATP; and 0.5 mg/ml BSA) were added to a mixture of 2 μl of the EcoRI-digested BK virus and 1 μl of the EcoRI-digested plasmid pUC8 DNA. One μl (~1000 units) of T4 DNA ligase were added to the solution of DNA, and the resulting reaction was incubated at 16° C. overnight. The ligated DNA constituted the desired plasmids pBKE1 and pBKE2, which differ only with respect to the orientation of the inserted BK virus DNA. A restriction site and function map of plasmid pBKE1 is presented in FIG. 2 of the accompanying drawings.

A 50 ml culture of E. coli K12 JM103, available from Pharmacia P-L Biochemicals, in L-broth was grown to an optical density at 650 nanometers (O.D.$_{650}$) of approximately 0.4 absorbance units. The culture was chilled on ice for ten minutes, and the cells were collected by centrifugation. The cell pellet was resuspended in 25 ml of cold 100 mM MgCl$_2$ and incubated on ice for 25 minutes. The cells were once again pelleted by centrifugation, and the pellet was resuspended in 2.5 ml of cold 100 mM CaCl$_2$ and incubated for 30 minutes on ice. After the incubation, the cells are competent for the uptake of transforming DNA.

Two hundred μl of this cell suspension were mixed with the ligated DNA prepared above and incubated on ice for 30 minutes. At the end of this period, the cells were placed in a water bath at 42° C. for 2 minutes and then returned to the ice for an additional 10 minutes. The cells were collected by centrifugation and resuspended in one ml of L broth and incubated at 37° C. for 1 hour.

Aliquots of the cell mixture were plated on L-agar (L broth with 15 grams of agar per liter) plates containing 100 μg ampicillin/ml, 40 μg X-gal/ml, and 40 μg IPTG/ml. The plates were incubated at 37° C. overnight. Colonies that contain a plasmid without an insert, such as E. coli K12 JM103/pUC8, appear blue on these plates. Colonies that contain a plasmid with an insert, such as E. coli K12 JM103/pBKE1, are white. Several white colonies were selected and screened by restriction enzyme analysis of their plasmid DNA for the presence of the ~5.2 kb EcoRI restriction fragment of BK virus. Plasmid DNA was obtained from the E. coli K12 JM103/pBKE1 and E. coli K12 JM103/pBKE2 cells in substantial accordance with the procedure for isolating plasmid DNA that is described in the following Example, although the procedure is done on a smaller scale, and the CsCl gradient steps are omitted, when the plasmid DNA is isolated only for restriction enzyme analysis.

EXAMPLE 3

Construction of Plasmids pBKneo1 and pBKneo2

E. coli K12 HB101/pdBPV-MMTneo cells are obtained in lyophil form from the American Type Culture Collection under the accession number ATCC 37224. The lyophilized cells are plated on L-agar plates containing 100 μg/ml ampicillin and incubated at 37° C. to obtain single colony isolates.

One liter of L broth (10 g tryptone, 10 g NaCl, and 5 g yeast extract per liter) containing 50 μg/ml ampicillin was inoculated with a colony of E. coli K12 HB101/pdBPV-MMTneo and incubated in an air-shaker at 37° C. until the O.D.$_{590}$ was ~1 absorbance unit, at which time 150 mg of chloramphenicol were added to the culture. The incubation was continued for about 16 hours; the chloramphenicol addition inhibits protein synthesis, and thus inhibits further cell division, but allows plasmid replication to continue.

The culture was centrifuged in a Sorvall GSA rotor (DuPont Co., Instrument Products, Biomedical Division, Newtown, Conn. 06470) at 6000 rpm for 5 minutes at 4° C. The resulting supernatant was discarded, and the cell pellet was washed in 40 ml of TES buffer (10 mM Tris-HCl, pH=7.5; 10 mM NaCl; and 1 mM EDTA) and then repelleted. The supernatant was discarded, and the cell pellet was frozen in a dry ice-ethanol bath and then thawed. The thawed cell pellet was resuspended in 10 ml of a solution of 25% sucrose and 50 mM EDTA. About 1 ml of a 5 mg/ml lysozyme solution; 3 ml of 0.25 M EDTA, pH=8.0; and 100 μl of 10 mg/ml RNAse A were added to the solution, which was then incubated on ice for 15 minutes. Three ml of lysing solution (prepared by mixing 3 ml 10% Triton-X 100; 75 ml 0.25 M EDTA, pH=8.0; 15 ml of 1 M Tris-HCl, pH=8.0; and 7 ml of water) were added to the lysozyme-treated cells, mixed, and the resulting solution incubated on ice for another 15 minutes. The lysed cells were frozen in a dry ice-ethanol bath and then thawed.

The cellular debris was removed from the solution by centrifugation at 25,000 rpm for 40 minutes in an SW27 rotor (Beckman, 7360 N. Lincoln Ave., Lincolnwood, Ill. 60646) and by extraction with buffered phenol. About 30.44 g of CsCl and ~1 ml of a 5 mg/ml ethidium bromide solution were added to the cell extract, and then, the volume of the solution was adjusted to 40 ml with TES buffer. The solution was decanted into a VTi50 ultra-centrifuge tube (Beckman), which was then sealed and centrifuged in a VTi50 rotor at 42,000 rpm for ~16 hours. The resulting plasmid band, visualized with ultraviolet light, was isolated and then placed in a Ti75 tube and rotor (Beckman) and centrifuged at 50,000 rpm for 16 hours. Any necessary volume adjustments were made using TES containing 0.761 g/ml CsCl. The plasmid band was again isolated, extracted with salt-saturated isopropanol to remove the ethidium bromide, and diluted 1:3 with TES buffer. Two volumes of ethanol were then added to the solution, which was then incubated overnight at -20° C. The plasmid DNA was pelleted by centrifuging the solution in an SS34 rotor (Sorvall) for 15 minutes at 10,000 rpm.

The ~1 mg of plasmid pdBPV-MMTneo DNA obtained by this procedure was suspended in 1 ml of TE buffer and stored at -20° C. The foregoing plasmid isolation procedure is generally used when large amounts of very pure plasmid DNA are desired. The procedure can be modified to rapidly obtain a smaller, less pure amount of DNA, such as is needed when screening transformants for the presence of a given plasmid, by using only about 5 ml of cultured cells, lysing the cells in an appropriately scaled-down amount of lysis buffer, and replacing the centrifugation steps with phenol and chloroform extractions.

About 5 μg (5 μl) of the plasmid pdBPV-MMTneo DNA prepared above and five μg (5 μl) of the BK virus DNA prepared in Example 1 were each digested at 37° C. for 2 hours in a solution containing 2 μl of 10×BamHI buffer (1.5 M NaCl; 60 mM Tris-HCl, pH=7.9; 60 mM MgCl$_2$; and 1 mg/ml BSA), 1 μl of restriction enzyme BamHI, and 7 μl of H$_2$O. The reaction was stopped by an extraction with an equal volume of phenol, followed by two extractions with chloroform. Each BamHI-digested DNA was then precipitated, collected by centrifugation, and resuspended in 5 μl of H$_2$O.

About 1 μl of 10×ligase buffer was added to a mixture of BamHI-digested plasmid pdBPV-MMTneo (1 μl) and BamHI-digested BK virus DNA (1 μl). After 1 μl (~1000 units) of T4 DNA ligase and 6 μl of H$_2$O were added to the mixture of DNA, the resulting reaction was incubated at 16° C. overnight. The ligated DNA constituted the desired plasmids pBKneo1 and pBKneo2, which differ only with respect to the orientation of the BK virus DNA. A restriction site and function map of plasmid pBKneo1 is presented in FIG. 3 of the accompanying drawings.

*E. coli* K12 HB101 cells are available in lyophilized form from the Northern Regional Research Laboratory under the accession number NRRL B-15626. *E. coli* K12 HB101 cells were cultured, made competent for transformation, and transformed with the ligated DNA prepared above in substantial accordance with the procedure of Example 2. The transformed cells were plated on L-agar plates containing 100 μg/ml ampicillin. *E. coli* K12 HB101/pBKneo1 and *E. coli* K12/pBKneo2 transformants were identified by their ampicillin-resistant phenotype and by restriction enzyme analysis of their plasmid DNA.

EXAMPLE 4

Construction of Plasmid pBLcat

A. Construction of Intermediate Plasmid pLPcat

The virion DNA of adenovirus 2 (Ad2) is a double-stranded linear molecule about 35.94 kb in size. The Ad2 late promoter can be isolated on an ~0.316 kb AccI-PvuII restriction fragment of the Ad2 genome; this ~0.32 kb restriction fragment corresponds to the sequence between nucleotide positions 5755 and 6071 of the Ad2 genome. To isolate the desired ~0.32 kb AccI-PvuII restriction fragment, Ad2 DNA is first digested with restriction enzyme BalI, and the ~2.4 kb BalI restriction fragment that comprises the entire sequence of the ~0.32 kb AccI-PvuII restriction fragment is isolated. Then, the ~2.4 kb BalI restriction fragment is digested with AccI and PvuII to obtain the desired fragment.

About 50 μg of Ad2 DNA (available from BRL) are dissolved in 80 μl of H$_2$O and 10 μl of 10×BalI buffer (100 mM Tris-HCl, pH=7.6; 120 mM MgCl$_2$; 100 mM DTT; and 1 mg/ml BSA). About 10 μl (~20 units) of restriction enzyme BalI are added to the solution of Ad2 DNA, and the resulting reaction is incubated at 37° C. for 4 hours.

The BalI-digested DNA is loaded onto an agarose gel and electrophoresed until the restriction fragments are well separated. Visualization of the electrophoresed DNA is accomplished by staining the gel in a dilute solution (0.5 μg/ml) of ethidium bromide and exposing the stained gel to long-wave ultraviolet (UV) light. One method to isolate DNA from agarose is as follows. A small slit is made in the gel in front of the desired fragment, and a small piece of NA-45 DEAE membrane (Schleicher and Schuell, Keene, N.H. 03431) is placed in each slit. Upon further electrophoresis, the DNA non-covalently binds to the DEAE membrane. After the desired fragment is bound to the DEAE membrane, the membrane is removed and rinsed with low-salt buffer (100 mM KCl; 0.1 mM EDTA; and 20 mM Tris-HCl, pH=8). Next, the membrane is placed in a small tube and immersed in high-salt buffer (1 M NaCl; 0.1 mM EDTA; and 20 mM Tris-HCl, pH=8) and then incubated at 65° C. for one hour to remove the DNA from the DEAE paper. After the 65° C. incubation, the incubation buffer is collected and the membrane rinsed with high-salt buffer. The high-salt rinse solution is pooled with the high-salt incubation buffer.

The volume of the high salt-DNA solution is adjusted so that the NaCl concentration is 0.25 M, and then three volumes of cold, absolute ethanol are added to the solution. The resulting solution is mixed and placed at −70° C. for 10–20 minutes. The solution is then centrifuged at 15,000 rpm for 15 minutes. After another precipitation to remove residual salt, the DNA pellet is rinsed with ethanol, dried, resuspended in 20 μl of TE buffer, and constitutes about 3 μg of the desired restriction fragment of Ad2. The purified fragment obtained is dissolved in 10 μl of TE buffer.

About 6 μl of H$_2$O and 2 μl of 10×AccI buffer (60 mM NaCl; 60 mM Tris-HCl, pH=7.5; 60 mM MgCl$_2$; 60 mM DTT; and 1 mg/ml BSA) are added to the solution of the ~2.4 kb BalI restriction fragment of Ad2. After the addition of about 2 μl (~10 units) of restriction enzyme AccI to the solution of DNA, the reaction is incubated at 37° C. for 2 hours. After the AccI digestion, the DNA is collected by ethanol precipitation and resuspended in 16 μl of H$_2$O and 2 μl of 10×PvuII buffer (600 mM NaCl; 60 mM Tris-HCl, pH=7.5; 60 mM MgCl$_2$; 60 mM DTT; and 1 mg/ml BSA). After the addition of about 2 μl (about 10 units) of restriction enzyme PvuII to the solution of DNA, the reaction is incubated at 37° C. for 2 hours.

The AccI-PvuII-digested, ~2.4 kb BalI restriction fragment of Ad2 is loaded onto an ~6% polyacrylamide gel and electrophoresed until the ~0.32 kb AccI-PvuII restriction fragment that comprises the Ad2 late promoter is separated from the other digestion products. The gel is stained with ethidium bromide and viewed using UV light, and the segment of gel containing the ~0.32 kb AccI-PvuII restriction fragment is cut from the gel, crushed, and soaked overnight at room temperature in ~250 μl of extraction buffer (500 mM NH$_4$OAc; 10 mM MgOAc; 1 mM EDTA; and 0.1% SDS). The following morning, the mixture is centrifuged, and the pellet is discarded. The DNA in the supernatant is precipitated with ethanol; about 2 μg of tRNA are added to ensure complete precipitation of the desired fragment. About 0.2 μg of the ~0.32 kb AccI-PvuII restriction fragment are obtained and suspended in 7 μl of H$_2$O.

About 0.25 μg (in 0.5 μl) of BclI linkers (5'-CTGATCAG-3', available from New England Biolabs), which had been kinased in substantial accordance with the procedure described in Example 10A, below, was added to the solution of the ~0.32 kb AccI-PvuII restriction fragment, and then, 1 μl (~1000 units) of T4 DNA ligase and 1 μl of 10×ligase buffer were added to the solution of DNA, and the resulting reaction was incubated at 16° C. overnight. The BclI linkers could only ligate to the PvuII end of the AccI-PvuII restriction fragment. DNA sequencing later revealed that four BclI linkers attached to the PvuII end of the AccI-PvuII restriction fragment. These extra BclI linkers can be removed by BclI digestion and religation; however, the extra BclI linkers were not removed as the linkers do not interfere with the proper functioning of the vectors that comprise the extra linkers.

*E. coli* K12 HB101/pSV2cat cells are obtained in lyophilized form from the ATCC under the accession number ATCC 37155, and plasmid pSV2cat DNA was isolated from the cells in substantial accordance with the procedure of Example 3. A restriction site and function map of plasmid pSV2cat is presented in FIG. 4 of the accompanying drawings. About 1 mg of plasmid pSV2cat DNA is obtained and dissolved in 1 ml of TE buffer. About 3 μg (3 μl) of the plasmid pSV2cat DNA were added to 2 μl of 10×AccI buffer and 16 μl of H$_2$O, and then, 3 μl (about 9 units) of restriction enzyme AccI were added to the solution of pSV2cat DNA, and the resulting reaction was incubated at 37° C. for 2 hours. The AccI-digested plasmid pSV2cat DNA was then digested with restriction enzyme StuI by adding 3 μl of 10×StuI buffer (1.0M NaCl; 100 mM Tris-HCl, pH=8.0; 100 mM MgCl$_2$; 60 mM DTT; and 1 mg/ml BSA), 5 μl of H$_2$O, and about 2 μl (about 10 units) of restriction enzyme StuI. The resulting reaction was incubated at 37° C. for 2 hours. The reaction was terminated by extracting the reaction mixture once with phenol, then twice with chloroform. About 0.5 μg of the desired fragment was obtained and dissolved in 20 μl of TE buffer.

About 4 μl of the AccI-StuI-digested plasmid pSV2cat DNA were mixed with about 7 μl of the ~0.32 kb AccI-PvuII (with BclI linkers attached) restriction fragment of Ad2, and after the addition of 3 μl of 10×ligase buffer, 15 μl of H$_2$O, and 2 μl (about 1000 units) of T4 DNA ligase, the ligation reaction was incubated at 16° C. overnight. The ligated DNA constituted the desired plasmid pLPcat, a plasmid that comprises the Ad2 late promoter positioned so as to drive transcription, and thus expression, of the chloramphenicol acetyltransferase gene. A restriction site and function map of plasmid pLPcat is presented in FIG. 5 of the accompanying drawings.

The ligated DNA was used to transform *E. coli* K12 HB101 cells in substantial accordance with the procedure of Example 3. The transformed cells were plated on L agar containing 50 μg/ml ampicillin; restriction enzyme analysis of plasmid DNA was used to identify the *E. coli* K12 HB101/pLPcat transformants. Plasmid pLPcat DNA was isolated from the transformants for use in subsequent constructions in substantial accordance with the plasmid isolation procedure described in Example 3.

B. Final Construction of Plasmid pBLcat

About 88 μg of plasmid pBKneo1 DNA in 50 μl of TE buffer were added to 7.5 μl of 10×AccI buffer, 30 μl of H$_2$O, and 15 μl (about 75 units) of restriction enzyme AccI, and the resulting reaction was incubated at 37° C. for 2 hours. The AccI-digested BK virus DNA was loaded on an agarose gel, and the ~1.4 kb fragment that contains the BK enhancer was separated from the other digestion products. The ~1.4 kb AccI restriction fragment was then isolated in substantial accordance with the procedure described in Example 4A. About 5 μg of the fragment were resuspended in 5 μl of 10×PvuII buffer, 45 μl of H$_2$O, and 5 μl (about 25 units) of restriction enzyme PvuII, and the resulting reaction was incubated at 37° C. for 2 hours. The PvuII-digested DNA was then isolated and prepared for ligation in substantial accordance with the procedure of Example 4A. About 2 μg of the desired ~1.28 kb AccI-PvuII fragment were obtained and dissolved in 5 μl of TE buffer.

About 1 μg of plasmid pLPcat DNA was dissolved in 5 μl of 10×AccI buffer and 40 μl of H$_2$O. About 5 μl (~25 units) of restriction enzyme AccI were added to the solution of plasmid pLPcat DNA, and the resulting reaction was incubated at 37° C. The AccI-digested plasmid pLPcat DNA was precipitated with ethanol and resuspended in 5 μl of 10×StuI buffer, 40 μl of H$_2$O, and 5 μl (about 25 units) of restriction enzyme StuI, and the resulting reaction was incubated at 37° C. for 2 hours. The AccI-StuI-digested plasmid pLPcat DNA was precipitated with ethanol several times to purify the ~4.81 kb AccI-StuI restriction fragment that comprises the *E. coli* origin of replication and Ad2 late promoter away from the other digestion product, a restriction fragment about 16 bp in size. About 1 μg of the desired ~4.81 kb restriction fragment was obtained and dissolved in 20 μl of TE buffer.

The 5 μl of ~4.81 kb AccI-StuI restriction fragment of plasmid pLPcat were added to 5 μl of ~1.28 kb AccI-PvuII restriction fragment of BK virus. After the addition of 3 μl of 10×ligase buffer, 15 μl of H$_2$O, and 2 μl (about 1000 units) of T4 DNA ligase to the mixture of DNA, the resulting ligation reaction was incubated at 16° C. overnight. The ligated DNA constituted the desired plasmid pBLcat. A restriction site and function map of plasmid pBLcat is presented in FIG. 6 of the accompanying drawings.

The ligated DNA was used to transform *E. coli* K12 HB101 cells in substantial accordance with the procedure described in Example 3. *E. coli* K12 HB101/pBLcat transformants were identified by restriction enzyme analysis of their plasmid DNA. Plasmid pBLcat DNA was prepared for use in subsequent constructions in substantial accordance with the procedure of Example 3.

EXAMPLE 5

Construction of Plasmid pSBLcat

About 100 μg of plasmid pBLcat DNA were dissolved in 10 μl of 10×HindIII buffer (0.5 M NaCl; 0.1 M Tris-HCl, pH=8.0; 0.1 M MgCl$_2$; and 1 mg/ml BSA) and 80 μl of H$_2$O. About 10 μl (about 100 units) of restriction enzyme HindIII were added to the solution of plasmid pBLcat DNA, and the resulting reaction was incubated at 37° C. for 2 hours. The HindIII-digested plasmid pBLcat DNA was loaded onto an agarose gel and electrophoresed until the ~0.87 kb HindIII restriction fragment that comprises the BK enhancer and Ad2 late promoter was well separated from the other digestion products; then, the ~0.87 kb fragment was isolated and prepared for ligation in substantial accordance with the procedure of Example 4A. About 10 μg of the desired fragment were obtained and dissolved in 50 μl of TE buffer.

About 1 μg of plasmid pSV2cat DNA in 1 μl of TE buffer was dissolved in 2 μl of 10×HindIII buffer and 16 μl of H$_2$O. About 1 μl (about 10 units) of restriction enzyme HindIII was added to the solution of DNA, and the resulting reaction was incubated at 37° C. for 2 hours. The reaction was stopped by extracting the reaction mixture first with phenol, then twice with chloroform. The HindIII-digested plasmid pSV2cat DNA was precipitated with ethanol and resuspended in 100 μl of TE buffer. The HindIII-digested plasmid pSV2cat DNA was treated with calf-intestinal alkaline phosphatase in substantial accordance with the procedure of Example 2 and then resuspended in 10 μl of TE buffer.

About 5 μl of the ~0.87 kb HindIII restriction fragment of plasmid pBLcat were added to the 10 μl of HindIII-digested plasmid pSV2cat, and then, 3 μl of 10×ligase buffer, 2 μl (about 1000 units) of T4 DNA ligase, and 13 μl of H$_2$O were added to the solution of DNA, and the resulting reaction was incubated at 16° C. for 2 hours. The ligated DNA constituted the desired plasmid pSBLcat. The ligated DNA was used to transform *E. coli* K12 HB101 in substantial accordance with the procedure of Example 3. The transformed cells were plated on L agar containing ampicillin, and the plasmid DNA of the ampicillin-resistant transformants was examined by restriction enzyme analysis to identify the *E. coli* K12 HB101/pSBLcat transformants. The ~0.87 kb HindIII restriction fragment that encodes the BK enhancer and Ad2 late promoter could insert into HindIII-digested plasmid pSBLcat in one of two orientations, only one of which yields plasmid pSBLcat. A restriction site and function map of plasmid pSBLcat is presented in FIG. 8 of the accompanying drawings.

EXAMPLE 6

Construction of Plasmid pL133

A. Construction of Intermediate Plasmid pSV2-HPC8

Plasmid pHC7 comprises a DNA sequence that encodes human protein C. One liter of L-broth containing 15 μg/ml tetracycline was inoculated with a culture of *E. coli* K12 RR1/pHC7 (NRRL B-15926), and plasmid pHC7 DNA was isolated and purified in substantial accordance with the procedure of Example 3. About 1 mg of plasmid pHC7 DNA was obtained by this procedure, suspended in 1 ml of TE buffer, and stored at −20° C. A restriction site and function map of plasmid pHC7 is presented in FIG. 9 of the accompanying drawings.

Fifty μl of the plasmid pHC7 DNA were mixed with 5 μl (~50 units) of restriction enzyme BanI, 10 μl of 10×BanI reaction buffer (1.5 M NaCl; 60 mM Tris-HCl, pH=7.9; 60 mM MgCl$_2$; and 1 mg/ml BSA), and 35 μl of H$_2$O and incubated until the digestion was complete. The BanI-digested plasmid pHC7 DNA was then electrophoresed on a 3.5% polyacrylamide gel (29:1, acrylamide:bisacrylamide), until the ~1.25 kb BanI restriction fragment was separated from the other digestion products.

The region of the gel containing the ~1.25 kb BanI restriction fragment was cut from the gel, placed in a test tube, and broken into small fragments. One ml of extraction buffer (500 mM NH$_4$OAc, 10 mM MgOAc, 1 mM EDTA, 1% SDS, and 10 mg/ml tRNA) was added to the tube containing the fragments, and the tube was placed at 37° C. overnight. Centrifugation was used to pellet the debris, and the supernatant was transferred to a new tube. The debris was washed once with 200 μl of extraction buffer; the wash supernatant was combined with the first supernatant from the overnight extraction. After passing the supernatant through a plug of glass wool, two volumes of ethanol were added to and mixed with the supernatant. The resulting solution was placed in a dry ice-ethanol bath for ~10 minutes, and then, the DNA was pelleted by centrifugation.

Approximately 8 μg of the ~1.25 kb BanI restriction fragment were obtained by this procedure. The purified fragment was suspended in 10 μl of TE buffer and stored at −20° C. The BanI restriction fragment had to be modified by the addition of a linker to construct plasmid pSV2-HPC8. The DNA fragments used in the construction of the linker were synthesized either by using a Systec 1450A DNA Synthesizer (Systec Inc., 3816 Chandler Drive, Minneapolis, Minn.) or an ABS 380A DNA Synthesizer (Applied Biosystems, Inc., 850 Lincoln Centre Drive, Foster City, Calif. 94404). Many DNA synthesizing instruments are known in the art and can be used to make the fragments. In addition, the fragments can also be conventionally prepared in substantial accordance with the procedures of Itakura et al., 1977, Science, 198:1056 and Crea et al., 1978, Proc. Nat. Acad. Sci. USA, 75:5765.

Five hundred picomoles of each single strand of the linker were kinased in 20 μl of reaction buffer, which contained 15 units (~0.5 μl) T4 polynucleotide kinase, 2 μl 10×ligase buffer, 10 μl of 500 μM ATP, and 7.5 μl of H$_2$O. The kinase reaction was incubated at 37° C. for 30 minutes, and the reaction was terminated by incubation at 100° C. for 10 minutes. In order to ensure complete kination, the reaction was chilled on ice, 2 μl of 0.2 M dithiothreitol, 2.5 μl of 5 mM ATP, and 15 units of T4 polynucleotide kinase were added to the reaction mixture and mixed, and the reaction mixture was incubated another 30 minutes at 37° C. The reaction was stopped by another 10 minute incubation at 100° C. and then chilled on ice.

Although kinased separately, the two single strands of the DNA linker were mixed together after the kinase reaction. To anneal the strands, the kinase reaction mixture was incubated at 100° C. for 10 minutes in a water bath containing ~150 ml of water. After this incubation, the water bath was shut off and allowed to cool to room temperature, a process taking about 3 hours. The water bath, still containing the tube of kinased DNA, was then incubated at 4° C. overnight. This process annealed the single strands. The linker constructed had the following structure:

The linker was stored at −20° C. until use.

The ~8 μg of ~1.25 kb BanI fragment were added to and mixed with the ~50 μl of linker (~500 picomoles), 1 μl of T4 DNA ligase (~500 units), 10 μl of 10×ligase buffer, and 29 μl of H$_2$O, and the resulting ligation reaction was incubated at 4° C. overnight. The ligation reaction was stopped by a 10 minute incubation at 65° C. The DNA was pelleted by adding NaOAc to a final concentration of 0.3 M, adding 2 volumes of ethanol, chilling in a dry ice-ethanol bath, and then centrifuging the solution.

The DNA pellet was dissolved in 10 μl of 10×ApaI reaction buffer (60 mM NaCl; 60 mM Tris-HCl, pH=7.4; 60 mM MgCl$_2$; and 60 mM 2-mercaptoethanol), 5 μl (~50 units) of restriction enzyme ApaI, and 85 μl of H$_2$O, and the reaction was placed at 37° C. for two hours. The reaction was then stopped and the DNA pelleted as above. The DNA pellet was dissolved in 10 μl of 10×HindIII reaction buffer, 5 μl (~50 units) of restriction enzyme HindIII, and 85 μl of H$_2$O, and the reaction was placed at 37° C. for two hours. After the HindIII digestion, the reaction mixture was loaded onto a 3.5% polyacrylamide gel, and the desired ~1.23 kb HindIII-ApI restriction fragment was isolated in substantial accordance with the procedure described in Example 4A. Approximately 5 μg of the desired fragment were obtained, suspended in 10 μl of TE buffer, and stored at −20° C.

Fifty μl of plasmid pHC7 DNA were mixed with 5 μl (~50 units) of restriction enzyme PstI, 10 μl of 10×PstI reaction buffer (1.0 M NaCl; 100 mM Tris-HCl, pH=7.5; 100 mM MgCl$_2$; and 1 mg/ml BSA), and 35 μl of H$_2$O and incubated at 37° C. for two hours. The PstI-digested plasmid pHC7 DNA was then electrophoresed on a 3.5% polyacrylamide gel, and the desired ~0.88 kb fragment was purified in substantial accordance with the procedure described above. Approximately 5 μg of the desired fragment were obtained, suspended in 10 μl of TE buffer, and stored at −20° C.

The ~5 μg of ~0.88 kb PstI fragment were added to and mixed with ~50 μl of the following linker, which was constructed on an automated DNA synthesizer:

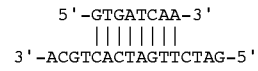

About 1 μl of T4 DNA ligase (~10 units), 10 μl 10×ligase buffer, and 29 μl H$_2$O were added to the mixture of DNA, and the resulting ligation reaction was incubated at 4° C. overnight.

The ligation reaction was stopped by a 10 minute incubation at 65° C. After precipitation of the ligated DNA, the DNA pellet was dissolved in 10 μl of 10×ApaI reaction buffer, 5 μl (~50 units) of restriction enzyme ApaI, and 85 μl of H₂O, and the reaction was placed at 37° for two hours. The reaction was then stopped and the DNA pelleted once again. The DNA pellet was dissolved in 10 μl 10×BglII reaction buffer (1 M NaCl; 100 mM Tris-HCl, pH=7.4; 100 mM MgCl₂; 100 mM 2-mercaptoethanol; and 1 mg/ml BSA), 5 μl (~50 units) of restriction enzyme BglII, and 85 μl H₂O, and the reaction was placed at 37° C. for two hours. After the BglII digestion, the reaction mixture was loaded onto a 3.5% polyacrylamide gel, and the desired ~0.19 kb ApaI-BglII restriction fragment was isolated in substantial accordance with the procedure described above. Approximately 1 μg of the desired fragment was obtained, suspended in 10 μl of TE buffer, and stored at −20° C.

Approximately 10 μg of plasmid pSV2gpt DNA (ATCC 37145) were dissolved in 10 μl of 10×HindIII reaction buffer, 5 μl (~50 units) of restriction enzyme HindIII, and 85 μl of H₂O, and the reaction was placed at 37° C. for 2 hours. The reaction mixture was then made 0.25 M in NaOAc, and after the addition of two volumes of ethanol and incubation in a dry ice-ethanol bath, the DNA was pelleted by centrifugation. The DNA pellet was dissolved in 10 μl of 10×BglII buffer, 5 μl (~50 units) of restriction enzyme BglII, and 85 μl of H₂O, and the reaction was placed at 37° C. for two hours. After the BglII digestion, the reaction mixture was loaded onto a 1% agarose gel, and the fragments were separated by electrophoresis. The gel was stained with ethidium bromide and viewed under ultraviolet light, and the band containing the desired ~5.1 kb HindIII-BglII fragment was cut from the gel and placed in dialysis tubing, and electrophoresis was continued until the DNA was out of the agarose. The buffer containing the DNA from the dialysis tubing was extracted with phenol and CHCl₃, and then, the DNA was precipitated. The pellet was resuspended in 10 μl of TE buffer and constituted ~5 μg of the desired ~5.1 kb HindIII-BglII restriction fragment of plasmid pSV2gpt.

Two μl of the ~1.23 kb HindIII-ApaI restriction fragment, 3 μl of the ~0.19 kb ApaI-BglII fragment, and 2 μl of the ~5.1 kb HindIII-BglII fragment were mixed together and then incubated with 10 μl of 10×ligase buffer, 1 μl of T4 DNA ligase (~500 units), and 82 μl of H₂O at 16° C. overnight. The ligated DNA constituted the desired plasmid pSV2-HPC8; a restriction site and function map of the plasmid is presented in FIG. 9 of the accompanying drawings.

*E. coli* K12 RR1 (NRRL B-15210) cells were made competent for transformation in substantial accordance with the procedure described in Example 2. The ligated DNA prepared above was used to transform the cells, and aliquots of the transformation mix were plated on L-agar plates containing 100 μg/ml ampicillin. The plates were then incubated at 37° C. *E. coli* K12 RR1/pSV2-HPC8 transformants were verified by restriction enzyme analysis of their plasmid DNA.

B. Final Construction of Plasmid pL133

Fifty μg of plasmid pSV2-HPC8 were dissolved in 10 μl of 10×HindIII reaction buffer, 5 μl (~50 units) of restriction enzyme HindIII, and 85 μl of H₂O, and the reaction was incubated at 37° C. for two hours. After the HindIII digestion, the DNA was precipitated, and the DNA pellet was dissolved in 10 μl 10×SalI reaction buffer (1.5 M NaCl; 60 mM Tris-HCl, pH=7.9; 60 mM MgCl₂; 60 mM 2-mercaptoethanol; and 1 mg/ml BSA), 5 μl (~50 units) of restriction enzyme SalI, and 85 μl of H₂O. The resulting SalI reaction mixture was incubated for 2 hours at 37° C. The HindIII-SalI-digested plasmid pSV2-HPC8 was loaded onto a 3.5% polyacrylamide gel and electrophoresed until the desired ~0.29 kb HindIII-SalI restriction fragment was separated from the other reaction products. The desired fragment was isolated from the gel; about 2 μg of the fragment were obtained and suspended in 10 μl of TE buffer.

Fifty μg of plasmid pSV2-HPC8 were dissolved in 10 μl of 10×BglII reaction buffer, 5 μl (50 units) of restriction enzyme BglII, and 85 μl of H₂O, and the reaction was incubated at 37° C. for two hours. After the BglII digestion, the DNA was precipitated, and the DNA pellet was dissolved in 10 μl of 10×SalI reaction buffer, 5 μl (~50 units) of restriction enzyme SalI, and 85 μl of H₂O. The resulting SalI reaction mixture was incubated for 2 hours at 37° C. The SalI-BglII-digested plasmid pSV2-HPC8 was loaded onto a 3.5% polyacrylamide gel and electrophoresed until the desired ~1.15 kb SalI-BglII restriction fragment was separated from the other reaction products. The ~1.15 kb SalI-BglII restriction fragment was isolated from the gel; about 8 μg of fragment were obtained and suspended in 10 μl of TE buffer.

Approximately 10 μg of plasmid pSV2-β-globin DNA (NRRL B-15928) were dissolved in 10 μl of 10×HindIII reaction buffer, 5 μl (~50 units) of restriction enzyme HindIII, and 85 μl of H₂O, and the reaction was placed at 37° C. for 2 hours. The reaction mixture was then made 0.25 M in NaOAc, and after the addition of two volumes of ethanol and incubation in a dry ice-ethanol bath, the DNA was pelleted by centrifugation. The HindIII-digested plasmid pSV2-β-globin was dissolved in 10 μl of 10×BglII buffer, 5 μl (~50 units) of restriction enzyme BglII, and 85 μl of H₂O, and the reaction was placed at 37° C. for two hours. After the BglII digestion, the reaction mixture was loaded onto a 1% agarose gel, and the fragments were separated by electrophoresis. The desired ~4.2 kb HindIII-BglII restriction fragment was isolated from the gel; about 5 μg of the desired fragment were obtained and suspended in 10 μl of TE buffer.

Two μl of the ~0.29 kb HindIII-SalI fragment of plasmid pSV2-HPC8, 2 μl of the ~1.15 kb SalI-BglII fragment of plasmid pSV2-HPC8, and 2 μl of the ~4.2 kb HindIII-BglII fragment of plasmid pSV2-β-globin were mixed together and ligated in substantial accordance with the procedure of Example 6A. The ligated DNA constituted the desired plasmid pL133; a restriction site and function map of plasmid pL133 is presented in FIG. 9 of the accompanying drawings. The desired *E. coli* K12 RR1/pL133 transformants were constructed in substantial accordance with the teaching of Example 6A, with the exception that plasmid pL133, rather than plasmid pSV2-HPC8, was used as the transforming DNA.

EXAMPLE 7

Construction of Plasmid pLPC

About 20 μg of plasmid pBLcat DNA were dissolved in 10 μl of 10×HindIII buffer and 80 μl of H₂O. About 10 μl (~100 units) of restriction enzyme HindIII were added to the solution of plasmid pBLcat DNA, and the resulting reaction was incubated at 37° C. for 2 hours. The HindIII-digested plasmid pBLcat DNA was loaded onto an agarose gel and electrophoresed until the ~0.87 kb HindIII restriction fragment that comprises the BK enhancer and Ad2 late promoter was separated from the other digestion products; then, the ~0.87 kb fragment was isolated and prepared for ligation in substantial accordance with the procedure of Example 4A. About 2 μg of the desired fragment were obtained and dissolved in 5 μl of TE buffer.

About 1.5 μg of plasmid pL133 DNA was dissolved in 2 μl of 10×HindIII buffer and 16 μl of H₂O. About 1 μl (~10 units) of restriction enzyme HindIII was added to the solution of DNA, and the resulting reaction was incubated at 37° C. for 2 hours. The DNA was then diluted to 100 μl with TE buffer and treated with calf-intestinal alkaline phosphatase in substantial accordance with the procedure in Example 2. The HindIII-digested plasmid pL133 DNA was extracted twice with phenol and once with chloroform, precipitated with ethanol, and resuspended in 10 μl of TE buffer.

About 5 μl of the ~0.87 kb HindIII restriction fragment of plasmid pBLcat were added to the 1.5 μl of HindIII-digested plasmid pL133, and then, 1 μl of 10×ligase buffer, 1 μl (~1000 units) of T4 DNA ligase, and 1.5 μl of H₂O were added to the solution of DNA, and the resulting reaction was incubated at 16° C. overnight. The ligated DNA constituted the desired plasmid pLPC. A restriction site and function map of plasmid PLPC is presented in FIG. 10 of the accompanying drawings.

The ligated DNA was used to transform *E. coli* K12 HB101 in substantial accordance with the procedure of Example 3. The transformed cells were plated on L agar containing ampicillin, and the plasmid DNA of the ampicillin-resistant transformants was examined by restriction enzyme analysis to identify the *E. coli* K12 HB101/pLPC transformants. The ~0.87 kb HindIII restriction fragment that encodes the BK enhancer and Ad2 late promoter could insert into HindIII-digested plasmid pL133 in one of two orientations, only one of which yields plasmid pLPC.

EXAMPLE 8

Construction of Plasmids pLPC4 and pLPC5

About 1 μg (1 μl) of the BK virus DNA prepared in Example 1 and 1 μg of plasmid pLPC (1 μl) were dissolved in 2 μl of 10×EcoRI buffer and 14 μl of H₂O. About 2 μl (~10 units) of restriction enzyme EcoRI were added to the solution of DNA, and the resulting reaction was incubated at 37° C. for 2 hours. The EcoRI-digested mixture of BK virus and plasmid pLPC DNA was extracted once with buffered phenol and once with chloroform. Then, the DNA was collected by adjusting the NaCl concentration to 0.25 M, adding two volumes of ethanol, incubating the solution in a dry ice-ethanol bath for 2 minutes, and centrifuging the solution to pellet the DNA. The supernatant was discarded, and the DNA pellet was rinsed with 70% ethanol, dried, and resuspended in 12 μl of TE buffer.

About 13 μl of H₂O and 3 μl of 10×ligase buffer were added to the EcoRI-digested mixture of BK virus and plasmid pLPC DNA. Two μl (~1000 units) of T4 DNA ligase were added to the solution of DNA, and the resulting reaction was incubated at 16° C. for 2 hours. The ligated DNA constituted the desired plasmids pLPC4 and pLPC5, which differ only with respect to the orientation of the inserted BK virus DNA. A restriction site and function map of plasmid pLPC4 is presented in FIG. 11 of the accompanying drawings.

The ligated DNA constituted the desired plasmids pLPC4 and pLPC5 and was used to transform *E. coli* K12 HB101 competent cells in substantial accordance with the procedure of Example 3. The transformed cells were plated on L agar containing 100 μg/ml ampicillin. The *E. coli* K12 HB101/pLPC4 and *E. coli* K12 HB101/pLPC5 transformants were identified by their ampicillin-resistant phenotype and by restriction enzyme analysis of their plasmid DNA.

EXAMPLE 9

Construction of Plasmids pLPChyg1 and pLPChyg2

*E. coli* K12 RR1/pSV2hyg cells are obtained from the Northern Regional Research Laboratory under the accession number NRRL B-18039. Plasmid pSV2hyg DNA is obtained from the cells in substantial accordance with the procedure of Example 3. A restriction site and function map of plasmid pSV2hyg is presented in FIG. 12 of the accompanying drawings.

About 10 μg (in 10 μl of TE buffer) of plasmid pSV2hyg were added to 2 μl of 10×BamHI buffer and 6 μl of H₂O. About 2 μl (about 20 units) of restriction enzyme BamHI were added to the solution of DNA, and the resulting reaction was incubated at 37° C. for 2 hours. The reaction was extracted first with phenol and then was extracted twice with chloroform. The BamHI-digested plasmid pSV2hyg DNA was loaded onto an agarose gel, and the hygromycin resistance gene-containing, ~2.5 kb restriction fragment was isolated in substantial accordance with the procedure described in Example 4A.

About 5 μl of 10×Klenow buffer (0.2 mM in each of the four dNTPs; 0.5 M Tris-HCl, pH=7.8; 50 mM MgCl₂; 0.1 M 2-mercaptoethanol; and 100 μg/ml BSA) and 35 μl of H₂O were added to the solution of BamHI-digested plasmid pSV2hyg DNA, and then, about 25 units of Klenow enzyme (about 5 μl, as marketed by BRL) were added to the mixture of DNA, and the resulting reaction was incubated at 16° C. for 30 minutes. The Klenow-treated, BamHI-digested plasmid pSV2hyg DNA was extracted once with phenol and once with chloroform and then precipitated with ethanol. About 2 μg of the desired fragment were obtained and suspended in 5 μl of TE buffer.

About 10 μg (10 μl) of plasmid pLPC DNA were added to 2 μl of 10×StuI buffer and 6 μl of H₂O. About 2 μl (~10 units) of restriction enzyme StuI were added to the solution of DNA, and the resulting reaction was incubated at 37° C. for 2 hours. The StuI-digested plasmid pLPC DNA was precipitated with ethanol, collected by centrifugation, and resuspended in 2 μl of 10×NdeI buffer (1.5 M NaCl; 0.1 M Tris-HCl, pH=7.8; 70 mM MgCl₂; 60 mM 2-mercaptoethanol; and 1 mg/ml BSA) and 16 μl of H₂O. About 2 μl (~10 units) of restriction enzyme NdeI were added to the solution of StuI-digested DNA, and the resulting reaction was incubated at 37° C. for 2 hours.

The NdeI-StuI-digested plasmid PLPC DNA was precipitated with ethanol, collected by centrifugation, and resuspended in 5 μl of 10×Klenow buffer and 40 μl of H₂O. About 5 μl (~25 units) of Klenow enzyme were added to the solution of DNA, and the resulting reaction was incubated at 16° C. for 30 minutes. After the Klenow reaction, the reaction mixture was loaded onto an agarose gel, and the ~5.82 kb NdeI-StuI restriction fragment was isolated from the gel. About 5 μg of the desired fragment were obtained and suspended in 5 μl of TE buffer.

About 2 μl of the ~2.5 kb Klenow-treated BamHI restriction fragment of plasmid pSV2hyg were mixed with about 1 μl of the ~5.82 kb Klenow-treated NdeI-StuI restriction fragment of plasmid pLPC, and about 3 μl of 10×ligase buffer, 2 μl of T4 DNA ligase (~1000 units), 1 μl of T4 RNA ligase (~1 unit), and 14 μl of H₂O were added to the solution of DNA. The resulting reaction was incubated at 16° C. overnight. The ligated DNA constituted the desired plasmids pLPChyg1 and pLPChyg2, which differ only with respect to the orientation of the ~2.5 kb Klenow-treated, BamHI restriction fragment of plasmid pSV2hyg. A restriction site and function map of plasmid pLPChyg1 is presented in FIG. 13 of the accompanying drawings. The ligated DNA was used to transform *E. coli* K12 HB101 in substantial accordance with the procedure of Example 3. The desired *E. coli* K12 HB101/pLPChyg1 and *E. coli* K12 HB101/pLPChyg2 transformants were plated on L agar containing ampicillin and identified by restriction enzyme analysis of their plasmid DNA.

EXAMPLE 10

Construction of Plasmid pBW32
A. Construction of Intermediate Plasmid pTPA103

Plasmid pTPA102 comprises the coding sequence of human tissue plasminogen activator (TPA). Plasmid pTPA102 can be isolated from *E. coli* K12 MM294/pTPA102, a strain available from the Northern Regional Research Laboratory under the accession number NRRL B-15834. A restriction site and function map of plasmid pTPA102 is presented in FIG. 14 of the accompanying drawings. Plasmid pTPA102 DNA is isolated from *E. coli* K12 MM294/pTPA102 in substantial accordance with the procedure of Example 2.

About 50 μg of plasmid pTPA102 (in about 50 μl of TE buffer) were added to 10 μl of 10×Tth111I buffer (0.5 M NaCl; 80 mM Tris-HCl, pH=7.4; 80 mM $MgCl_2$; 80 mM 2-mercaptoethanol; and 1 mg/ml BSA) and 80 μl of $H_2O$. About 10 μl (~50 units) of restriction enzyme Tth111I were added to the solution of DNA, and the resulting reaction was incubated at 65° C. for 2 hours. The reaction mixture was loaded onto an agarose gel, and the ~4.4 kb Tth111I restriction fragment that comprises the TPA coding sequence was isolated from the gel. The other digestion products, 3.1 kb and 0.5 kb restriction fragments, were discarded. About 10 μg of the desired ~4.4 kb Tth111I restriction fragment were obtained and suspended in 10 μl of TE buffer.

About 5 μl of 10×Klenow buffer and 30 μl of $H_2O$ were added to the solution comprising the ~4.4 kb Tth111I restriction fragment, and after the further addition of about 5 μl of Klenow enzyme (~5 units), the reaction mixture was incubated at 16° C. for 30 minutes. After the Klenow reaction, the DNA was precipitated with ethanol and resuspended in 3 μl of 10×ligase buffer and 14 μl of $H_2O$.

BamHI linkers (New England Biolabs), which had the following sequence:

```
5'-CGGATCCG-3'
   ||||||||
3'-GCCTAGGC-5',
``` were kinased and prepared for ligation by the following procedure. Four μl of linkers (~2 μg) were dissolved in 20.15 μl of $H_2O$ and 5 μl of 10×kinase buffer (500 mM Tris-HCl, pH=7.6 and 100 mM $MgCl_2$), incubated at 90° C. for two minutes, and then cooled to room temperature. Five μl of γ-$^{32}$P-ATP (~20 μCi), 2.5 μl of 1 M DTT, and 5 μl of polynucleotide kinase (~10 units) were added to the mixture, which was then incubated at 37° C. for 30 minutes. Then, 3.35 μl of 0.01 M ATP and 5 μl of kinase were added, and the reaction was continued for another 30 minutes at 37° C. The radioactive ATP aids in determining whether the linkers have ligated to the target DNA.

About 10 μl of the kinased BamHI linkers were added to the solution of ~4.4 kb Tth111I restriction fragment, and after the addition of 2 μl of T4 DNA ligase (~1000 units) and 1 μl of T4 RNA ligase (~2 units), the ligation reaction was incubated overnight at 4° C. The ligated DNA was precipitated with ethanol and resuspended in 5 μl of 10×HindIII buffer and 40 μl of $H_2O$. About 5 μl (~50 units) of restriction enzyme HindIII were added to the solution of DNA, and the resulting reaction was incubated at 37° C. for 2 hours.

The HindIII-digested DNA was precipitated with ethanol and resuspended in 10 μl of 10×BamHI buffer and 90 μl of $H_2O$. About 10 μl (~100 units) of restriction enzyme BamHI were added to the solution of DNA, and the resulting reaction was incubated at 37° C. for 2 hours. After the BamHI digestion, the reaction mixture was loaded onto an agarose gel, and the ~2.0 kb BamHI-HindIII restriction fragment was isolated from the gel. About 4 μg of the desired fragment were obtained and suspended in about 5 μl of TE buffer.

To construct plasmid pTPA103, the ~2.0 kb BamHI-HindIII restriction fragment derived from plasmid pTPA102 was inserted into BamHI-HindIII-digested plasmid pRC. Plasmid pRC was constructed by inserting an ~288 bp EcoRI-ClaI restriction fragment that comprises the promoter and operator (trpPO) sequences of the *E. coli* trp operon into EcoRI-ClaI-digested plasmid pKC7. Plasmid pKC7 can be obtained from the American Type Culture Collection in *E. coli* K12 N100/pKC7 under the accession number ATCC 37084. The ~288 bp EcoRI-ClaI restriction fragment that comprises the trpPO can be isolated from plasmid pTPA102, which can be isolated from *E. coli* K12 MM294/pTPA102 (NRRL B-15834). Plasmid pKC7 and plasmid pTPA102 DNA can be obtained from the aforementioned cell lines in substantial accordance with the procedure of Example 3. This ~0.29 kb EcoRI-ClaI restriction fragment of plasmid pTPA102 comprises the transcription activating sequence and most of the translation activating sequence of the *E. coli* trp gene and has the sequence depicted below:

```
             10         20         30         40         50
5'-AATTCACGCT GTGGTGTTAT GGTCGGTGGT CGCTAGGGTG CCGACGCGCA
   |||||| |||||||||| |||||||||| |||||||||| ||||||||||
3'-GTGCGA CACCACAATA CCAGCCACCA GCGATCCCAC GGCTGCGCGT 60         70         80         90        100
   TCTCGACTGC ACGGTGCACC AATGCTTCTG GCGTCAGGCA GCCAATCGGA
   |||||||||| |||||||||| |||||||||| |||||||||| ||||||||||
   AGAGCTGACG TGCCACGTGG TTACGAAGAC CGCAGTCCGT CGGTTAGCCT 110        120        130        140        150
   AGCTGTGGTA TGGCTGTGCA GGTCGTATAA TCACCGCATA ATTCGAGTCG
   |||||||||| |||||||||| |||||||||| |||||||||| ||||||||||
   TCGACACCAT ACCGACACGT CCAGCATATT AGTGGCGTAT TAAGCTCAGC
```

-continued

```
            160         170         180         190         200
       CTCAAGGCGC  ACTCCCGTTC  CGGATAATGT  TTTTTGCTCC  GACATCATAA
       ||||||||||  ||||||||||  ||||||||||  ||||||||||  ||||||||||
       GAGTTCCGCG  TGAGGGCAAG  GCCTATTACA  AAAAACGAGG  CTGTAGTATT 210         220         230         240         250
       CGGTTCCGGC  AAATATTCTG  AAATGAGCTG  TTGACAATTA  ATCATCGAAC
       ||||||||||  ||||||||||  ||||||||||  ||||||||||  ||||||||||
       GCCAAGGCCG  TTTATAAGAC  TTTACTCGAC  AACTGTTAAT  TAGTAGCTTG 260         270         280     287
       TAGTTAACTA  GTACGCAAGT  TCTCGTAAAA  AGGGTAT-3'
       ||||||||||  ||||||||||  ||||||||||  |||||||
       ATCAATTGAT  CATGCGTTCA  AGAGCATTTT  TCCCATAGC-5'
```

Thus, to construct plasmid pRC, about 2 μg of plasmid pKC7 in 10 μl of TE buffer were added to 2 μl of 10×ClaI buffer (0.5 M NaCl; 60 mM Tris-HCl, pH=7.9, 60 mM MgCl$_2$; and 1 mg/ml BSA) and 6 μl of H$_2$O. About 2 μl (~10 units) of restriction enzyme ClaI were added to the solution of plasmid pKC7 DNA, and the resulting reaction was incubated at 37° C. for 2 hours. The ClaI-digested plasmid pKC7 DNA was precipitated with ethanol and resuspended in 2 μl of 10×EcoRI buffer and 16 μl of H$_2$O. About 2 μl (~10 units) of restriction enzyme EcoRI were added to the solution of ClaI-digested plasmid pKC7 DNA, and the resulting reaction was incubated at 37° C. for 2 hours.

The EcoRI-ClaI-digested plasmid pKC7 DNA was extracted once with phenol and then twice with chloroform. The DNA was then precipitated with ethanol and resuspended in 3 μl of 10×ligase buffer and 20 μl of H$_2$O. A restriction site and function map of plasmid pKC7 can be obtained from Maniatis et al., Molecular Cloning (Cold Spring Harbor Laboratory, 1982), page 8.

About 20 μg of plasmid pTPA102 in about 20 μl of TE buffer were added to 10 μl of 10×ClaI buffer and 60 μl of H$_2$O. About 10 μl (~50 units) of restriction enzyme ClaI were added to the solution of plasmid pTPA102 DNA, and the resulting reaction was incubated at 37° C. for 2 hours. The ClaI-digested plasmid pTPA102 DNA was precipitated with ethanol and resuspended in 10 μl of 10×EcoRI buffer and 80 μl of H$_2$O. About 10 μl (~50 units) of restriction enzyme EcoRI were added to the solution of ClaI-digested plasmid pTPA102 DNA, and the resulting reaction was incubated at 37° C. for 2 hours.

The EcoRI-ClaI-digested plasmid pTPA102 DNA was extracted once with phenol, loaded onto a 7% polyacrylamide gel, and electrophoresed until the ~288 bp EcoRI-ClaI restriction fragment that comprises the trpPO was separated from the other digestion products. The ~288 bp EcoRI-ClaI restriction fragment was isolated from the gel; about 1 μg of the desired fragment was obtained, suspended in 5 μl of TE buffer, and added to the solution of EcoRI-ClaI-digested plasmid pKC7 DNA prepared as described above. About 2 μl (~1000 units) of T4 DNA ligase were then added to the mixture of DNA, and the resulting ligation reaction was incubated at 16° C. for 2 hours. The ligated DNA constituted the desired plasmid pRC DNA.

The ligated DNA was used to transform E. coli K12 HB101 competent cells in substantial accordance with the procedure of Example 2. The transformed cells were plated on L agar containing 100 μg/ml ampicillin, and the ampicillin-resistant transformants were screened by restriction enzyme analysis of their plasmid DNA to identify the desired E. coli K12 HB101/pRC colonies. Plasmid pRC DNA was obtained from the E. coli K12 HB101/pRC transformants in substantial accordance with the procedure of Example 3.

About 2 μg of plasmid pRC DNA in 2 μl of TE buffer were added to 2 μl of 10×HindIII buffer and 16 μl of H$_2$O. About 2 μl (~10 units) of restriction enzyme HindIII were added to the solution of plasmid pRC DNA, and the resulting reaction was incubated at 37° C. for two hours. The HindIII-digested plasmid pRC DNA was precipitated with ethanol and resuspended in 2 μl of 10×BamHI buffer and 16 μl of H$_2$O. About 2 μl (~10 units) of restriction enzyme BamHI were added to the solution of HindIII-digested plasmid pRC DNA, and the resulting reaction was incubated at 37° C. for 2 hours.

The BamHI-HindIII-digested plasmid pRC DNA was extracted once with phenol and then twice with chloroform. The DNA was precipitated with ethanol and resuspended in 3 μl of 10×ligase buffer and 20 μl of H$_2$O. The ~4 μg (in ~5 μl of TE buffer) of ~2.0 kb HindIII-BamHI restriction fragment of plasmid pTPA102 were then added to the solution of BamHI-HindIII-digested plasmid pRC DNA. About 2 μl (~1000 units) of T4 DNA ligase were added to the mixture of DNA, and the resulting reaction was incubated at 16° C. for 2 hours. The ligated DNA constituted the desired plasmid pTPA103 DNA.

To reduce undesired transformants, the ligated DNA was digested with restriction enzyme NcoI, which cuts plasmid pRC but not plasmid pTPA103. Thus, digestion of the ligated DNA with NcoI reduces undesired transformants, because linearized DNA transforms E. coli at a lower frequency than closed, circular DNA. To digest the ligated DNA, the DNA was first precipitated with ethanol and then resuspended in 2 μl of 10×NcoI buffer (1.5 M NaCl; 60 mM Tris-HCl, pH=7.8; 60 mM MgCl$_2$; and 1 mg/ml BSA) and 16 μl of H$_2$O. About 2 μl (~10 units) of restriction enzyme NcoI were added to the solution of DNA, and the resulting reaction was incubated at 37° C. for 2 hours.

The ligated and then NcoI-digested DNA was used to transform E. coli K12 RV308 (NRRL B-15624). E. coli K12 RV308 cells were made competent and transformed in substantial accordance with the procedure of Example 3. The transformation mixture was plated on L agar containing 100 μg/ml ampicillin. The ampicillin-resistant transformants were tested for sensitivity to kanamycin, for though plasmid pRC confers kanamycin resistance, plasmid pTPA103 does not. The ampicillin-resistant, kanamycin-sensitive transformants were then used to prepare plasmid DNA, and the plasmid DNA was examined by restriction enzyme analysis to identify the E. coli K12 RV308/pTPA103 transformants. A restriction site and function map of plasmid pTPA103 is presented in FIG. 14 of the accompanying drawings. Plasmid pTPA103 DNA was isolated from the E. coli K12 RV308/pTPA103 cells in substantial accordance with the procedure of Example 3.

B. Construction of Intermediate Plasmid pBW25

About 1 μg of plasmid pTPA103 DNA in 1 μl of TE buffer was added to 2 μl of 10×BglII buffer and 16 μl of H$_2$O.

About 1 μl (~5 units) of restriction enzyme BglII was added to the solution of plasmid pTPA103 DNA, and the resulting reaction was incubated at 37° C. for 2 hours. The BglII-digested plasmid pTPA103 DNA was precipitated with ethanol and resuspended in 5 μl of 10×Klenow buffer and 44 μl of H₂O. About 1 μl of Klenow enzyme (~1 unit) was added to the solution of BglII-digested plasmid pTPA103 DNA, and the resulting reaction was incubated at 16° C. for 2 hours. The Klenow-treated, BglII-digested plasmid pTPA103 DNA was precipitated with ethanol and resuspended in 3 μl of 10×ligase buffer and 22 μl of H₂O.

About 2 μl (0.2 μg) of unkinased NdeI linkers (New England Biolabs) of sequence:

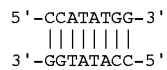

were added to the solution of Klenow-treated, BglII-digested plasmid pTPA103 DNA, together with 2 μl (~1000 units) of T4 DNA ligase and 1 μl (~2 units) of T4 RNA ligase, and the resulting ligation reaction was incubated at 4° C. overnight. The ligated DNA constituted plasmid pTPA103derNdeI, which is substantially similar to plasmid pTPA103, except plasmid pTPA103derNdeI has an NdeI recognition sequence where plasmid pTPA103 has a BglII recognition sequence.

The ligated DNA was used to transform *E. coli* K12 RV308 competent cells in substantial accordance with the procedure described in Example 2. The transformed cells were plated on L-agar containing ampicillin, and the *E. coli* K12 RV308/pTPA103derNdeI transformants were identified by restriction enzyme analysis of their plasmid DNA. Plasmid pTPA103derNdeI DNA was isolated from the transformants for use in subsequent constructions in substantial accordance with the procedure of Example 3.

About 10 μg of plasmid pTPA103derNdeI DNA in 10 μl of TE buffer were added to 2 μl of 10×AvaII buffer (0.6 M NaCl; 60 mM Tris-HCl, pH=8.0; 0.1 M MgCl₂; 60 mM 2-mercaptoethanol; and 1 mg/ml BSA) and 6 μl of H₂O. About 2 μl (~10 units) of restriction enzyme AvaII were added to the DNA, and the resulting reaction was incubated at 37° C. for 2 hours. The AvaII-digested DNA was loaded onto an agarose gel and electrophoresed until the ~1.4 kb restriction fragment was separated from the other digestion products. The ~1.4 kb AvaII restriction fragment of plasmid pTPA103derNdeI was isolated from the gel; about 2 μg of the desired fragment were obtained and suspended in 5 μl of TE buffer.

About 5 μl of 10×Klenow buffer, 35 μl of H₂O, and 5 μl (~5 units) of Klenow enzyme were added to the solution of ~1.4 kb AvaII restriction fragment, and the resulting reaction was incubated at 16° C. for thirty minutes. The Klenow-treated DNA was precipitated with ethanol and resuspended in 3 μl of 10×ligase buffer and 14 μl of H₂O.

About 2 μg of HpaI linkers of sequence:

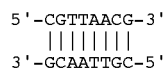

were kinased in substantial accordance with the procedure of Example 10A. About 10 μl of the kinased linkers were added to the solution of Klenow-treated, ~1.4 kb AvaII restriction fragment of plasmid pTPA103derNdeI together with 2 μl (~1000 units) of T4 DNA ligase and 1 μl (~1 unit) of T4 RNA ligase, and the resulting reaction was incubated at 16° C. overnight.

The ligated DNA was extracted once with phenol, extracted twice with chloroform, precipitated with ethanol, and resuspended in 2 μl of 10×EcoRI buffer and 16 μl of H₂O. About 2 μl (~10 units) of restriction enzyme EcoRI were added to the solution of DNA, and the resulting reaction was incubated at 37° C. for 2 hours. The EcoRI-digested DNA was extracted once with phenol, extracted twice with chloroform, precipitated with ethanol, and resuspended in 3 μl of 10×ligase buffer and 20 μl of H₂O. The fragment, which is about 770 bp in size and encodes the trpPO and the amino-terminus of TPA, thus prepared had one EcoRI-compatible end and one blunt end and was ligated into EcoRI-SmaI-digested plasmid pUC19 to form plasmid pUC19TPAFE.

About 2 μl of plasmid pUC19 (available from Bethesda Research Laboratories) were dissolved in 2 μl of 10×SmaI buffer (0.2 M KCl; 60 mM Tris-HCl, pH=8.0; 60 MM MgCl₂; 60 mM 2-mercaptoethanol; and 1 mg/ml BSA) and 16 μl of H₂O. About 2 μl (~10 units) of restriction enzyme SmaI were added to the solution of DNA, and the resulting reaction was incubated at 25° C. for 2 hours. The SmaI-digested plasmid pUC19 DNA was precipitated with ethanol, collected by centrifugation, and resuspended in 2 μl of 10×EcoRI buffer and 16 μl of H₂O. About 2 μl (~10 units) of restriction enzyme EcoRI were added to the solution of SmaI-digested plasmid pUC19 DNA, and the resulting reaction was incubated at 37° C. for 2 hours. The EcoRI-SmaI-digested plasmid pUC19 DNA was extracted once with phenol, extracted twice with chloroform, and resuspended in 5 μl of TE buffer.

The EcoRI-SmaI-digested plasmid pUC19 DNA was added to the solution containing the ~770 bp EcoRI-blunt end restriction fragment derived from plasmid pTPA103derNdeI. About 2 μl (~1000 units) of T4 DNA ligase were added to the mixture of DNA, and the resulting reaction was incubated at 16° C. overnight. The ligated DNA constituted the desired plasmid pUC19TPAFE. A restriction site and function map of plasmid pUC19TPAFE is presented in FIG. 14 of the accompanying drawings.

The multiple-cloning site of plasmid pUC19, which comprises the EcoRI and SmaI recognition sequences utilized in the construction of plasmid pUC19TPAFE, is located within the coding sequence for the lacZ α fragment. Expression of the lacZ α fragment in cells that contain the lacZ ΔM15 mutation, a mutation in the lacZ gene that encodes β-galactosidase, allows those cells to express a functional β-galactosidase molecule and thus allows those cells to hydrolyze X-Gal (5-bromo-4-chloro-3-indolyl-β-D-galactopyranoside), a colorless compound, to its indigo-colored hydrolysis product. Insertion of DNA into the multiple-cloning site of plasmid pUC19 interrupts the coding sequence for the lacZ α fragment, and cells with the lacZ ΔM15 mutation that host such a plasmid are unable to hydrolyze X-Gal (this same principle is utilized when cloning into plasmid pUC8; see Example 2). The ligated DNA that constituted plasmid pUC19TPAFE was used to transform *E. coli* K12 RR1ΔM15 (NRRL B-15440) cells made competent for transformation in substantial accordance with the procedure of Example 2.

The transformed cells were plated on L agar containing 100 μg/ml ampicillin; 40 μg/ml X-Gal; and 1 mM IPTG. Colonies that failed to exhibit the indigo color were subcultured and used to prepare plasmid DNA; the *E. coli* K12 RR1ΔM15/pUC19TPAFE transformants were identified by restriction enzyme analysis of their plasmid DNA. Plasmid pUC19TPAFE DNA was isolated from the *E. coli* K12 RR1ΔM15/pUC19TPAFE cells for use in subsequent constructions in substantial accordance with the procedure of Example 3.

About 7 μg of plasmid pUC19TPAFE in 20 μl of TE buffer were added to 10 μl of 10×HpaI buffer (0.2 M KCl; 0.1 M Tris-HCl, pH=7.4; and 0.1 M MgCl$_2$) and 70 μl of H$_2$O. About 3 μl (~6 units) of restriction enzyme HpaI were added to the solution of plasmid pUC19TPAFE DNA, and the resulting reaction was incubated at 37° C. for 20 minutes; the short reaction period was designed to yield a partial HpaI digest. The reaction was adjusted to 150 μl of 1×BamHI buffer (150 mM NaCl; 10 mM Tris-HCl, pH=8.0; and 10 mM MgCl$_2$; raising the salt concentration inactivates HpaI). About 1 μl (~16 units) of restriction enzyme BamHI were added to the solution of partially-HpaI-digested DNA, and the resulting reaction was incubated at 37° C. for 90 minutes.

The BamHI-partially-HpaI-digested plasmid pUC19TPAFE DNA was concentrated by ethanol precipitation, loaded onto a 1.5% agarose gel, and the ~3.42 kb HpaI-BamHI restriction fragment that comprises the replicon, β-lactamase gene, and all of the TPA-encoding DNA of plasmid pUCATPAFE was isolated from the gel by cutting out the segment of the gel that contained the desired fragment, freezing the segment, and then squeezing the liquid from the segment. The DNA was precipitated from the liquid by an ethanol precipitation. About 1 μg of the desired fragment was obtained and suspended in 20 μl of TE buffer.

About 10 μg of plasmid pTPA103 in 10 μl of TE buffer were dissolved in 10 μl of 10×ScaI buffer (1.0 M NaCl; 60 mM Tris-HCl, pH=7.4; and 60 mM MgCl$_2$) 10 mM DTT; and 1 mg/ml BSA) and 80 μl of H$_2$O. About 3 μl (~18 units) of restriction enzyme ScaI were added to the solution of plasmid pTPA103 DNA, and the resulting reaction was incubated at 37° C. for 90 minutes. The reaction volume was adjusted to 150 μl of 1×BamHI buffer, and about 1 μl (~16 units) of restriction enzyme BamHI was added to the mixture, which was then incubated at 37° C. for 90 minutes. The DNA was precipitated with ethanol, collected by centrifugation, and resuspended in preparation for electrophoresis. The ScaI-BamHI-digested plasmid pTPA103 DNA was loaded onto a 1.5% agarose gel and electrophoresed until the ~1.015 kb ScaI-BamHI restriction fragment was separated from the other digestion products. The ~1.015 ScaI-BamHI restriction fragment that comprises the TPA carboxy-terminus-encoding DNA of plasmid pTPA103 was isolated from the gel; about 0.5 μg of the desired fragment were obtained and dissolved in 20 μl of glass-distilled H$_2$O.

About 2 μl of the ~3.42 kb BamHI-HpaI restriction fragment of plasmid pUC19TPAFE were added to 2 μl of the ~1.015 kb ScaI-BamHI restriction fragment of plasmid pTPA103 together with 2 μl of 10×ligase buffer and 1 μl (~1 Weiss unit; the ligase was obtained from Promega Biotec, 2800 S. Fish Hatchery Road, Madison, Wis. 53711) of T4 DNA ligase, and the resulting reaction was incubated at 16° C. overnight. The ligated DNA constituted the desired plasmid pBW25. A restriction site and function map of plasmid pBW25 is presented in FIG. 14 of the accompanying drawings.

The ligated DNA was used to transform *E. coli* K12 JM105 (available from BRL) that were made competent for transformation in substantial accordance with the procedure of Example 2, except that 50 mM CaCl$_2$ was used in the procedure. The transformed cells were plated on BHI (Difco Laboratories, Detroit, Mich.) containing 100 μg/ml ampicillin, and the *E. coli* K12 JM105/pBW25 transformants were identified by restriction enzyme analysis of their plasmid DNA. Digestion of plasmid pBW25 with restriction enzyme EcoRI yields ~3.38 kb and ~1.08 kb restriction fragments. Plasmid pBW25 is prepared for use in subsequent constructions in substantial accordance with the procedure of Example 3.

C. Site-Specific Mutagenesis of the TPA Coding Region and Construction of Plasmid pBW28

About 5 μg of plasmid pBW25 in 10 μl of glass-distilled H$_2$O were added to about 10 μl of 10×HindIII reaction buffer and 80 μl of H$_2$O. About 1 μl (~20 units) of restriction enzyme HindIII was added to the solution of plasmid pBW25 DNA, and the resulting reaction was incubated at 37° C. for 90 minutes. About 3 μl (~24 units) of restriction enzyme EcoRI and 10 μl of 1M Tris.HCl, pH=7.6, were added to the solution of HindIII-digested plasmid pBW25 DNA, and the resulting reaction was incubated at 37° C. for 90 minutes. The EcoRI-HindIII-digested plasmid pBW25 DNA was concentrated by ethanol precipitation, loaded onto a 1.5% agarose gel, and electrophoresed until the ~810 bp EcoRI-HindIII restriction fragment was separated from the other digestion products. About 0.5 μg of the ~810 bp EcoRI-HindIII restriction fragment was isolated from the gel, prepared for ligation, and resuspended in 20 μl of glass-distilled H$_2$O.

About 4.5 μg of the replicative form (RF) of M13mp8 DNA (available from New England Biolabs) in 35 μl of glass-distilled H$_2$O were added to 10 μl of 10×HindIII buffer and 55 μl of H$_2$O. About 1 μl (~20 units) of restriction enzyme HindIII was added to the solution of M13mp8 DNA, and the resulting reaction was incubated at 37° C. for 1 hour. About 3 μl (~24 units) of restriction enzyme EcoRI and about 10 μl of 1M Tris.HCl, pH=7.6, were added to the solution of HindIII-digested M13mp8 DNA, and the resulting reaction was incubated at 37° C. for 1 hour. The HindIII-EcoRI-digested M13mp8 DNA was collected by ethanol precipitation, resuspended in preparation for agarose gel electrophoresis, and the large restriction fragment isolated by gel electrophoresis. About 1 μg of the large EcoRI-HindIII restriction fragment of M13mp8 was obtained and suspended in 20 μl of glass-distilled H$_2$O. About 2 μl of the large EcoRI-HindIII restriction fragment of M13mp8, 2 μl of 10×ligase buffer, 12 μl of H$_2$O and ~1 μl (~1 Weiss unit) of T4 DNA ligase were added to 3 μl of the ~810 bp EcoRI-HindIII restriction fragment of plasmid pBW25, and the resulting ligation reaction was incubated at 16° C. overnight.

*E. coli* JM103 cells, available from BRL, were made competent and transfected with the ligation mix in substantial accordance with the procedure described in the BRL M13 Cloning/'Dideoxyl' Sequencing Instruction Manual, except that the amount of DNA used per transfection was varied. Recombinant plaques were identified by insertional inactivation of the β-galactosidase α-fragment-encoding gene, which results in the loss of the ability to cleave X-gal to its indigo-colored cleavage product. For screening purposes, six white plaques were picked into 2.5 ml of L broth, to which was added 0.4 ml of *E. coli* K12 JM103, cultured in minimal media stock to insure retention of the F episome that carries proAB, in logarithmic growth phase. The plaque-containing solutions were incubated in an air-shaker at 37° C. for 8 hours. Cells from 1.5 ml aliquots were pelleted and RF DNA isolated in substantial accordance with the alkaline miniscreen procedure of Birnboim and Doly, 1979, Nuc. Acids Res. 7:1513. The remainder of each culture was stored at 4° C. for stock. The desired phage, designated pM8BW26, contained the ~810 bp EcoRI-HindIII restriction fragment of plasmid pBW25 ligated to the ~7.2 kb EcoRI-HindIII restriction fragment of M13mp8.

About fifty ml of log phase *E. coli* JM103 were infected with pM8BW26 and incubated in an air-shaker at 37° C. for 18 hours. The infected cells were pelleted by low speed centrifugation, and single-stranded pM8BW26 DNA was prepared from the culture supernatant by scaling up the procedure given in the Instruction manual. Single-stranded pM8BW26 was mutagenized in substantial accordance with the teaching of Adelman et al., 1983, DNA 2(3): 183–193, except that the Klenow reaction was done at room temperature for 30 minutes, then at 37° C. for 60 minutes, then at 10° C. for 18 hours. In addition, the S1 treatment was done at 20° C., the salt concentration of the buffer was one-half that recommended by the manufacturer, and the M13 sequencing primer (BRL) was used. The synthetic oligodeoxyribonucleotide primer used to delete the coding sequence for amino acid residues 87 through 261 of native TPA was

5'-GGGAAGTGCTGTGAAATATCCACCTGCGGCCT GAGA-3'.

The resulting mutagenesis mix was used to transfect E. coli K12 JM103 in substantial accordance with the infection procedure described above. Desired mutants were identified by restriction enzyme analysis of RF DNA and by Maxam and Gilbert DNA sequencing. The desired mutant, which had the coding sequence for amino acid residues 87 through 261 of native TPA deleted, was designated pM8BW27.

To construct plasmid pBW28, a variety of DNA fragments are needed. The first of these fragments was obtained by adding ~20 µg of RF pM8BW27 DNA in 20 µl of glass-distilled H$_2$O to 10 µl of 10×NdeI buffer and 60 µl of H$_2$O. About 10 µl (~50 units) of restriction enzyme NdeI were added to the mixture of plasmid pM8BW27 DNA, and the resulting reaction was incubated at 37° C. for two hours. The NdeI-digested plasmid pM8BW27 DNA was precipitated with ethanol, collected by centrifugation, and resuspended in 10 µl of 10×EcoRI buffer and 90 µl of H$_2$O. About 10 µl (~50 units) of restriction enzyme EcoRI were added to the solution of NdeI-digested plasmid pM8BW27 DNA, and the resulting reaction was incubated at 37° C. for 2 hours. The EcoRI-NdeI-digested plasmid pM8BW27 DNA was electrophoresed on an agarose gel until the ~560 bp NdeI-EcoRI restriction fragment, which contains the portion of TPA coding sequence that spans the site of deletion, was separated from the other digestion products. The ~560 bp NdeI-EcoRI restriction fragment was isolated from the gel; about 0.5 µg of the desired fragment was obtained and suspended in 20 µl of glass-distilled H$_2$O.

The second fragment needed to construct plasmid pBW28 is synthesized one strand at a time on an automated DNA synthesizer. The two complementary strands, which will hybridize to form a double-stranded DNA segment with XbaI and NdeI overlaps, are kinased and annealed in substantial accordance with the procedure of Example 6A. The linker has the following structure:

The third fragment needed to construct plasmid pBW28 was prepared by adding ~20 µg of plasmid pTPA103 in 20 µl of TE buffer to 10 µl of 10×BamHI buffer and 60 µl of H$_2$O. About 10 µl (~50 units) of restriction enzyme BamHI were added to the solution of plasmid pTPA103 DNA, and the resulting reaction was incubated at 37° C. for 2 hours. The BamHI-digested plasmid pTPA103 DNA was precipitated with ethanol, collected by centrifugation, and resuspended in 10 µl of 10×EcoRI buffer and 80 µl of H$_2$O. About 10 µl (~50 units) of restriction enzyme EcoRI were added to the solution of BamHI-digested plasmid pTPA103 DNA, and the resulting reaction was incubated at 37° C. for 2 hours. The BamHI-EcoRI-digested plasmid pTPA103 DNA was loaded onto an agarose gel and electrophoresed until the ~689 bp EcoRI-BamHI restriction fragment, which comprises the coding sequence for the carboxy-terminus of TPA, was separated from the other digestion products. About 0.5 µg of the ~689 bp fragment was isolated from the gel and then resuspended in 10 µl of glass-distilled H$_2$O.

The final fragment necessary to construct plasmid pBW28 was isolated from plasmid pL110, which is a plasmid disclosed and claimed in U.S. patent application Ser. No. 769,221, filed Aug. 26, 1985, attorney docket number X-6638. A restriction site and function map of plasmid pL110 is presented in FIG. 14 of the accompanying drawings, and the construction of plasmid pL110 is disclosed in Example 10d, the following section of the present Example.

About 25 µg of plasmid pL110 in 25 µl of TE buffer were added to 10 µl of 10×XbaI buffer (0.5 M NaCl; 60 mM Tris-HCl, pH=7.9; 60 mM MgCl$_2$; and 1 mg/ml BSA) and 55 µl of H$_2$O. About 10 µl (~50 units) of restriction enzyme XbaI were added to the solution of plasmid pL110 DNA, and the resulting reaction was incubated at 37° C. for 2 hours. The XbaI-digested plasmid pL110 DNA was precipitated with ethanol, collected by centrifugation, and resuspended in 10 µl of 10×BamHI buffer and 89 µl of H$_2$O. About 1 µl (~5 units) of restriction enzyme BamHI was added to the solution of XbaI-digested plasmid pL110 DNA, and the resulting reaction was incubated at 37° C. for 30 minutes to obtain a partial BamHI digest. The XbaI-partially-BamHI-digested plasmid-pL110 DNA was loaded onto an agarose gel and electrophoresed until the ~6.0 kb XbaI-BamHI fragment was clearly separated from the other digestion products. The ~6.0 kb restriction fragment was isolated from the gel; about 0.5 µg of the ~6.0 kb XbaI-BamHI restriction fragment was obtained and suspended in about 40 µl of glass-distilled H$_2$O. This ~6.0 kb XbaI-BamHI restriction fragment comprises all of plasmid pL110 except the EK-BGH-encoding DNA.

To construct plasmid pBW28, the following fragments are mixed together: about 0.1 µg (~8 µl) of the ~6.0 kb BamHI-XbaI restriction fragment of plasmid pL110; about 0.05 µg (~2 µl) of the ~560 bp NdeI-EcoRI restriction fragment of plasmid pM8BW27; about 0.1 µg (~2 µl) of the ~689 bp EcoRI-BamHI restriction fragment of plasmid pTPA103; and about 0.02 µg (~1 µl) of the ~45 bp XbaI-NdeI synthetic linker. About 2 µl of 10×ligase buffer and 1 µl (~1 Weiss unit) of T4 DNA ligase are added to the mixture of DNA, and the resulting ligation reaction is incubated at 4° C.

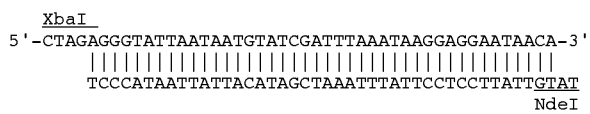

overnight for 2 hours. The ligated DNA constituted the desired plasmid pBW28. A restriction site and function map of plasmid pBW28 is presented in FIG. 14 of the accompanying drawings.

The ligated DNA was used to transform E. coli K12 MM294 (NRRL B-15625) made competent in substantial accordance with the procedure of Example 2, except that 50 mM CaCl$_2$ was used in the procedure. Due to the presence of the lambda pL promoter and the gene encoding the temperature-sensitive lambda pL repressor on plasmid pBW28, the transformation procedure and culturing of transformants were varied somewhat. The cells were not exposed to temperatures greater than 32° C. during transformation and subsequent culturing. The following section of this Example relates more fully the procedures for handling plasmids that encode the lambda pL promoter and its temperature-sensitive repressor. The desired *E. coli* K12 M294/pBW28 transformants were identified by their tetracycline-resistant, ampicillin-sensitive phenotype and by restriction enzyme analysis of their plasmid DNA.

D. Construction of Plasmid pL110

Plasmid pL110 was constructed using plasmid pKC283 as starting material. Lyophils of *E. coli* K12 BE1201/pKC283 are obtained from the NRRL under the accession number NRRL B-15830. The lyophils are decanted into tubes containing 10 ml of L broth and incubated two hours at 32° C., at which time the cultures are made 50 µg/ml in ampicillin and then incubated at 32° C. overnight. The *E. coli* K12 BE1201/pKC283 cells were cultured at 32° C., because plasmid pKC283 comprises the pL promoter and because *E. coli* K12 BE1201 cells comprise a temperature-sensitive cI repressor gene integrated into the cellular DNA. When cells that comprise a wild-type lambda pL repressor gene or when cells that do not comprise a lambda pL promoter are utilized in this plasmid isolation procedure, as described in subsequent Examples herein, the temperature of incubation is 37° C.

A small portion of the overnight culture is placed on L-agar plates containing 50 µg/ml ampicillin in a manner so as to obtain a single colony isolate of *E. coli* K12 BE1201/pKC283. The single colony obtained was inoculated into 10 ml of L broth containing 50 µg/ml ampicillin and incubated overnight at 32° C. with vigorous shaking. The 10 ml overnight culture was inoculated into 500 ml of L broth and incubated at 32° C. with vigorous shaking until the culture reached stationary phase. Plasmid pKC283 DNA was then prepared from the cells in substantial accordance with the procedure of Example 3. About 1 mg of plasmid pKC283 was obtained and stored at 4° C. in TE buffer at a concentration of about 1 µg/ul. A restriction site and function map of plasmid pKC283 is presented in FIG. 14 of the accompanying drawings.

About 10 µl (~10 µg) of the plasmid pKC283 DNA were mixed with 20 µl 10×medium-salt restriction buffer (500 mM NaCl; 100 mM Tris-HCl, pH=7.5; 100 mM $MgCl_2$; and 10 mM DTT), 20 µl 1 mg/ml BSA, 5 µl restriction enzyme PvuII (~25 units), and 145 µl of water, and the resulting reaction was incubated at 37° C. for 2 hours. Restriction enzyme reactions described herein were routinely terminated by phenol and then chloroform extractions, which were followed by precipitation of the DNA, an ethanol wash, and resuspension of the DNA in TE buffer. After terminating the PvuII digestion as described above, the PvuII-digested plasmid pKC283 DNA was precipitated and then resuspended in 5 µl of TE buffer.

About 600 picomoles (pM) of XhoI linkers (5'-CCTCGAGG-3') were kinased in a mixture containing 10 µl of 5×Kinase Buffer (300 mM Tris-HCl, pH=7.8; 50 mM $MgCl_2$; and 25 mM DTT), 5 µl of 5 mM ATP, 24 µl of $H_2O$, 0.5 µl of T4 polynucleotide kinase (about 2.5 units as defined by P-L Biochemicals), 5 µl of 1 mg/ml BSA, and 5 µl of 10 mM spermidine by incubating the mixture at 37° C. for 30 minutes. About 12.5 µl of the kinased XhoI linkers were added to the 5 µl of PvuII-digested plasmid pKC283 DNA, and then, 2.5 µl of 10×ligase buffer, 2.5 µl (about 2.5 units as defined by P-L Biochemicals) of T4 DNA ligase, 2.5 µl of 10 mM spermidine, and 12.5 µl of water were added to the DNA. The resulting ligation reaction was incubated at 4° C. overnight. After the ligation reaction, the reaction mixture was adjusted to have the composition of high-salt buffer (0.1 M NaCl; 0.05 M Tris-HCl, pH 7.5; 10.0 mM $MgCl_2$; and 1 mM DTT). About 10 µl (100 units) of restriction enzyme XhoI were added to the mixture, and the resulting reaction was incubated at 37° C. for 2 hours.

The reaction was terminated, and the XhoI-digested DNA was precipitated, resuspended, and ligated as described above, except that no XhoI linkers were added to the ligation mixture. The ligated DNA constituted the desired plasmid pKC283PX. A restriction site and function map of plasmid pKC283PX is presented in FIG. 14 of the accompanying drawings.

*E. coli* K12 MO($\lambda^+$), available from the NRRL under the accession number NRRL B-15993, comprises the wild-type lambda pL cI repressor gene, so that transcription from the lambda pL promoter does not occur in *E. coli* K12 MO($\lambda^+$) cells. Single colonies of *E. coli* K12 MO($\lambda^+$) are isolated, and a 10 ml overnight culture of the cells is prepared; no ampicillin is used in the growth media. Fifty µl of the overnight culture were used to inoculate 5 ml of L broth, which also contained 10 mM $MgSO_4$ and 10 mM $MgCl_2$. The culture was incubated at 37° C. overnight with vigorous shaking. The following morning, the culture was diluted to 200 ml with L broth containing 10 mM $MgSO_4$ and 10 mM $MgCl_2$. The diluted culture was incubated at 37° C. with vigorous shaking until the O.D.$_{590}$ was about 0.5, which indicated a cell density of about $1 \times 10^8$ cells/ml. The culture was cooled for ten minutes in an ice-water bath, and the cells were then collected by centrifugation at 4000×g for 10 minutes at 40° C. The cell pellet was resuspended in 100 ml of cold 10 mM NaCl and then immediately re-pelleted by centrifugation. The cell pellet was resuspended in 100 ml of 30 mM $CaCl_2$ and incubated on ice for 20 minutes.

The cells were again collected by centrifugation and resuspended in 10 ml of 30 mM $CaCl_2$. A one-half ml aliquot of the cells was added to the ligated DNA prepared above; the DNA had been made 30 mM in $CaCl_2$. The cell-DNA mixture was incubated on ice for one hour, heat-shocked at 42° C. for 90 seconds, and then chilled on ice for about two minutes. The cell-DNA mixture was diluted into 10 ml of LB media in 125 ml flasks and incubated at 37° C. for one hour. One hundred µl aliquots were plated on L-agar plates containing ampicillin and incubated at 37° C. until colonies appeared.

The colonies were individually cultured, and the plasmid DNA of the individual colonies was examined by restriction enzyme analysis and gel electrophoresis. Plasmid DNA isolation was performed on a smaller scale in accordance with the procedure of Example 3, but the CsCl gradient step was omitted until the desired *E. coli* K12 MO($\lambda^+$)/pKC283PX transformants were identified. A restriction site and function map of plasmid pKC283PX is presented in FIG. 14 of the accompanying drawings.

Ten µg of plasmid pKC283PX DNA were dissolved in 20 µl of 10×high-salt buffer, 20 µl 1 mg/ml BSA, 5 µl (~50 units) of restriction enzyme BglII, 5 µl (~50 units) of restriction enzyme XhoI, and 150 µl of water, and the resulting reaction was incubated at 37° C. for two hours. The reaction was stopped; the BglII-XhoI digested DNA was precipitated, and the DNA was resuspended in 5 µl of TE buffer.

A DNA linker with single-stranded DNA ends characteristic of BglII and XhoI restriction enzyme cleavage was synthesized using an automated DNA synthesizer and kinased as described in Example 6A. The DNA linker had the following structure:

The linker and BglII-XhoI-digested plasmid pKC283PX were ligated in substantial accordance with the ligation procedure described above. The ligated DNA constituted the desired plasmid pKC283-L. A restriction site and function map of plasmid pKC283-L is presented in FIG. 14 of the accompanying drawings. The plasmid pKC283-L DNA was used to transform *E. coli* K12 MO($\lambda^+$), and the resulting *E. coli* K12 MO($\lambda^+$)/pKC283-L transformants were identified by their ampicillin-resistant phenotype and by restriction enzyme analysis of their plasmid DNA.

About 10 μg of plasmid pKC283-L DNA were dissolved in 20 μl 10×high-salt buffer, 20 μl 1 mg/ml BSA, 5 μl (~50 units) restriction enzyme XhoI, and 155 μl of H$_2$O, and the resulting reaction was incubated at 37° C. for two hours. The XhoI-digested plasmid pKC283-L DNA was then precipitated and resuspended in 2 μl 10×nick-translation buffer (0.5 M Tris-HCl, pH=7.2; 0.1 M MgSO$_4$; and 1 mM DTT), 1 μl of a solution 2 mM in each of the deoxynucleotide triphosphates, 15 μl of H$_2$O, 1 μl (~6 units as defined by P-L Biochemicals) of Klenow, and 1 μl of 1 mg/ml BSA. The resulting reaction was incubated at 25° C. for 30 minutes; the reaction was stopped by incubating the solution at 70° C. for five minutes.

BamHI linkers (5'-CGGGATCCCG-3') were kinased and ligated to the XhoI-digested, Klenow-treated plasmid pKC283-L DNA in substantial accordance with the linker ligation procedures described above. After the ligation reaction, the DNA was digested with about 100 units of BamHI for about 2 hours at 37° C. in high-salt buffer. After the BamHI digestion, the DNA was prepared for ligation, and the ~5.9 kb BamHI restriction fragment was circularized by ligation and transformed into *E. coli* K12 MO($\lambda^+$) in substantial accordance with the procedures described above. The *E. coli* K12 MO($\lambda^+$)/pKC283-LB transformants were identified, and then, plasmid pKC283-LB DNA was prepared from the transformants in substantial accordance with the procedure of Example 3. A restriction site and function map of plasmid pKC283-LB is presented in FIG. 14 of the accompanying drawings.

About 10 μg of plasmid pKC283PX were digested with restriction enzyme SalI in high-salt buffer, treated with Klenow, and ligated to EcoRI linkers (5'-GAGGAATTCCTC-3') in substantial accordance with the procedures described above. After digestion with restriction enzyme EcoRI, which results in the excision of ~2.1 kb of DNA, the ~4.0 kb EcoRI restriction fragment was circularized by ligation to yield plasmid pKC283PRS. The ligated DNA was used to transform *E. coli* K12 MO($\lambda^+$), and after the *E. coli* K12 MO($\lambda^+$)/pKC283PRS transformants were identified, plasmid pKC283PRS DNA was prepared from the transformants in substantial accordance with the procedure of Example 3. A restriction site and function map of plasmid pKC283PRS is presented in FIG. 14 of the accompanying drawings.

About 10 μg of plasmid pKC283PRS were digested in 200 μl of high-salt buffer with about 50 units each of restriction enzymes PstI and SphI. After incubating the reaction at 37° C. for about 2 hours, the reaction mixture was electrophoresed on a 0.6% low-gelling-temperature agarose (FMC Corporation, Marine Colloids Division, Rockland, Me. 04841) gel for 2–3 hours at ~130 V and ~75 mA in Tris-Acetate buffer.

The gel was stained in a dilute solution of ethidium bromide, and the band of DNA constituting the ~0.85 kb PstI-SphI restriction fragment, which was visualized with long-wave UV light, was cut from the gel in a small segment. The volume of the segment was determined by weight and density of the segment, and an equal volume of 10 mM Tris-HCl, pH 7.6, was added to the tube containing the segment. The segment was then melted by incubation at 72° C. About 1 ug of the 0.85 kb PstI-SphI restriction fragment of plasmid pKC283PRS was obtained in a volume of about 100 μl. In an analogous manner, plasmid pKC283-LB was digested with restriction enzymes PstI and SphI, and the resulting ~3.0 kb restriction fragment was isolated by agarose gel electrophoresis and prepared for ligation.

The ~0.85 kb PstI-SphI restriction fragment of plasmid pKC283PRS was ligated to the ~3.0 kb PstI-SphI restriction fragment of plasmid pKC283-LB. The ligated DNA constituted the desired plasmid pL32. A restriction site and function map of plasmid pL32 is presented in FIG. 14 of the accompanying drawings. Plasmid pL32 was transformed into *E. coli* K12 MO($\lambda^+$) cells; plasmid pL32 DNA was prepared from the *E. coli* K12 MO($\lambda^+$)/pL32 transformants in substantial accordance with the procedure of Example 3. Analysis of the plasmid pL32 DNA demonstrated that more than one EcoRI linker attached to the Klenow-treated, SalI ends of plasmid pKC283PX. The presence of more than one EcoRI linker does not affect the utility of plasmid pL32 or derivatives of plasmid pL32 and can be detected by the presence of an XhoI restriction site, which is generated whenever two of the EcoRI linkers are ligated together.

Plasmid pCC101 is disclosed in Example 3 of U.S. patent application Ser. No. 586,581, filed Mar. 6, 1984, attorney docket number X-5872A, incorporated herein by reference. A restriction site and function map of plasmid pCC101 is presented in FIG. 14 of the accompanying drawings. To isolate the EK-BGH-encoding DNA, about 10 μg of plasmid pCC101 were digested in 200 μl of high-salt buffer containing about 50 units each of restriction enzymes XbaI and BamHI. The digestion products were separated by agarose gel electrophoresis, and the ~0.6 kb XbaI-BamHI restriction fragment which encodes EK-BGH was isolated from the gel and prepared for ligation.

Plasmid pL32 was also digested with restriction enzymes XbaI and BamHI, and the ~3.9 kb restriction fragment was isolated and prepared for ligation. The ~3.9 kb XbaI-BamHI restriction fragment of plasmid pL32 was ligated to the ~0.6 kb XbaI-BamHI restriction fragment of plasmid pCC101 to yield plasmid pL47. A restriction site and function map of plasmid pL47 is presented in FIG. 14 of the accompanying drawings. Plasmid pL47 was transformed into *E. coli* K12 MO($\lambda^+$), and the *E. coli* K12 MO($\lambda^+$)/pL47 transformants were identified. Plasmid pL47 DNA was prepared from the transformants in substantial accordance with the procedures of Example 3.

Plasmid pPR12 comprises the temperature-sensitive pL repressor gene cI857 and the plasmid pBR322 tetracycline resistance-conferring gene. Plasmid pPR12 is disclosed and claimed in U.S. Pat. No. 4,436,815, issued Mar. 13, 1984. A restriction site and function map of plasmid pPR12 is presented in FIG. 14 of the accompanying drawings.

About 10 μg of plasmid pPR12 were digested with about 50 units of restriction enzyme EcoRI in 200 μl of high-salt buffer at 37° C. for two hours. The EcoRI-digested plasmid pPR12 DNA was precipitated and then treated with Klenow in substantial accordance with the procedure described above. After the Klenow reaction, the EcoRI-digested, Klenow-treated plasmid pPR12 DNA was recircularized by ligation, and the ligated DNA, which constituted the desired plasmid pPR12ΔR1, was used to transform E. coli K12 RV308 (NRRL B-15624); transformants were selected based on tetracycline (10 ug/ml) resistance. After the E. coli K12 RV308/pPR12ΔR1 transformants were identified, plasmid pPR12ΔR1 DNA was prepared from the transformants in substantial accordance with the procedure of Example 3.

About 10 μg of plasmid pPR12ΔR1 were digested with about 50 units of restriction enzyme AvaI in 200 μl of medium-salt buffer at 37° C. for 2 hours. The AvaI-digested plasmid pPR12ΔR1 DNA was precipitated and then treated with Klenow. After the Klenow reaction, the AvaI-digested, Klenow-treated plasmid pPR12ΔR1 DNA was ligated to EcoRl linkers (5'-GAGGAATTCCTC-3'), precipitated, resuspended in about 200 μl of high-salt buffer containing about 50 units of restriction enzyme EcoR1, and incubated at 37° C. for about 2 hours. After the EcoR1 digestion, the reaction mixture was loaded onto a low-melting agarose gel, and the ~5.1 kb EcoR1 restriction fragment was purified from the gel and recircularized by ligation to yield the desired plasmid pPR12AR1. The plasmid pPR12AR1 DNA was transformed into E. coli K12 RV308; selection of transformants was based on tetracycline resistance. Plasmid pPR12AR1 DNA was prepared from the transformants in substantial accordance with the procedure of Example 3. A restriction site and function map of plasmid pPR12AR1 is presented in FIG. 14 of the accompanying drawings.

About 10 μg of plasmid pPR12AR1 DNA were suspended in about 200 ml of high-salt buffer containing about 50 units each of restriction enzymes PstI and EcoRI, and the digestion reaction was incubated at 37° C. for about 2 hours. The reaction mixture was then loaded onto an agarose gel, and the ~2.9 kb PstI-EcoR1 restriction fragment of plasmid pPR12AR1 was isolated and prepared for ligation.

About 10 ug of plasmid pL47 were digested with restriction enzymes PstI and BamHI in 200 ul of high-salt buffer at 37° C. for two hours. The PstI-BamHI-digested DNA was loaded onto an agarose gel, and the ~2.7 kb PstI-BamHI restriction fragment that comprised the origin of replication and a portion of the ampicillin resistance-conferring gene was isolated and prepared for ligation. In a separate reaction, about 10 ug of plasmid pL47 DNA were digested with restriction enzymes EcoRI and BamHI in 200 ul of high-salt buffer at 37° C. for two hours, and the ~1.03 kb EcoRI-BamHI restriction fragment that comprised the lambda pL transcription activating sequence, the E. coli lpp translation activating sequence, and the EK-BGH-encoding DNA was isolated and prepared for ligation.

The ~2.7 kb PstI-BamHI and ~1.03 kb EcoRI-BamHI restriction fragments of plasmid pL47 were ligated to the ~2.9 kb PstI-EcoR1 restriction fragment of plasmid pPR12AR1 to construct plasmid pL110, and the ligated DNA was used to transform E. coli K12 RV308. Tetracycline resistance was used as the basis for selecting transformants.

Two PstI restriction enzyme recognition sites are present in the EK-BGH coding region that are not depicted in the restriction site and function maps presented in the accompanying drawings. A restriction site and function map of plasmid pL110 is presented in FIG. 14 of the accompanying drawings.

E. Final Construction of Plasmid pBW32

Approximately 10 μg of plasmid pSV2-β-globin DNA (NRRL B-15928) were dissolved in 10 μl 10×HindIII reaction buffer, 5 μl (~50 units) restriction enzyme HindIII, and 85 μl H$_2$O, and the reaction was placed at 37° C. for 2 hours. The reaction mixture was then made 0.15 M in LiCl, and after the addition of 2.5 volumes of ethanol and incubation in a dry ice-ethanol bath, the DNA was pelleted by centrifugation.

The DNA pellet was dissolved in 10 μl 10×BglII buffer, 5 μl (~50 units) restriction enzyme BglII, and 85 μl H$_2$O, and the reaction was placed at 37° C. for two hours. After the BglII digestion, the reaction mixture was loaded onto a 0.85% agarose gel, and the fragments were separated by electrophoresis. The gel was visualized using ethidium bromide and ultraviolet light, and the band containing the desired ~4.2 kb HindIII-BglII fragment was excised from the gel as previously described. The pellet was resuspended in 10 μl of H$_2$O and constituted ~5 μg of the desired ~4.2 kb HindIII-BglII restriction fragment of plasmid pSV2-β-globin. The ~2.0 kb HindIII-BamH1 restriction fragment of plasmid pTPA103 that encodes TPA was isolated from plasmid pTPA103 in substantial accordance with the foregoing teaching. About 5 μg of the ~2.0 kb HindIII-BamHI restriction fragment of plasmid pTPA103 were obtained, suspended in 10 μl of H$_2$O, and stored at −20° C.

Two μl of the ~4.2 kb BglII-HindIII restriction fragment of plasmid pSV2-β-globin and 4 μl of the ~2.0 kb HindIII-BamH1 fragment of plasmid pTPA103 were mixed together and then incubated with 2 μl of 10×ligase buffer, 11 μl of H$_2$O, and 1 μl of T4 DNA ligase (~500 units) at 4° C. overnight. The ligated DNA constituted the desired plasmid pTPA301; a restriction site and function map of the plasmid is presented in FIG. 14 of the accompanying drawings. The ligated DNA was used to transform E. coli K12 RR1 cells (NRRL B-15210) made competent for transformation in substantial accordance with the teaching of Example 3. Plasmid DNA was obtained from the E. coli K12 RR1/pTPA301 transformants in substantial accordance with the procedure of Example 3.

Plasmid pSV2-dhfr comprises a dihydrofalate reductase (dhfr) gene useful for selection of transformed eukaryotic cells and amplification of DNA covalently linked to the dhfr gene. Ten μg of plasmid pSV2-dhfr (isolated from E. coli K12 HB101/pSV2-dhfr, ATCC 37146) were mixed with 10 μl 10×PvuII buffer, 2 μl (~20 units) PvuII restriction enzyme, and 88 μl of H$_2$O, and the resulting reaction was incubated at 37° C. for two hours. The reaction was terminated by phenol and chloroform extractions, and then, the PvuII-digested plasmid pSV2-dhfr DNA was precipitated and collected by centrifugation.

BamHI linkers (5'-CGGATCCCG-3') were kinased and prepared for ligation by the following procedure. To 1 μg of linker in 5 μl H$_2$O was added: 10 μl 5×Kinase salts (300 mM Tris-HCl, pH=7.8; 50 mM MgCl$_2$; and 25 mM DTT), 5 μl of 5 mM ATP, 5 μl of BSA (1 mg/ml), 5 μl of 10 mM spermidine, 19 μl of H$_2$O, and 1 μl of polynucleotide Kinase (10 units/μl). This reaction was then incubated at 37° for 60 minutes and stored at −20° C. Five μl (~5 μg) of the PvuII-digested plasmid pSV2-dhfr and 12 μl (~25 μg) of the kinased BamHI linkers were mixed and incubated with 11 μl of H$_2$O, 2 μl 10×ligase buffer, and 1 μl (~1000 units) of T4 DNA ligase at 16° C. overnight.

Ten μl of 10×BamHI reaction buffer, 10 μl (~50 units) of BamHI restriction enzyme, and 48 μl of H$_2$O were added to the ligation reaction mixture, which was then incubated at 37° C. for 3 hours. The reaction was loaded onto a 1% agarose gel, and the desired ~1.9 kb fragment, which comprises the dhfr gene, was isolated from the gel. All linker additions performed in these examples were routinely purified on an agarose gel to reduce the likelihood of multiple linker sequences in the final vector. The ~3 μg of fragment obtained were suspended in 10 μl of TE buffer.

Next, approximately 15 μl (~1 μg) of plasmid pTPA301 were digested with BamHI restricton enzyme as taught above. Because there is a unique BamHI site in plasmid pTPA301, this BamHI digestion generates linear plasmid pTPA301 DNA. The BamHI-digested plasmid pTPA301 was precipitated with ethanol and resuspended in 94 μl of $H_2O$ and phosphatased using 1 μl of Calf-Intestinal Alkaline phosphatase (Collaborative Research, Inc., 128 Spring Street, Lexington, Mass. 02173), and 5 μl of 1 M Tris-HCl, pH=9.0, at 65° C. for 45 min. The DNA was extracted with phenol:chloroform, then extracted with chloroform:isoamyl alcohol, ethanol precipitated, and resuspended in 20 μl $H_2O$. Ten μl (~0.25 μg) of phosphatased plasmid pTPA301 were added to 5 μl of the BamHI, dhfr-gene-containing restriction fragment (~1.5 μg), 3 μl of 10×ligase buffer, 3 μl (~1500 units) of T4 DNA ligase, and 9 μl $H_2O$. This ligation reaction was incubated at 15° C. overnight; the ligated DNA constituted the desired plasmid pTPA303 DNA.

Plasmid pTPA303 was used to transform *E. coli* K12 RR1 (NRRL B-15210), and the resulting *E. coli* K12 RR1/pTPA303 transformants were identified by their ampicillin-resistant phenotype and by restriction enzyme analysis of their plasmid DNA. Plasmid pTPA303 was isolated from the transformants in substantial accordance with the procedure of Example 3.

To isolate the ~2.7 kb EcoRI-BglII restriction fragment that encodes the pBR322 replicon and β-lactamase gene from plasmid pTPA301, about 10 μg of plasmid pTPA301 are digested to completion in 400 μl total reaction volume with 20 units BglII restriction enzyme in 1×BglII buffer at 37° C. After the BglII digestion, the Tris-HCl concentration is adjusted to 110 mM, and 20 units of EcoRI restriction enzyme are added to the BglII-digested DNA. The EcoRI-BglII-digested DNA is loaded onto an agarose gel and electrophoresed until the ~2.7 kb EcoRI-BglII restriction fragment is separated from the other digestion products, and then, the ~2.7 kb fragment is isolated and prepared for ligation.

To isolate a restriction fragment that comprises the dhfr gene, plasmid pTPA303 was double-digested with HindIII and EcoRI restriction enzymes, and the ~2340 bp EcoRI-HindIII restriction fragment that comprises the dhfr gene was isolated and recovered.

To isolate the ~2 kb HindIII-SstI restriction fragment of plasmid pTPA303 that comprises the coding region for the carboxy-terminus of TPA and the SV40 promoter, plasmid pTPA303 was double digested with HindIII and SstI restriction enzymes in 1×HindIII buffer. The ~1.7 kb fragment was isolated from the gel and prepared for ligation.

To isolate the ~680 bp XhoII (compatible for ligation with the BglII overlap)-SstI restriction fragment of plasmid pBW28 that comprises the coding region for the amino terminus of modified TPA, about 10 μg of plasmid pBW28 were digested with XhoII enzyme to completion in 1×XhoII buffer (0.1 M Tris-HCl, pH=8.0; 0.1 M $MgCl_2$; 0.1% Triton X-100; and 1 mg/ml BSA). The XhoII-digested DNA was recovered by ethanol precipitation and subsequently digested to completion with SstI enzyme. The XhoII-SstI-digested DNA was loaded onto an acrylamide gel, and the desired fragment was isolated and prepared for ligation.

About 0.1 μg of each of the above fragments: the ~2.7 kb EcoRI-BglII restriction fragment of plasmid pTPA301; the ~2.34 kb EcoRI-HindIII restriction fragment of plasmid pTPA303; the ~1.7 kb SstI-HindIII restriction fragment of plasmid pTPA303; and the ~0.68 kb SstI-XhoII restriction fragment of plasmid pBW28 were ligated together to form plasmid pBW32. The ligation mix was used to transform *E. coli* K12 MM294 as taught in Example 2, except that 50 mM $CaCl_2$ was used in the procedure. Transformants were identified by their ampicillin-resistant phenotype and by restriction analysis of their plasmid DNA. Plasmid pBW32 DNA was obtained from the *E. coli* K12 MM294/pBW32 transformants in substantial accordance with the procedure of Example 3. A restriction site and function map of plasmid pBW32 is presented in FIG. 14 of the accompanying drawings.

EXAMPLE 11

Construction of Plasmids pLPChd1, pLPChd2, pLPCdhfr1, and pLPCdhfr2

A. Construction of Plasmids pLPChd1 and pLPChd2

About 20 μg of plasmid pBW32 in 20 μl of TE buffer were added to 10 μl of 10×BamHI buffer and 60 μl of $H_2O$. About 10 μl (~50 units) of restriction enzyme BamHI were added to the solution of plasmid pBW32 DNA, and the resulting reaction was incubated at 37° C. for two hours. The BamHI-digested plasmid pBW32 DNA was precipitated with ethanol, collected by centrifugation, and resuspended in 5 μl of 10×Klenow buffer, 45 μl of $H_2O$, and 2 μl (~100 units) of Klenow enzyme. The reaction was incubated at 16° C. for 30 minutes; then, the reaction mixture was loaded onto an agarose gel and electrophoresed until the digestion products were clearly separated. The ~1.9 kb Klenow-treated, BamHI restriction fragment of plasmid pBW32 that comprises the dhfr gene was isolated from the gel and prepared for ligation in substantial accordance with the procedure of Example 4A. About 4 μg of the desired fragment were obtained and suspended in 5 μl of TE buffer.

About 200 μg of plasmid pLPChyg1 in 100 μl of TE buffer were added to 15 μl of 10×EcoRI buffer and 30 μl of $H_2O$. About 5 μl (~50 units) of restriction enzyme EcoRI were added to the solution of plasmid pLPChyg1 DNA, and the resulting reaction was incubated at 37° C. for about 10 minutes. The short reaction time was calculated to produce a partial EcoRI digestion. Plasmid pLPChyg1 has two EcoRI restriction sites, one of which is within the coding sequence of the hygromycin resistance-conferring (HmR) gene, and it was desired to insert the dhfr-gene-containing restriction fragment into the EcoRI site of plasmid pLPChyg1 that is not in the HmR gene. The partially-EcoRI-digested plasmid pLPChyg1 DNA was loaded onto an agarose gel and electrophoresed until the singly-cut plasmid pLPChyg1 DNA was separated from uncut plasmid DNA and the other digestion products. The singly-cut DNA was isolated from the gel and prepared for ligation in substantial accordance with the procedure of Example 4A. About 2 μg of the singly-EcoRI-cut plasmid pLPChyg1 were obtained and suspended in 25 μl of TE buffer. To this sample, about 5 μl (~25 units) of Klenow enzyme, 5 μl of 10×Klenow buffer, and 40 μl of $H_2O$ were added, and the resulting reaction was incubated at 16° C. for 60 minutes. The Klenow-treated, partially-EcoRI-digested DNA was then extracted twice with phenol and then once with chloroform, precipitated with ethanol, and resuspended in 25 μl of TE buffer.

About 5 μl of the ~1.9 kb Klenow-treated BamHI restriction fragment of plasmid pBW32 and about 5 μl of the singly-EcoRI-cut plasmid pLPChyg1 DNA were mixed together, and 1 μl of 10×ligase buffer, 5 μl of $H_2O$, 1 μl (~500 units) of T4 DNA ligase, and 1 μl (~2 units) of T4 RNA ligase were added to the mixture of DNA, and the resulting reaction was incubated at 16° C. overnight. The ligated DNA constituted the desired plasmids pLPChd1 and pLPChd2, which differ only with respect to the orientation of the ~1.9 kb fragment that comprises the dhfr gene.

The ligated DNA was used to transform *E. coli* K12 HB101 cells made competent for transformation in substantial accordance with the procedure of Example 2. The transformed cells were plated onto L agar containing 100 μg/ml ampicillin, and the ampicillin-resistant transformants were analyzed by restriction enzyme analysis of their plasmid DNA to identify the *E. coli* K12 HB101/pLPChd1 and *E. coli* K12 HB101/pLPChd2 transformants. A restriction site and function map of plasmid pLPChd1 is presented in FIG. 15 of the accompanying drawings. Plasmid pLPChd1 and plasmid pLPChd2 DNA were isolated from the appropriate transformants in substantial accordance with the procedure of Example 3.

Plasmids pLPChd3 and pLPChd4 are similar in structure to plasmids pLPChd1 and pLPChd2. Plasmids pLPChd3 and pLPChd4 are constructed in substantial accordance with the procedure used to construct plasmids pLPChd1 and pLPChd2, except plasmid pLPChyg2 is used as starting material in the procedure rather than plasmid pLPChyg1.

B. Construction of Plasmids pLPCdhfr1 and pLPCdhfr2

About 100 μg of plasmid pBW32 in 100 μl of TE buffer were added to 15 μl of 10×BamHI buffer and 25 μl of H$_2$O. About 10 μl (~25 units) of restriction enzyme BamHI were added to the solution of plasmid pBW32 DNA, and the resulting reaction was incubated at 37° C. for 2 hours. The BamHI-digested plasmid pBW32 DNA was treated with Klenow in substantial accordance with the procedure in Example 11A. The blunt-ended fragment was precipitated with ethanol, resuspended in 10 μl of TE buffer, loaded onto an agarose gel, and electrophoresed until the ~1.9 kb BamHI restriction fragment that comprises the dihydrofolate reductase gene was separated from the other digestion products. The ~1.9 kb restriction fragment was then isolated from the gel and prepared for ligation in substantial accordance with the procedure of Example 4A; about 10 μg of the desired fragment were obtained and suspended in 50 μl of TE buffer.

About 5 μl of NdeI-StuI-digested plasmid pLPC DNA, as prepared in Example 9, were added to 5 μl of the Klenow-treated, ~1.9 kb BamHI restriction fragment of plasmid pBW32, 1.5 μl of 10×ligase buffer, 1 μl (~1000 units) of T4 DNA ligase, 1 μl (~2 units) of T4 RNA ligase, and 1.5 μl of H$_2$O. The resulting ligation reaction was incubated at 16° C. overnight; the ligated DNA constituted the desired plasmids pLPCdhfr1 and pLPCdhfr2, which differ only with respect to the orientation of the ~1.9 kb fragment that contains the dhfr gene. The ligated DNA was used to transform *E. coli* K12 HB101 in substantial accordance with the procedure of Example 2. The transformed cells were plated onto L agar containing ampicillin, and the ampicillin-resistant *E. coli* K12 HB101/pLPCdhfr1 and *E. coli* K12 HB101/pLPCdhfr2 transformants were identified by restriction enzyme analysis of their plasmid DNA.

EXAMPLE 12

Construction of Plasmid phd

To construct plasmid phd, it was necessary to prepare the plasmid pLPChd1 DNA, used as starting material in the construction of plasmid phd, from *E. coli* host cells that lack an adenine methylase, such as that encoded by the dam gene, the product of which methylates the adenine residue in the sequence 5'-GATC-3'. *E. coli* K12 GM48 (NRRL B-15725) lacks a functional dam methylase and so is a suitable host to use for the purpose of preparing plasmid pLPChd1 DNA for use as starting material in the construction of plasmid phd.

*E. coli* K12 GM48 cells were cultured and made competent for transformation, and plasmid pLPChyg1 was used to transform the *E. coli* K12 GM48 cells in substantial accordance with the procedure of Example 2. The transformed cells were plated on L agar containing ampicillin, and once the ampicillin-resistant, *E. coli* K12 GM48/pLPChd1 transformants had formed colonies, one such colony was used to prepare plasmid pLPChd1 DNA in substantial accordance with the procedure of Example 3. About 1 mg of plasmid pLPChd1 DNA was obtained and suspended in about 1 ml of TE buffer.

About 2 μg of plasmid pLPChd1 DNA in 2 μl of TE buffer were added to 2 μl of 10×BclI buffer (750 mM KCl; 60 mM Tris-HCl, pH=7.4; 100 mM MgCl$_2$; 10 mM DTT and 1 mg/ml BSA) and 14 μl of H$_2$O. About 2 μl (~10 units) of restriction enzyme BclI were added to the solution of plasmid pLPChd1 DNA, and the resulting reaction was incubated at 50° C. for two hours. The reaction was stopped by extracting the mixture once with phenol and twice with chloroform.

About 1 μl of the BclI-digested plasmid pLPChd1 DNA was added to 1 μl of 10×ligase buffer, 8 μl of H$_2$O and 1 μl (~500 units) of T4 DNA ligase. The ligation reaction was incubated at 16° C. overnight, and the ligated DNA constituted the desired plasmid phd. Plasmid phd results from the deletion of the extra BclI linkers that attached during the construction of plasmid pLPcat and the two adjacent BclI restriction fragments of a total size of about 1.45 kb from plasmid pLPChd1. A restriction site and function map of plasmid phd is presented in FIG. 16 of the accompanying drawings. Plasmid phd facilitates the expression of any DNA sequence from the BK virus enhancer-adenovirus late promoter of the present invention, because the DNA to be expressed can be readily inserted in the correct position for expression at the single BclI site on plasmid phd.

The ligated DNA was used to transform *E. coli* K12 GM48 in substantial accordance with the procedure of Example 2. The transformed cells were plated on L agar containing ampicillin, and the ampicillin-resistant *E. coli* K12 GM48/phd transformants were identified by restriction enzyme analysis of their plasmid DNA.

Plasmids analogous to plasmid phd can be constructed in substantial accordance with the foregoing procedure for constructing plasmid phd using any of plasmids pLPChd2, pLPChd3, or pLPChd4 as starting material rather than plasmid pLPChd1. These analagous plasmids differ from plasmid phd only with respect to the orientation of the hygromycin resistance-conferring and/or dhfr genes.

EXAMPLE 13

Construction of Plasmid pLPCE1A

To isolate the E1A gene of adenovirus 2 DNA, about 20 μg of adenovirus 2 DNA (from BRL) were dissolved in 10 μl of 10×BalI buffer (100 mM Tris-HCl, pH=7.6; 120 mM MgCl$_2$; 100 mM 2-mercaptoethanol; and 1 mg/ml BSA) and 80 μl of H$_2$O. About 10 μl (about 20 units) of restriction enzyme BalI were added to the solution of adenovirus 2 DNA, and the resulting reaction was incubated at 37° C. for two hours. The BalI-digested DNA was loaded onto an agarose gel and electrophoresed until the ~1.8 kb restriction fragment that comprises the E1A gene was separated from the other digestion products. The ~1.8 kb fragment was isolated from the gel and prepared for ligation in substantial accordance with the procedure of Example 4A. About 3 μg of the desired fragment was obtained and suspended in 20 μl of TE buffer.

About 5 μg of plasmid pLPC in 5 μl of TE buffer were added to 2 μl of 10×StuI buffer and 11 μl of H₂O. About 2 μl (~10 units) of restriction enzyme StuI were added to the solution of plasmid pLPC, and the resulting reaction was incubated at 37° C. for 2 hours. The StuI-digested plasmid pLPC DNA was precipitated with ethanol and resuspended in 2 μl of 10×NdeI buffer and 16 μl of H₂O. About 2 μl (~10 units) of restriction enzyme NdeI were added to the solution of StuI-digested plasmid PLPC DNA, and the resulting reaction was incubated at 37° C. for 2 hours.

The NdeI-StuI-digested plasmid pLPC DNA was precipitated with ethanol and resuspended in 5 μl of 10×Klenow buffer and 42 μl of H₂O. About 3 μl (~6 units) of Klenow enzyme were added to the solution of DNA, and the resulting reaction was incubated at 37° C. for 30 minutes. The reaction mixture was then loaded onto an agarose gel and electrophoresed until the ~5.82 kb, Klenow-treated, NdeI-StuI restriction fragment was clearly separated from the other reaction products. The fragment was isolated from the gel and prepared for ligation in substantial accordance with the procedure of Example 4A. About 2 μg of the ~5.82 kb, Klenow-treated, NdeI-StuI restriction fragment of plasmid pLPC were obtained and suspended in 25 μl of TE buffer.

About 9 μl of the ~1.8 kb BalI restriction fragment of adenovirus 2 that encodes the E1A gene and 3 μl of the ~5.82 kb, Klenow-treated, NdeI-StuI restriction fragment of plasmid pLPC were added to 2 μl of 10×ligase buffer and 4 μl of H₂O. About 1 μl (~500 units) of T4 DNA ligase and 1 μl (~2 units) of T4 RNA ligase were added to the solution of DNA, and the resulting reaction was incubated at 16° C. overnight.

The ligated DNA constituted the desired plasmids pLPCE1A and pLPCE1A1, which differ with respect to the orientation of the E1A gene and possibly differ with respect to the expression-enhancing effect the BK enhancer has on the E1A gene on the plasmid. Because the E1A promoter is located closer to the BK enhancer on plasmid pLPCE1A than plasmid pLPCE1A1, E1A expression may be higher when plasmid pLPCE1A is used as opposed to plasmid pLPCE1A1. A restriction site and function map of plasmid pLPCE1A is presented in FIG. 17 of the accompanying drawings.

The ligated DNA was used to transform E. coli K12 HB101 in substantial accordance with the procedure of Example 2. The transformed cells were plated on L agar containing ampicillin, and the ampicillin-resistant transformants were screened by restriction enzyme analysis of their plasmid DNA to identify the E. coli K12 HB101/pLPCE1A and E. coli K12 HB101/pLPCE1A1 transformants. Plasmid DNA was obtained from the transformants for use in later experiments in substantial accordance with the procedure of Example 3.

EXAMPLE 14

Construction of Plasmid pBLT

About 1 μg of plasmid pBW32 DNA (FIG. 14, Example 10) in 1 μl of TE buffer was added to 2 μl of 10×BamHI buffer and 15 μl of H₂O. About 2 μl (~10 units) of restriction enzyme BamHI were added to the solution of plasmid pBW32 DNA, and the resulting reaction was incubated at 37° C. for 2 hours. The reaction was stopped by first extracting the reaction mixture with phenol and then extracting the reaction mixture twice with chloroform. About 1 μl of the BamHI-digested plasmid pBW32 DNA was added to 1 μl of 10×ligase buffer and 8 μl of H₂O, and after about 1 μl (~500 units) of T4 DNA ligase was added to the solution of DNA, the resulting reaction was incubated at 16° C. overnight.

The ligated DNA constituted the desired plasmid pBW32del, which is about 5.6 kb in size and comprises a single HindIII restriction site. The ligated DNA was used to transform E. coli K12 HB101 in substantial accordance with the procedure of Example 2. The desired E. coli K12 HB101/pBW32del transformants were identified by their ampicillin-resistant phenotype and by restriction enzyme analysis of their plasmid DNA. Plasmid pBW32del DNA was obtained from the transformants for use in subsequent constructions in substantial accordance with the procedure of Example 3.

About 1 μg of plasmid pBW32del in 1 μl of TE buffer was added to 2 μl of 10×HindIII buffer and 15 μl of H₂O. About 2 μl (~10 units) of restriction enzyme HindIII were added to the solution of plasmid pBW32del DNA, and the resulting reaction was incubated at 37° C. for 2 hours. The sample was diluted to 100 μl with TE buffer and treated with calf-intestinal alkaline phosphatase in substantial accordance with the procedure described in Example 2. The reaction was extracted twice with phenol then once with chloroform. The HindIII-digested plasmid pBW32del DNA was then precipitated with ethanol and resuspended in 10 μl of H₂O.

Plasmid pBal8cat (Example 17) was digested with restriction enzyme HindIII, and the ~0.65 kb HindIII restriction fragment that comprises the modified BK enhancer-adenovirus 2 late promoter cassette was isolated and prepared for ligation in substantial accordance with the procedure of Example 5. About 0.1 μg of the ~0.65 kb HindIII restriction fragment of plasmid pBal8cat in 5 μl of TE buffer was added to 3 μl of the solution of HindIII-digested plasmid pBW32del. About 1 μl (~500 units) of T4 DNA ligase and 1 μl of 10×ligase buffer were added to the mixture of DNA, and the resulting reaction was incubated at 16° C. overnight.

The ligated DNA constituted the desired plasmid pBLT. A restriction site and function map of plasmid pBLT is presented in FIG. 18 of the accompanying drawings. The ligated DNA was used to transform E. coli K12 HB101 in substantial accordance with the procedure of Example 2. The transformed cells were plated on L agar containing ampicillin, and the ampicillin-resistant E. coli K12 HB101/pBLT transformants were identified by restriction enzyme analysis of their plasmid DNA. Because the ~0.65 kb HindIII restriction fragment could insert into HindIII-digested plasmid pBW32del in either one of two orientations, only one of which yields plasmid pBLT, the orientation of the ~0.65 kb HindIII restriction fragment had to be determined to identify the E. coli K12 HB101/pBLT transformants. Plasmid pBLT DNA was prepared from the transformants for use in subsequent constructions in substantial accordance with the procedure of Example 3.

EXAMPLE 15

Construction of Plasmids pBLThyg1, pBLThyg2, pBLTdhfr1, and pBLTdhfr2

A. Construction of Plasmids pBLThyg1 and pBLThyg2

About 4 μg of plasmid pBLT DNA in 4 μl of TE buffer were added to 2 μl of 10×BamHI buffer and 12 μl of H₂O. About 2 μl (~10 units) of restriction enzyme BamHI were added to the solution of plasmid pBLT DNA, and the resulting reaction was incubated at 37° C. for 2 hours. The reaction was stopped by extracting the reaction mixture first with phenol and then with chloroform. The BamHI-digested plasmid pBLT DNA was then precipitated with ethanol and resuspended in 2 µl of TE buffer.

About 10 µg of plasmid pSV2hyg in 10 µl of TE buffer were added to 10 µl of 10×BamHI buffer and 75 µl of H₂O. About 5 µl (~25 units) of restriction enzyme BamHI were added to the solution of plasmid pSV2hyg DNA, and the resulting reaction was incubated at 37° C. for 2 hours. The BamHI-digested plasmid pSV2hyg DNA was precipitated with ethanol, resuspended in 10 µl of TE buffer, loaded onto an agarose gel, and electrophoresed until the ~2.5 kb BamHI restriction fragment that comprises the hygromycin resistance-conferring gene was separated from the other digestion products. The ~2.5 kb restriction fragment was then isolated from the gel and prepared for ligation in substantial accordance with the procedure of Example 4A; about 2 µg of the desired fragment were obtained and suspended in 10 µl of TE buffer.

About 2 µl of the BamHI-digested plasmid pBLT DNA and 1 µl of the ~2.5 kb BamHI restriction fragment of plasmid pSV2hyg were added to 1 µl of 10×ligase buffer, 5 µl of H₂O, and 1 µl (~500 units) of T4 DNA ligase, and the resulting reaction was incubated at 16° C. overnight. The ligated DNA constituted the desired plasmids pBLThyg1 and pBLThyg2. A restriction site and function map of plasmid pBLThyg1 is presented in FIG. 19 of the accompanying drawings. Plasmids pBLThyg1 and pBLThyg2 differ only with respect to the orientation of the ~2.5 kb BamHI restriction fragment that encodes the hygromycin resistance-conferring gene.

The ligated DNA was used to transform *E. coli* K12 HB101 in substantial accordance with the procedure of Example 2. The transformed cells were plated onto L agar containing ampicillin, and the ampicillin-resistant *E. coli* K12 HB101/pBLThyg1 and *E. coli* K12 HB101/pBLThyg2 transformants were identified by restriction enzyme analysis of their plasmid DNA.

B. Construction of Plasmids pBLTdhfr1 and pBLTdhfr2

About 100 µg of plasmid pBW32 in 100 µl of TE buffer were added to 15 µl of 10×BamHI buffer and 25 µl of H₂O. About 10 µl (~50 units) of restriction enzyme BamHI were added to the solution of plasmid pBW32 DNA, and the resulting reaction was incubated at 37° C. for 2 hours. The BamHI-digested plasmid pBW32 DNA was precipitated with ethanol, resuspended in 10 µl of TE buffer, loaded onto an agarose gel, and electrophoresed until the ~1.9 kb BamHI restriction fragment that comprises the dihydrofolate reductase gene was separated from the other digestion products. The ~1.9 kb restriction fragment was then isolated from the gel and prepared for ligation in substantial accordance with the procedure of Example 4A; about 10 µg of the desired fragment were obtained and suspended in 50 µl of TE buffer.

About 2 µl of the BamHI-digested plasmid pBLT DNA prepared in Example 15A and 1 µl of the ~1.9 kb BamHI restriction fragment of plasmid pBW32 were added to 1 µl of 10×ligase buffer, 5 µl of H₂O, and 1 µl (~500 units) of T4 DNA ligase, and the resulting reaction was incubated at 16° C. overnight. The ligated DNA constituted the desired plasmids pBLTdhfr1 and pBLTdhfr2. A restriction site and function map of plasmid pBLTdhfr1 presented in FIG. 20 of the accompanying drawings. Plasmids pBLTdhfr1 and pBLTdhfr2 differ only with respect to the orientation of the ~1.9 kb BamHI restriction fragment that encodes the dhfr gene.

The ligated DNA was used to transform *E. coli* K12 HB101 in substantial accordance with the procedure of Example 2. The transformed cells were plated onto L agar containing ampicillin, and the ampicillin-resistant *E. coli* K12 HB101/pBLTdhfr1 and *E. coli* K12 HB101/pBLTdhfr2 transformants were identified by restriction enzyme analysis of their plasmid DNA.

EXAMPLE 16

Construction of Plasmids phdTPA and phdMTPA

A. Construction of Intermediate Plasmid pTPA602

About 50 µg of plasmid pTPA103 (Example 10, FIG. 14) in 45 µl of glass-distilled H₂O were added to 30 µl of 10×EcoRI buffer and 225 µl of H₂O. About 10 µl (~80 units) of restriction enzyme EcoRI were added to the solution of plasmid pTPA103 DNA, and the resulting reaction was incubated at 37° C. for 90 minutes. The EcoRI-digested plasmid pTPA103 DNA was precipitated with ethanol, resuspended in 50 µl of 1×loading buffer (10% glycerol and 0.02% bromophenol blue), loaded onto an agarose gel, and electrophoresed until the ~1.1 kb EcoRI restriction fragment was separated from the other reaction products. The ~1.1 kb EcoRI restriction fragment that comprises the TPA amino-terminal-encoding DNA and was isolated from the gel by electrophoresing the fragment into a dialysis bag. The fragment was then precipitated with ethanol and resuspended in 160 µl of H₂O.

About 40 µl of 10×HgaI buffer (0.5 M NaCl; 60 mM Tris-HCl, pH=7.4; and 0.1 M MgCl₂), 200 µl of glass-distilled H₂O, and 20 µl (about 10 units) of restriction enzyme HgaI were added to the solution of ~1.1 kb EcoRI restriction fragment, and the resulting reaction was incubated at 37° C. for 4 hours. The HgaI-digested DNA was precipitated with ethanol and then electrophoresed on a 5% acrylamide gel, and the ~520 bp restriction fragment that encodes the amino terminus of TPA was isolated onto DE81 paper and recovered. About 5 µg of the ~520 bp HgaI fragment were obtained and suspended in 50 µl of H₂O.

About 12.5 µl of 10×Klenow buffer (0.5 M Tris-HCl, pH=7.4, and 0.1 M MgCl₂), 2 µl of a solution that was 6.25 mM in each of the four deoxynucleotide triphosphates, 2 µl of 0.2 M DTT, 1 µl of 7 µg/ml BSA, 57.5 µl of glass-distilled H₂O, and 2 µl (~10 units) of Klenow enzyme (Boehringer-Mannheim Biochemicals, 7941 Castleway Dr., P.O. Box 50816, Indianapolis, Ind. 46250) were added to the solution of the ~520 bp HgaI restriction fragment, and the resulting reaction was incubated at 20° C. for 30 minutes. The Klenow-treated DNA was incubated at 70° C. for 15 minutes and precipitated with ethanol.

About 500 picomoles of BamHI linker (5'-CGGGATCCCG-3', double-stranded and obtained from New England Biolabs) were phosphorylated using polynucleotide kinase in a total reaction volume of 25 µl. The reaction was carried out in substantial accordance with the procedure described in Example 6A. The kinased BamHI linkers were added to the solution of Klenow-treated, ~520 bp HgaI restriction fragment together with 15 µl of 10×ligase buffer, 7 µl (~7 Weiss units) of T4 DNA ligase, and enough glass-distilled H₂O to bring the reaction volume to 150 µl. The resulting reaction was incubated at 16° C. overnight.

The ligation reaction was heat-inactivated, and the DNA was precipitated with ethanol and resuspended in 5 µl of 10×BamHI buffer and 45 µl of H₂O. About 1 µl (~16 units) of restriction enzyme BamHI was added to the solution of DNA, and the resulting reaction was incubated at 37° C. for 90 minutes. Then, another 16 units of BamHI enzyme were added to the reaction mixture, and the reaction was incubated at 37° C. for another 90 minutes. The reaction mixture was then electrophoresed on a 5% polyacrylamide gel, and the ~530 bp HgaI restriction fragment, now with BamHI ends, was purified from the gel in substantial accordance with the procedure of Example 6A. About 2 μg of the desired fragment were obtained and suspended in 20 μl of $H_2O$.

BamHI-digested, dephosphorylated plasmid pBR322 DNA can be obtained from New England Biolabs. About 0.1 μg of BamHI-digested, dephosphorylated plasmid pBR322 in 2 μl of $H_2O$ was added to 1 μl of the ~530 bp HgaI restriction fragment, with BamHI ends, of plasmid pTPA103, 14 μl of $H_2O$, and 1 μl (~1 Weiss unit) of T4 DNA ligase, and the resulting reaction was incubated at 16° C. overnight. The ligated DNA constituted the desired plasmid pTPA602 and an equivalent plasmid designated pTPA601, which differs from plasmid pTPA602 only with respect to the orientation of the inserted, ~530 bp restriction fragment. A restriction site and function map of plasmid pTPA602 is presented in FIG. 21 of the accompanying drawings.

The ligated DNA was used to transform *E. coli* K12 MM294 in substantial accordance with the procedure of Example 2, except that 50 mM $CaCl_2$ was used in the procedure. The transformed cells were plated on L agar containing ampicillin, and the ampicillin-resistant *E. coli* K12 MM294/pTPA602 and *E. coli* K12 MM294/pTPA601 cells were identified by restriction enzyme analysis of their plasmid DNA. Presence of an ~530 bp BamHI restriction fragment indicated that the plasmid was either pTPA602 or plasmid pTPA601.

B. Construction of Intermediate Plasmid pTPA603

About 5 μg of plasmid pTPA602 were dissolved in 20 μl of 10×BglII and 180 μl of $H_2O$. About 3 μl (~24 units) of restriction enzyme BglII were added to the solution of plasmid pTPA602 DNA, and the resulting reaction was incubated at 37° C. for 90 minutes. Then, ~13 μl of 10×BamHI buffer were added to the reaction mixture to bring the salt concentration of the reaction mixture up to that recommended for SalI digestion, and 2 μl (~20 units) of restriction enzyme SalI were added to the reaction. The reaction was incubated at 37° C. for another 2 hours; then, the DNA was precipitated with ethanol, resuspended in 75 μl of loading buffer, loaded onto an agarose gel, and electrophoresed until the ~4.2 kb BglII-SalI restriction fragment was separated from the other digestion products. The region of the gel containing the ~4.2 kb BglII-SalI restriction fragment was excised from the gel, frozen, and the frozen segment was wrapped in plastic and squeezed to remove the ~4.2 kb fragment. The DNA was precipitated and resuspended in 20 μl of $H_2O$; about 200 nanograms of the desired fragment were obtained.

About 12 μg of plasmid pTPA103 were dissolved in 15 μl of 10×BglII buffer and 135 μl of $H_2O$. About 2 μl (~16 units) of restriction enzyme BglII were added to the solution of plasmid pTPA103 DNA, and the resulting reaction was incubated at 37° C. for 90 minutes. About 10 μl of 10×BamHI buffer were added to the solution of BglII-digested plasmid pTPA103 DNA to bring the salt concentration of the reaction mixture up to that required for SalI digestion. Then, about 2 μl (~20 units) of restriction enzyme SalI were added to the solution of BglII-digested plasmid pTPA103 DNA, and the reaction was incubated at 37° C. for another 90 minutes. The BglII-SalI digested plasmid pTPA103 DNA was concentrated by ethanol precipitation and then loaded onto an agarose gel, and the ~2.05 kb BglII-SalI restriction fragment that encodes all but the amino-terminus of TPA was isolated from the gel, precipitated with ethanol and resuspended in 20 μl of $H_2O$. About 2 μg of the desired fragment were obtained.

About 5 μl of the ~4.2 kb BglII-SalI restriction fragment of plasmid pTPA602 and 2 μl of the ~2.05 kb BglII-SalI restriction fragment of plasmid pTPA103 were added to 2 μl of 10×ligase buffer, 10 μl of $H_2O$, and 1 μl (~1 Weiss unit) of T4 DNA ligase, and the resulting ligation reaction was incubated at 16° C. overnight. The ligated DNA constituted the desired plasmid pTPA603. A restriction site and function map of plasmid pTPA603 is presented in FIG. 22 of the accompanying drawings.

The ligated DNA was used to transform *E. coli* K12 MM294 in substantial accordance with the procedure of Example 2, except that 50 mM $CaCl_2$ was used in the procedure. The transformed cells were plated on L agar containing ampicillin, and the ampicillin-resistant *E. coli* K12 MM294/pTPA603 transformants were identified by restriction enzyme analysis of their plasmid DNA.

C. Construction of Plasmid pMTPA603

About 100 μg of plasmid pBLT (Example 14, FIG. 18) in 100 μl of TE buffer were added to 10 μl of 10×SstI (SstI is equivalent to restriction enzyme SacI) buffer (60 mM Tris-HCl, pH=7.4; 60 mM $MgCl_2$; 60 mM 2-mercaptoethanol; and 1 mg/ml BSA) and 25 μl of $H_2O$. About 10 μl (~50 units) of restriction enzyme SstI were added to the solution of plasmid pBLT DNA, and the resulting reaction was incubated at 37° C. for 2 hours. The SstI-digested plasmid pBLT DNA was precipitated with ethanol and resuspended in 10 μl of 10×BglII buffer and 85 μl of $H_2O$. About 5 μl (~50 units) of restriction enzyme BglII were added to the solution of SstI-digested plasmid pBLT DNA, and the resulting reaction was incubated at 37° C. for 2 hours.

The BglII-SstI-digested plasmid pBLT DNA was precipitated with ethanol, resuspended in 10 μl of $H_2O$, loaded onto an agarose gel, electrophoresed, and the ~690 bp BglII-SstI restriction fragment, which contains that portion of the modified TPA coding sequence wherein the deletion to get the modified TPA coding sequence has occurred, of plasmid pBLT was isolated from the gel in substantial accordance with the procedure of Example 4A. About 5 μg of the desired ~690 bp BglII-SstI restriction fragment of plasmid pBLT was obtained and suspended in 100 μl of $H_2O$.

About 5 μg of plasmid pTPA603 (Example 16B, FIG. 22) in 5 μl of TE buffer were added to 10 μl of 10×SstI buffer and 95 μl of $H_2O$. About 5 μl (~50 units) of restriction enzyme SstI were added to the solution of plasmid pTPA603 DNA, and the resulting reaction was incubated at 37° C. for 2 hours. The SstI-digested plasmid pTPA603 DNA was precipitated with ethanol and resuspended in 10 μl of 10×BglII buffer and 85 μl of $H_2O$. About 5 μl (~50 units) of restriction enzyme BglII were added to the solution of SstI-digested plasmid pTPA603 DNA, and the resulting reaction was incubated at 37° C. for 2 hours. The BglII-SstI-digested plasmid pTPA603 DNA was diluted to 100 μl in TE buffer and treated with calf-intestinal alkaline phosphatase in substantial accordance with the procedure of Example 2. The DNA was then precipitated with ethanol and resuspended in 10 μl of $H_2O$.

About 5 μl of the BglII-SstI-digested plasmid pTPA603 and 2 μl of the ~690 bp BglII-SstI restriction fragment of plasmid pBLT were added to 2 μl of 10×ligase buffer, 10 μl of $H_2O$, and 1 μl (~1000 units) of T4 DNA ligase, and the resulting ligation reaction was incubated at 16° C. overnight. The ligated DNA constituted the desired plasmid pMTPA603. Plasmid pMTPA603 is thus analogous in structure to plasmid pTPA603 (FIG. 22), except that plasmid pMTPA603 encodes modified TPA, and plasmid pTPA603 encodes TPA.

The ligated DNA was used to transform *E. coli* K12 HB101 in substantial accordance with the procedure of Example 2. The transformed cells were plated on L agar containing ampicillin, and the ampicillin-resistant *E. coli* K12 HB101/pMTPA603 transformants were identified by restriction enzyme analysis of their plasmid DNA.

D. Construction of Plasmid phdTPA

About 10 μg of plasmid pTPA603 (Example 16B, FIG. 22) in 10 μl of TE buffer were added to 10 μl of 10×BamHI buffer and 85 μl of $H_2O$. About 5 μl (~50 units) of restriction enzyme BamHI were added to the solution of plasmid pTPA603 DNA, and the resulting reaction was incubated at 37° C. for 2 hours. The BamHI-digested plasmid pTPA603 DNA was precipitated with ethanol, resuspended in 10 μl of $H_2O$, loaded onto an agarose gel, and electrophoresed until the ~1.90 kb BamHI restriction fragment that encodes TPA was separated from the other digestion products. The ~1.90 kb BamHI restriction fragment was isolated from the gel and resuspended in 50 μl of TE buffer; about 4 μg of the desired fragment were obtained.

About 2 μg of plasmid phd (Example 12, FIG. 16) in 2 μl of TE buffer were added to 2 μl of 10×BclI buffer and 14 μl of $H_2O$. About 2 μl (~10 units) of restriction enzyme BclI were added to the solution of plasmid phd DNA, and the resulting reaction was incubated at 50° C. for 2 hours. The reaction was stopped by extracting the reaction mixture first with phenol and then twice with chloroform. The BclI-digested plasmid phd DNA was then precipitated with ethanol and resuspended in 20 μl of TE buffer.

About 1 μl of the BclI-digested plasmid phd and 2 μl of the ~1.90 kb BamHI restriction fragment of plasmid pTPA603 were added to 1 μl of 10×ligase buffer, 5 μl of $H_2O$, and 1 μl (~500 units) of T4 DNA ligase. The resulting ligation reaction was incubated at 16° C. overnight. The ligated DNA constituted the desired plasmid phdTPA. A restriction site and function map of plasmid phdTPA is presented in FIG. 23 of the accompanying drawings.

The ligated DNA was used to transform *E. coli* K12 HB101 (NRRL B-15626) in substantial accordance with the procedure of Example 2. The transformation mixture was plated on L agar containing ampicillin, and the ampicillin-resistant *E. coli* K12 HB101/phdTPA cells were identified by restriction enzyme analysis. The ~1.90 kb BamHI restriction fragment could insert into BclI-digested plasmid phd in either one of two orientations, only one of which places the TPA coding sequence in the proper position to be expressed under the control of the BK enhancer-adenovirus late promoter cassette and thus results in the desired plasmid phdTPA.

E. Construction of Plasmid phdMTPA

About 10 μg of plasmid pMTPA603 (Example 16C) in 10 μl of TE buffer were added to 10 μl of 10×BamHI buffer and 85 μl of $H_2O$. About 5 μl (~50 units) of restriction enzyme BamHI were added to the solution of plasmid pMTPA603 DNA, and the resulting reaction was incubated at 37° C. for 2 hours. The BamHI-digested plasmid pMTPA603 DNA was precipitated with ethanol, resuspended in 10 μl of $H_2O$, loaded onto an agarose gel, and electrophoresed until the ~1.35 kb BamHI restriction fragment that encodes modified TPA was separated from the other digestion products. The ~1.35 kb BamHI restriction fragment was isolated from the gel and resuspended in 20 μl of TE buffer; about 4 μg of the desired fragment were obtained.

About 1 μl of the BclI-digested plasmid phd prepared in Example 16D and 2 μl of the ~1.35 kb BamHI restriction fragment of plasmid pMTPA603 were added to 1 μl of 10×ligase buffer, 5 μl of $H_2O$, and 1 μl (~500 units) of T4 DNA ligase. The resulting ligation reaction was incubated at 16° C. overnight. The ligated DNA constituted the desired plasmid phdMTPA. A restriction site and function map of plasmid phdMTPA is presented in FIG. 24 of the accompanying drawings.

The ligated DNA was used to transform *E. coli* K12 HB101 in substantial accordance with the procedure of Example 2. The transformation mixture was plated on L agar containing ampicillin, and the ampicillin-resistant *E. coli* K12 HB101/phdMTPA cells were identified by restriction enzyme analysis of their plasmid DNA. The ~1.35 kb BamHI restriction fragment could insert into BclI-digested plasmid phd in either one of two orientations, only one of which places the TPA coding sequence in the proper position to be expressed under the control of the BK enhancer-adenovirus late promoter and thus results in the desired plasmid phdMTPA.

EXAMPLE 17

Construction of an Improved BK Enhancer-Adenovirus Late Promoter Cassette

The transcription-enhancing effect of the BK enhancer can be significantly increased by placing the enhancer from 0 to 300 nucleotides upstream of the 5' end of the CAAT region or CAAT region equivalent of an adjacent eukaryotic promoter. The sequence and functional elements of the present BK enhancer-adenovirus 2 late promoter cassette, before modification to achieve greater enhancing activity, is depicted below. This depiction assumes that the BK enhancer is from the prototype strain of BK virus, available from the ATCC under the VR-837. However, ATCC VR-837 consists of a mixture of BK variants. Plasmid pBal8cat and the other BK enhancer-containing plasmids of the invention comprise this BK enhancer variant and not the BK prototype enhancer depicted below. As stated above, however, any BK enhancer variant can be used in the methods and compounds of the present invention. Plasmid pBal8cat can be obtained in *E. coli* K12 HB101 cells from the Northern Regional Research Center, Peoria, Ill. 61604 under the accession number NRRL B-18267.

```
          HindIII                                                       60
5'-AAGCTTTTCT CATTAAGGGA AGATTTCCCC AGGCAGCTCT TTCAAGGCT  AAAAGGTCCA
   ------

120
   TGAGCTCCAT GGATTCTTCC CTGTTAAGAA CTTTATCCAT TTTTGCAAAA ATTGCAAAAG
                                            StuI                       180
   AATAGGGATT TCCCCAAATA GTTTTGCTAG GCCTCAGAAA AAGCCTCCAC ACCCTTACTA
                                   --------
                                                                       240
   CTTGAGAGAA AGGGTGGAGG CAGAGGCGGC CTCGGCCTCT TATATATTAT AAAAAAAAAG
```

-continued

```
                                                                       300
         *----------------------first repeat of the BK enhancer---------
     GCCACAGGGA GGAGCTGCTT ACCCATGGAA TGCAGCCAAA CCATGACCTC AGGAAGGAAA
                                                                       360
     ----------* *-----------second repeat of the BK enhancer----------*
     GTGCATGACT CACAGGGGAA TGCAGCCAAA CCATGACCTC AGGAAGGAAA GTGCATGACT
                                                                       420
     *------------------------------third repeat of the BK enhancer--
     CACAGGGAGG AGCTGCTTAC CCATGGAATG CAGCCAAACC ATGACCTCAG GAAGGAAAGT
     ------*|-----43 bp insert; not found in BK(DUN)------
   |          480
     GCATGACTGG GCAGCCAGCC AGTGGCAGTT AATAGTGAAA CCCCGCCGAC AGACATGTTT
                                                                       540
     TGCGAGCCTA GGAATCTTGG CCTTGTCCCC AGTTAAACTG GACAAAGGCC ATGGTTCTGC
         StuI/PvuII
   SstI                                 600
     GCCAGGCTGT CCTCGAGCGG TGTTCCGCGG TCCTCCTCGT ATAGAAACTC GGACCACTCT
     ------              ------
                                                                       660
     GAGACGAAGG CTCGCGTCCA GGCCAGCACG AAGGAGGCTA AGTGGGAGGG GTAGCGGTCG
                                                                       720
     TTGTCCACTA GGGGGTCCAC TCGCTCCAGG GTGTGAAGAC ACATGTCGCC CTCTTCGGCA CAAT Region                  780
     TCAAGGAAGG TGATTGGTTT ATAGGTGTAG GCCACGTGAC CGGGTGTTCC TGAAGGGGGG
                                                  start site of transcription
          TATA Box                       *---
   '                             840
     CTATAAAAGG GGGTGGGGGC GCGTTCGTCC TCACTCTCTT CCGCATCGCT GTCTGCGAGG
     -------
                                  874
         BclI linker              HindIII
     GCCAGCTGAT CAGCCTAGGC TTTGCAAAAA GCTT-3'
``` wherein A is deoxyadenyl; G is deoxyguanyl; C is deoxycytidyl; and T is thymidyl.

The prototype BK enhancer is defined by the three repeated sequences indicated in the sequence above and functions similarly, with respect to an adjacent sequence, in either orientation. To bring the enhancer, more specifically, the 3' end of the third repeat (which depends on the orientation) of the BK enhancer, closer to the 5' end of the CAAT region of the adenovirus-2 late promoter, about 82 $\mu$g of SstI-digested plasmid pBLcat DNA in 170 $\mu$l of TE buffer were added to 20 $\mu$l of 5×Bal31 nuclease buffer (0.1 M Tris-HCl, pH=8.1; 0.5 M NaCl; 0.06 M CaCl$_2$; and 5 mM Na$_2$EDTA) and 9 $\mu$l of Bal31 nuclease, which was composed of 6 $\mu$l (~6 units) of "fast" and 3 $\mu$l (~3 units) of "slow" Bal31 enzyme (marketed by International Biotechnologies, Inc., P.O. Box 1565, New Haven, Conn. 06506). The reaction was incubated at 30° C. for about 3 minutes; then, after about 10 $\mu$l of 0.1 M EGTA were added to stop the reaction, the Bal31-digested DNA was collected by ethanol precipitation and centrifugation. The DNA pellet was resuspended in 1×Klenow buffer and treated with Klenow enzyme in substantial accordance with procedures previously described herein.

The Klenow-treated DNA was resuspended in 10 $\mu$l of TE buffer; about 1 $\mu$l of the DNA was then self-ligated in 10 $\mu$l of 1×ligase buffer using T4 DNA and RNA ligase as previously described. The ligated DNA was used to transform E. coli K12 HB101, and then the transformants were plated onto L agar containing ampicillin. Restriction enzyme analysis was used to determine which transformants contained plasmids with an appropriately-sized BK enhancer-adenovirus 2 late promoter cassette. The foregoing procedure generates a number of plasmids in which the BK enhancer is placed within 0 to 300 nucleotides upstream of the CAAT region of the adenovirus late promoter. One plasmid resulting from the above procedure was designated plasmid pBal8cat. Plasmid pBal8cat is available from the NRRL under the accession number NRRL B-18267. Plasmid pBal8cat contains a variant of the BK enhancer that is believed to contain two repeat sequences of about 90 bp each. This variant enhancer can be used in the method of the present invention by placing the 3' end of the second repeat within 0 to 300 nucleotides of the CAAT region of the adenovirus late promoter.

Those skilled in the art will recognize that the foregoing procedure produced a number of distinct plasmids, of which plasmid pBal8cat is illustrative. These plasmids, as a group, represent placing the BK enhancer at a variety of distances less than 300 nucleotides from the CAAT region of the Ad2 late promoter and thus comprise an important aspect of the present invention. This method for improving the activity of a BK enhancer, which can be achieved using the foregoing procedure or others known to those skilled in the art, can be used with any BK enhancer and any eukaryotic promoter.

EXAMPLE 18

Construction of Eukaryotic Host Cell Transformants of the Expression Vectors of the Present Invention and Determination of Recombinant Gene Expression Levels in Those Transformants An important aspect of the present invention concerns the use of the BK enhancer to stimulate gene expression in the presence of the E1A gene product. Because 293 cells constitutively express the E1A gene product, 293 cells are the preferred host for the eukaryotic expression vectors of the present invention. 293 cells are human embryonic kidney cells transformed with adenovirus type 5 (note that any particular type of adenovirus can be used to supply the E1A gene product in the method of the present invention) and are available from the ATCC under the accession number CRL 1573. However, the expression vectors of the present invention function in a wide variety of host cells, even if the E1A gene product is not present. Furthermore, the E1A gene product can be introduced into a non-E1A-producing cell line either by transformation with a vector of the present invention that comprises the E1A gene, such as plasmids pLPCE1A and pLPCE1A1, or with sheered adenovirus DNA, or by infection with adenovirus.

The transformation procedure described below refers to 293 cells as the host cell line; however, the procedure is generally applicable to most eukaryotic cell lines. A variety of cell lines have been transformed with the vectors of the present invention; some of the actual transformants constructed and related information are presented in the Tables accompanying this Example. Because of the great number of expression vectors of the present invention, the transformation procedure is described generically, and the actual transformants constructed are presented in the Tables.

293 cells are obtained from the ATCC under the accession number CRL 1573 in a 25 mm$^2$ flask containing a confluent monolayer of about $5.5 \times 10^6$ cells in Eagle's Minimum Essential Medium with 10% heat-inactivated horse serum. The flask is incubated at 37° C.; medium is changed twice weekly. The cells are subcultured by removing the medium, rinsing with Hank's Balanced Salts solution (Gibco), adding 0.25% trypsin for 1–2 minutes, rinsing with fresh medium, aspirating, and dispensing into new flasks at a subcultivation ratio of 1:5 or 1:10.

One day prior to transformation, cells are seeded at $0.7 \times 10^6$ cells per dish. The medium is changed 4 hours prior to transformation. Sterile, ethanol-precipitated plasmid DNA dissolved in TE buffer is used to prepare a 2×DNA-CaCl$_2$ solution containing 40 µg/ml DNA and 250 mM CaCl$_2$. 2×HBS is prepared containing 280 mM NaCl, 50 mM Hepes, and 1.5 mM sodium phosphate, with the pH adjusted to 7.05–7.15. The 2×DNA-CaCl$_2$ solution is added dropwise to an equal volume of sterile 2×HBS. A one ml sterile plastic pipette with a cotton plug is inserted into the mixing tube that contains the 2×HBS, and bubbles are introduced by blowing while the DNA is being added. The calcium-phosphate-DNA precipitate is allowed to form without agitation for 30–45 minutes at room temperature.

The precipitate is then mixed by gentle pipetting with a plastic pipette, and one ml (per plate) of precipitate is added directly to the 10 ml of growth medium that covers the recipient cells. After 4 hours of incubation at 37° C., the medium is replaced with DMEM with 10% fetal bovine serum and the cells allowed to incubate for an additional 72 hours before providing selective pressure. For transformants expressing recombinant human protein C, the growth medium contained 1 to 10 µg/ml vitamin K, a cofactor required for γ-carboxylation of the protein. For plasmids that do not comprise a selectable marker that functions in eukaryotic cells, the transformation procedure utilizes a mixture of plasmids: the expression vector of the present invention that lacks a selectable marker; and an expression vector that comprises a selectable marker that functions in eukaryotic cells. This co-transformation technique allows for the identification of cells that comprise both of the transforming plasmids.

For cells transfected with plasmids containing the hygromycin resistance-conferring gene, hygromycin is added to the growth medium to a final concentration of about 200 to 400 µg/ml. The cells are then incubated at 37° C. for 2–4 weeks with medium changes at 3 to 4 day intervals. The resulting hygromycin-resistant colonies are transferred to individual culture flasks for characterization. The selection of neomycin (G418 is also used in place of neomycin)-resistant colonies is performed in substantial accordance with the selection procedure for hygromycin-resistant cells, except that G418 is added to a final concentration of 400 µg/ml rather than hygromycin. 293 cells are dhfr positive, so 293 transformants that contain plasmids comprising the dhfr gene are not selected solely on the basis of the dhfr-positive phenotype, which is the ability to grow in media that lacks hypoxanthine and thymine. Cell lines that do lack a functional dhfr gene and are transformed with dhfr-containing plasmids can be selected for on the basis of the dhfr+ phenotype.

The use of the dihydrofolate reductase (dhfr) gene as a selectable marker for introducing a gene or plasmid into a dhfr-deficient cell line and the subsequent use of methotrexate to amplify the copy number of the plasmid has been well established in the literature. Although the use of dhfr as a selectable and amplifiable marker in dhfr-producing cells has not been well studied, efficient coamplification in primate cells requires an initial selection using a directly selectable marker before the coamplification using methotrexate. The use of the present invention is not limited by the selectable marker used. Moreover, amplifiable markers such as metallothionein genes, adenosine deaminase genes, or members of the multigene resistance family, exemplified by P-glycoprotein, can be utilized. In 293 cells, it is advantageous to transform with a vector that contains a selectable marker such as the hygromycin B resistance-conferring gene and then amplify using methotrexate, which cannot be used for direct selection of murine dhfr-containing plasmids in 293 cells. The levels of coamplification can be measured using Southern hybridization or other methods known in the art. Tables 7 and 8 display the results of coamplification experiments in 293 cells.

TABLE 3

Expression Levels in 293 Cell Transformants

| Plasmid | Expressed Gene | Expression Level (as measured by amount of expressed gene product in cell media) |
|---|---|---|
| pLPChygl | Protein C | 0.1–4.0 µg/10$^6$ cells/day. |
| pLPCdhfrl | Protein C | 0.1–4.0 µg/10$^6$ cells/day. |
| pLPC4 | Protein C | 0.1–2.0 µg/10$^6$ cells/day, cotransformed with plasmid pSV2hyg. |
| pLPC5 | Protein C | 0.1–2.0 µg/10$^6$ cells/day, cotransformed with plasmid pSV2hyg. |
| pLPChdl | Protein C | ~1.2 µg/10$^6$ cells/day, |
| phdTPA | TPA | in a transient assay conducted 24–36 hours post-transformation, about 0.5–1.25 µg/10$^6$ cells, if the VA gene product is present in the host cell and about 10-fold less if not. Stable transformants produce about 2.5–3.8 µg/4 × 10$^6$ cells/day. |

TABLE 4

Expression Levels in MK2 (ATCC CCL7) Cell Transformants

| Plasmid | Expressed Gene | Expression Level |
|---|---|---|
| pLPChygl | Protein C | 0.005–0.040 µg/10$^6$ cells/day. |
| pLPChd | Protein C | 0.025–0.4 µg/10$^6$ cells/day. |
| pLPC4 | Protein C | 0.025–0.15 µg/10$^6$ cells/day, cotransformed with plasmid pSV2hyg. |
| pLPC5 | Protein C | 0.025–0.18 µg/10$^6$ cells/day, cotransformed with plasmid pSV2hyg. |

TABLE 5

Relative Levels of Chloramphenicol Acetylatransferase (CAT) Produced by Recombinant Plasmids in Various Human and Monkey Kidney Cell Lines

| | Relative Level* of CAT in Cell Line: | | | |
|---|---|---|---|---|
| Plasmid | 293 (ATCC CRL 1573) | k816-4** | COS-1 (ATCC CRL 1650) | MK2 (ATCC CCL7) |
| pLPcat | 0.17 | 0.16 | 0.18 | 0.06 |
| pSV2cat | 1 | 1 | 1 | 1 |
| pBLcat | 10.4 | 2.7 | 1.4 | 1.3 |

TABLE 5-continued

Relative Levels of Chloramphenicol Acetylatransferase (CAT) Produced by Recombinant Plasmids in Various Human and Monkey Kidney Cell Lines Relative Level* of CAT in Cell Line:

| Plasmid | 293 (ATCC CRL 1573) | k816-4** | COS-1 (ATCC CRL 1650) | MK2 (ATCC CCL7) |
|---|---|---|---|---|
| pSBLcat | 3.9 | 5.4 | 3.4 | 2.8 |
| pSLcat | 0.20 | 3.6 | NT | 1.05 |
| pBal8cat | 17 | 1.8 | NT | 1.2 |

*The values for the relative levels of CAT produced in each cell line were based on the level of CAT from plasmid pSV2cat as unity in that cell line. Results are the average of from 2 to 6 individual determinations of each data point. ND = not detected. NT = not tested. Plasmid pSLcat is analogous to plasmid pBLcat but has the SV40 enhancer rather than the BK enhancer. Only the 293 cell line produces E1A. The COS and k816-4 cell lines produce T antigen.

**k816-4 cells were prepared by transformation of primary human kidney cells with a plasmid, designated pMK16, 8–16 (obtained from Y. Gluzman, Cold Spring Harbor), containing an SV40 genome with a defect in the origin of replication. This cell line constitutively produces the T antigen of SV40. The k816-4 cell line is essentially the same as cell line SV1, an SV40-transformed human kidney line, described by E.O. Major, Polyomaviruses and Human Neurological Disease (Alan R. Liss, Inc., N.Y. 1983, eds D. Madden, and J. Sever).

TABLE 6

Relative Levels of Chloramphenicol Acetylatransferase (CAT) Produced by Recombinant Plasmids in Various Human and Monkey Kidney Cell Lines Corrected for Relative Differences in Plasmid Copy Number Relative Level* of CAT in Cell Line:

| Plasmid | 293 | k816-4 | MK2 |
|---|---|---|---|
| pLPcat | 0.18 | 0.25 | 0.015 |
| pSV2cat | 1 | 2.1 | 0.25 |
| pBLcat | 12.6 | 5.8 | 0.32 |

*The values for the relative levels of CAT produced in each cell line were corrected by dividing the level of CAT in the cell lysate by the amount of plasmid DNA, as determined by hybridization analysis, in the same cell lysate. The corrected value for plasmid pSV2cat in 293 cells was taken as unity.

TABLE 7

Methotrexate sensitivity and level of HPC expression from 293 cells transformed by plasmid pLPChd and initially selected for hygromycin resistance.

| Level of methotrexate ($\mu$M) | Number of colonies | Level of HPC (ng/$10^6$ cells) |
|---|---|---|
| 0 | confluent | 575 |
| 0.05 | confluent | 1794 |
| 0.2 | 500+ | 3786 |
| 0.4 | 32 | 235 |
| 0.8 | 53 | 325 |
| 1.6 | 58 | 165 |
| 3.2 | 44 | 310 |

TABLE 8

Level of HPC in clones selected for growth in increasing levels of methotrexate following initial selection with hygromycin (A) or G418(B)

HPC (ng/$10^6$ cells/day) in MTX ($\mu$M) level of:

| Clone | 0.05 | 0.1 | 0.2 | 0.4 | 0.8 | 1.6 | 3.2 | 5.0 | 10 |
|---|---|---|---|---|---|---|---|---|---|
| A | | | | | | | | | |
| Pool 1118 | 270 | 210 | 160 | | 290 | | | | |
| -1 | 1820 | 310 | 370 | 150 | 350 | 360 | | | |
| -10 | 2170 | 220 | 370 | 110 | 200 | | | | |
| -35 | 1520 | | | 210 | 200 | | | | |
| -26 | 1300 | 240 | 460 | 150 | 160 | | | | |
| -37 | 2400 | | 470 | 630 | 530 | 580 | | | |
| -21 | 1100 | 1700 | | | 3100 | 2450 | 2060 | 1100 | 680 |
| 21 subclones | | | | | | | | | |
| 21-1 | | | | | 4100 | | | | |
| 21-2 | | | | | 4300 | | | | |
| 21-3 | | | | | 3010 | | | | |
| 21-4 | | | | | 2970 | | | | |
| 21-5 | | | | | 4130 | | | | |
| 21-6 | | | | | 2830 | | | | |
| 21-7 | | | | | 1130 | | | | |
| 21-10b-1 | | | | | | | | | 5790 |
| 21-10-3 | | | | | | | | | 4700 |
| 21-10b-3 | | | | | | | | | 12175 |
| 21-10b-4 | | | | | | | | | 11155 |
| 21-10b-5 | | | | | | | | | 10235 |
| 21-10b-6 | | | | | | | | | 8490 |
| 21-10-7 | | | | | | | | | <20 |
| 21-10b-7 | | | | | | | | | 4990 |

TABLE 8-continued

Level of HPC in clones selected for growth in increasing levels of methotrexate following initial selection with hygromycin (A) or G418(B)

| Clone | HPC (ng/10⁶ cells/day) in MTX (μM) level of: | | | | | | | | |
|---|---|---|---|---|---|---|---|---|---|
| | 0.05 | 0.1 | 0.2 | 0.4 | 0.8 | 1.6 | 3.2 | 5.0 | 10 |
| 21-10b-10 | | | | | | | | | 9500 |
| 21-10-2 | | | | | | | | | 1705 |
| B* | | | | | | | | | |
| Pool 0925 | | | 315 | | | 600 | | 2200 | |
| Subclones | | | | | | | | | |
| hdA6 | | | | | | | | 37000 | |
| hdA4 | | | | | | | | 22250 | |
| A1 | | | | | | | | 40000 | |
| A2 | | | | | | | | 33750 | |
| A3 | | | | | | | | 44250 | |

*denotes cotransfection with plasmids pLPChd and pSV2neo.

EXAMPLE 19

Cell line AV12 (ATCC CRL 9595) can be transformed in substantial accordance with the procedure described for 293 cells in Example 18. However, unlike 293 cells, AV12 cells can be directly selected with methotrexate (200–500 nM) when transformed with a vector containing the murine dhfr gene. Table 6, below, illustrates the advantages of producing a γ-carboxylated protein, in this instance, activated human protein C, in an adenovirus-transformed host cell. The transformants were selected using hygromycin B or methotrexate; transformants produced ~2 to 4 μg/ml of human protein C. Protein C levels can be increased to ~10 μg/ml by amplification with methotrexate. The protein C was activated and its activity determined as described in Grinnell et al., 1987, Bio/Technology 5:1189. Activity values are based on an activity of 1.0 for human plasma protein. The activities are expressed in ratios of activated partial thromboplastin time (APTT) over amidolytic (serine protease) activity or amount of protein C antigen (ELISA).

TABLE 9

Functional Activity of Protein C Produced in Adenovirus-transformed Cell Lines

| Cell Line | APTT/Amidolytic | APTT/ELISA |
|---|---|---|
| 293/pLPChd | 1.2–1.7 | 1.2–1.7 |
| AV12/pLPChd | 0.9–1.45 | 0.9–1.45 |
| SA7/pLPChd | nd | 1.0 |
| SV20/pLPChd | nd | 0.95 | nd = not determined; SA7 and SV20 are Syrian hamster cell lines transformed with simian adenovirus 7 and simian virus 20, respectively.

Table 9 shows that the recombinant protein C activity produced in an adenovirus-transformed host cell is at least as active as that found in human blood. In non-adenovirus-transformed host cells, the anticoagulant activity of the recombinant protein C produced never exceeds 60% of the activity of human blood-derived protein C.

EXAMPLE 20

Construction of Plasmids p4-14 and p2-5, Plasmids that Encode the Tripartite Leader of Adenovirus Plasmids p4-14 and p2-5 both utilize the improved BK-enhancer adenovirus late promoter cassette of plasmid pBal8cat and the tripartite leader of adenovirus to drive high level expression of human protein C in eukaryotic host cells. The DNA encoding the adenovirus tripartite leader (TPL) was isolated from adenovirus; numbers in parentheses after restriction enzyme cut sites refer to map units of adenovirus.

Plasmid pUC13 (commercially available from BRL) was digested with restriction enzymes SphI and BamHI and then ligated with the TPL-encoding ~7.2 kb SphI (5135)-BclI (12,301) restriction fragment of adenovirus type 2 to yield plasmid pTPL4. Part of an intron was deleted from the TPL-encoding DNA by digesting plasmid pTPL4 with restriction enzymes SauI (7616) and BglII (8904), treating with Klenow enzyme, and religating to yield plasmid pΔTPL. Plasmid pΔTPL was then digested with restriction enzyme XhoI, and the ~2.62 kb XhoI fragment encoding the TPL (XhoI sites at 5799 and 9689 of adenovirus) was isolated and prepared for ligation.

Plasmid pBLcat was digested with restriction enzymes XhoI and BclI and then ligated with the linker:

to yield plasmid pBΔLcat. This construction replaces the adenovirus late promoter on plasmid pBLcat with the linker sequence. Plasmid pBΔLcat was digested with restriction enzyme XhoI and ligated with the ~2.62 kb XhoI restriction fragment of plasmid pΔTPL to yield plasmid PBΔL-TPL, in which the TPL-encoding fragment is correctly positioned to place the BK enhancer, adenovirus major late promoter, and TPL in alignment for expression of the CAT gene.

Plasmid p2-5 was then constructed by ligating these fragments: (1) the AatII-BclI restriction fragment of plasmid pLPChd1, which encodes the dhfr gene; (2) the protein C-encoding, BclI restriction fragment of plasmid pLPChd1; (3) the TPL-encoding PvuII-BclI restriction fragment of plasmid pBΔL-TPL; and (4) the BK-enhancer-Ad2MLP-encoding PvuII-AatII restriction fragment of plasmid pBal8cat. Plasmid p2-5 thus contains the dhfr gene as a selectable, amplifiable marker and the BK enhancer, Ad2MLP, and Ad2TPL correctly positioned to drive expression of human protein C.

Plasmid p4-14 is analogous to plasmid p2-5 but was constructed via an intermedite plasmid designated pBal8TPL. Plasmid pBal8TPL was constructed by ligating fragments 1, 3, and 4, used in the construction of plasmid p2-5, as described in the preceding paragraph. Plasmid pBal8TPL was then digested with restriction enzyme XhoI treated with Klenow enzyme to make the XhoI ends blunt-ended and then ligated with the human protein C-encoding, Klenow-treated BclI restriction fragment of plasmid pLPChd1 to yield plasmid p4-14. Thus, plasmid p4-14 only differs from plasmid p2-5 in that the protein C-encoding DNA was inserted at the XhoI site in the fragment derived from plasmid pBΔL-TPL, whereas in plasmid p2-5, this DNA was inserted at the BclI site in the DNA derived from plasmid pBΔL-TPL.

Plasmid p4-14 and p2-5 drive high-level expression of human protein C. In AV12 cells, plasmids p4-14 and p2-5 can be directly selected using 200–500 nM methotrexate. AV12/p4-14 transformants, before amplification, express 5–6 times more human protein C than AV12/pLPCdhfr transformants. Amplification with methotrexate further increases the amount of human protein C produced by the cells. Plasmids p4-14 and p2-5 are thus illustrative of the higher expression levels achieved using the TPL of adenovirus.

I claim:

1. A method of expressing a gene of interest in a eukaryotic host cell, said method comprising:
   (a) introducing into said eukaryotic host cell a recombinant DNA vector comprising, a viral enhancer selected from the group consisting of a SV40 enhancer and a BK enhancer, a human viral promoter, the gene of interest, and an SV40 T antigen gene;
   (b) culturing said eukaryotic host cell transformed in step (a) under conditions that allow expression of said DNA sequence and expression of the gene of interest.

2. The method of claim 1 wherein the viral enhancer is a SV40 enhancer.

3. The method of claim 1 wherein the viral enhancer is a BK enhancer.

4. A method of expressing a gene of interest in a eukaryotic host cell, said method comprising:
   (a) introducing into said eukaryotic host cell a recombinant DNA vector comprising, a viral enhancer, a human viral promoter selected from the group consisting of an adenovirus late promoter and a BK virus late promoter, the gene of interest, and an SV40 T antigen gene;
   (b) culturing said eukaryotic host cell transformed in step (a) under conditions that allow expression of said DNA sequence and expression of the gene of interest.

5. The method of claim 4, wherein the viral promoter is an adenovirus late promoter.

6. The method of claim 4, wherein the viral promoter is an BK virus late promoter.

7. The method of claim 4 wherein the gene of interest encodes a gamma-carboxylated protein.

8. The method of claim 7, wherein the gamma-carboxylated protein is selected from a group consisting of Factor VII, Factor IX, Factor V, protein C, protein S, protein Z, and prothrombin.

9. The method of claim 7, wherein the gamma-carboxylated protein is protein C.

10. The method of claim 4 wherein the eukaryotic host cell is an adenovirus transformed host cell.

11. The method of claim 10, wherein the adenovirus transformed cell is selected from the group consisting of AV12 cells and human embryonic kidney 293 cells.

12. The method of claim 11, wherein the adenovirus transformed cell is an AV12 cell.

13. The method of claim 11, wherein the adenovirus transformed cell is a human embryonic kidney 293 cell.

14. A method of expressing a gene of interest in a eukaryotic host cell, said method comprising:
   (a) introducing into said eukaryotic host cell,
      (i) a first recombinant DNA vector comprising, a viral enhancer selected from the group consisting of a SV40 enhancer and a BK enhancer, a human viral promoter, the gene of interest, and
      (ii) a second recombinant DNA vector comprising, an SV40 T antigen gene;
   (b) culturing said eukaryotic host cell transformed in step (a) under conditions that allow expression of said DNA sequence and expression of the gene of interest.

15. The method of claim 14 wherein the viral enhancer is a SV40 enhancer.

16. The method of claim 14 wherein the viral enhancer is a BK enhancer.

17. A method of expressing a gene of interest in a eukaryotic host cell, said method comprising:
   (a) introducing into said eukaryotic host cell,
      (i) a first recombinant DNA vector comprising, a viral enhancer, a human viral promoter selected from the group consisting of an adenovirus late promoter and a BK virus late promoter, the gene of interest, and
      (ii) a second recombinant DNA vector comprising, an SV40 T antigen gene;
   (b) culturing said eukaryotic host cell transformed in step (a) under conditions that allow expression of said DNA sequence and expression of the gene of interest.

18. The method of claim 17, wherein the viral promoter is an adenovirus late promoter.

19. The method of claim 17, wherein the viral promoter is an BK virus late promoter.

20. The method of claim 17, wherein the gene of interest encodes a gamma-carboxylated protein.

21. The method of claim 20, wherein the gamma-carboxylated protein is selected from a group consisting of Factor VII, Factor IX, Factor V, protein C, protein S, protein Z, and prothrombin.

22. The method of claim 20, wherein the gamma-carboxylated protein is protein C.

23. The method of claim 17, wherein the eukaryotic host cell is an adenovirus transformed host cell.

24. The method of claim 23, wherein the adenovirus transformed cell is selected from the group consisting of AV12 cells and human embryonic kidney 293 cells.

25. The method of claim 23, wherein the adenovirus transformed cell is an AV12 cell.

26. The method of claim 23, wherein the adenovirus transformed cell is a human embryonic kidney 293 cell.

* * * * *